US011103574B2

(12) United States Patent
Matano et al.

(10) Patent No.: US 11,103,574 B2
(45) Date of Patent: Aug. 31, 2021

(54) INFECTIOUS DISEASE VACCINE USING NON-INFECTIOUS PARAMYXOVIRUS PARTICLE

(71) Applicants: Japan as represented by the Director-General of National Institute of Infectious Diseases, Tokyo (JP); ID Pharma Co., Ltd., Tokyo (JP)

(72) Inventors: Tetsuro Matano, Tokyo (JP); Makoto Inoue, Tokyo (JP); Hiroto Hara, Tokyo (JP); Tsugumine Shu, Tokyo (JP)

(73) Assignees: Japan, as represented by the Director-General of National Institute of Infectious Disease, Tokyo (JP); ID Pharma Co., Ltd., Tokyo (JP)

( * ) Notice: Subject to any disclaimer, the term of this patent is extended or adjusted under 35 U.S.C. 154(b) by 76 days.

(21) Appl. No.: 16/342,070

(22) PCT Filed: Nov. 17, 2017

(86) PCT No.: PCT/JP2017/041492
§ 371 (c)(1),
(2) Date: Oct. 2, 2019

(87) PCT Pub. No.: WO2018/092887
PCT Pub. Date: May 24, 2018

(65) Prior Publication Data
US 2020/0155669 A1 May 21, 2020

(30) Foreign Application Priority Data
Nov. 17, 2016 (JP) .............................. JP2016-224475

(51) Int. Cl.
*A61K 39/21* (2006.01)
*C12N 7/00* (2006.01)

(52) U.S. Cl.
CPC .............. *A61K 39/21* (2013.01); *C12N 7/00* (2013.01); *C12N 2740/10022* (2013.01); *C12N 2740/10034* (2013.01); *C12N 2760/18823* (2013.01); *C12N 2760/18843* (2013.01)

(58) Field of Classification Search
None
See application file for complete search history.

(56) References Cited

U.S. PATENT DOCUMENTS

2002/0002143 A1    1/2002  Kano et al.
2002/0169306 A1*  11/2002  Kitazato ................. C12N 7/00
                                                    536/23.4
2015/0329874 A1*  11/2015  Fukumura ........... A61K 39/0011
                                                    435/91.1

FOREIGN PATENT DOCUMENTS

| EP | 1186667 A1 | 3/2002 |
|----|------------|--------|
| EP | 2813574 A1 | 12/2014 |
| EP | 2940134 A1 | 11/2015 |
| WO | WO-00/70070 A1 | 11/2000 |
| WO | WO-2007/064802 A1 | 6/2007 |
| WO | WO-2014/103310 A1 | 7/2014 |
| WO | WO-2016/069518 A2 | 5/2016 |

OTHER PUBLICATIONS

Mantano et al. vol. 75, p. 11891-11896 Journal of Virology (Year: 2001).*
Extended European Search Report for European Patent Application No. 17871536.3 dated Jun. 25, 2020 (11 pages).
Iida et al., "Sendai virus based vectors," Uirusu. 53(2):171-5 (2003) (English language translation not provided).
International Search Report for International Application No. PCT/JP2017/041492, dated Jan. 9, 2018 (English language translation provided) (6 pages).
Matano et al., "Rapid appearance of secondary immune responses and protection from acute CD4 depletion after a highly pathogenic immunodeficiency virus challenge in macaques vaccinated with a DNA prime/Sendai virus vector boost regimen," J Virol. 75(23):11891-6 (2001).
Takeda et al., "Evaluation of the immunogenicity of replication-competent V-knocked-out and replication-defective F-deleted Sendai virus vector-based vaccines in macaques," Vaccine. 26(52):6839-43 (2008).
Zimmer et al., "A chimeric respiratory syncytial virus fusion protein functionally replaces the F and HN glycoproteins in recombinant Sendai virus," J Virol. 79(16):10467-77 (2005).
World Health Organization. World health statistics 2016: monitoring health for the SDGs, sustainable development goals. World Health Organization. (2016) (136 pages).
State of World Population 2011, UNFPA (2011, 132 pages) Available at: <https://www.unfpa.org/publications/state-world-population-2011>.
UNAIDS, "UNAIDS announces 18.2 million people on antiretroviral therapy, but warns that 15-24 years of age is a highly dangerous time for young women," (2016, 8 pages) Available at: http://www.unaids.org/en/resources/presscentre/pressreleaseandstatementarchive/2016/november/20161121_PRPget-on-the-fast-track.
World Health Organization, "Consolidated guidelines on the use of antiretroviral drugs for treating and preventing HIV infection," (2013, 272 pages) Available at: https://www.who.int/hiv/pub/guidelines/arv2013/download/en/.
Campo et al., "HIV Antiretroviral Drug Resistance" J AIDS Clinc Res. Suppl 5:S5-002 (2012) (4 pages).

(Continued)

*Primary Examiner* — Shanon A. Foley
*Assistant Examiner* — Myron G Hill
(74) *Attorney, Agent, or Firm* — Clark & Elbing LLP

(57) ABSTRACT

In this invention, a non-infectious particle has been produced, comprising a pathogen antigen protein caused to be expressed on the surface of a virus particle having at least one species of paramyxovirus envelope protein missing from the particle. This particle has been found to hold within the particle a large amount of antigen protein compared to an infectious particle, and to be capable of eliciting a host immune response with extremely high efficiency. The non-infectious particle according to the present invention is useful as a vaccine against a pathogenic virus, or the like.

13 Claims, 11 Drawing Sheets
Specification includes a Sequence Listing.

(56) References Cited

OTHER PUBLICATIONS

Carneiro-Proietti et al., "Mother-to-Child Transmission of Human T-Cell Lymphotropic Viruses-1/2: What We Know, and What Are the Gaps in Understanding and Preventing This Route of Infection," J Pediatric Infect Dis Soc. Suppl 1:S24-9 (2014) (6 pages).

Gonçalves et al., "Epidemiology, treatment, and prevention of human T-cell leukemia virus type 1-associated diseases," Clin Microbiol Rev. 23(3):577-89 (2010).

Gross et al., "Molecular Mechanisms of HTLV-1 Cell-to-Cell Transmission," Viruses. 8(3):74 (2016) (22 pages).

Haynes et al., "HIV-Host Interactions: Implications for Vaccine Design," Cell Host Microbe.19(3):292-303 (2016) (12 pages).

Rerks-Ngarm et al., "Vaccination with ALVAC and AIDSVAX to prevent HIV-1 infection in Thailand," N Engl J Med. 361(23):2209-20 (2009).

Satake et al., "Current prevalence of HTLV-1 in Japan as determined by screening of blood donors," J Med Viral. 84(2):327-35 (2012).

Sharp et al., "Origins of HIV and the AIDS pandemic," Cold Spring Harb Perspect Med. 1:a006841 (2011) (22 pages).

Stephenson et al., "New concepts in HIV-1 vaccine development," Curr Opin Immunol. 41:39-46 (2016) (16 pages).

Tsukasaki et al., "Human T-cell lymphotropic virus type I-associated adult T-cell leukemia-lymphoma: new directions in clinical research," Clin Cancer Res. 20(20):5217-25 (2014) (9 pages).

Zhao et al., "Current Advances in Virus-Like Particles as a Vaccination Approach against HIV Infection," Vaccines (Basel). 4(1):2 (2016) (20 pages).

Zwahlen et al., Progression and mortality of untreated HIV-positive individuals living in resource-limited settings: Update of literature review and evidence synthesis. UNAIDS Obligation HQ/05/422204, 2006 (17 pages).

\* cited by examiner

SEQUENCE LISTING

```
<160> NUMBER OF SEQ ID NOS: 29

<210> SEQ ID NO 1
<211> LENGTH: 43
<212> TYPE: DNA
<213> ORGANISM: Artificial Sequence
<220> FEATURE:
<223> OTHER INFORMATION: an artificially synthesized primer sequence

<400> SEQUENCE: 1
atatgcggcc gcgacgccac catgggcaag ttcctggcca ccc                    43

<210> SEQ ID NO 2
<211> LENGTH: 44
<212> TYPE: DNA
<213> ORGANISM: Artificial Sequence
<220> FEATURE:
<223> OTHER INFORMATION: an artificially synthesized primer sequence

<400> SEQUENCE: 2
cgtaatcaca gtctctcttg agttagcttc tctggcccac tggc                   44

<210> SEQ ID NO 3
<211> LENGTH: 44
<212> TYPE: DNA
<213> ORGANISM: Artificial Sequence
<220> FEATURE:
<223> OTHER INFORMATION: an artificially synthesized primer sequence

<400> SEQUENCE: 3
gccagtgggc cagagaagct aactcaagag agactgtgat tacg                   44

<210> SEQ ID NO 4
<211> LENGTH: 66
<212> TYPE: DNA
<213> ORGANISM: Artificial Sequence
<220> FEATURE:
<223> OTHER INFORMATION: an artificially synthesized primer sequence

<400> SEQUENCE: 4
ttagcggccg cgatgaactt tcaccctaag tttttcttac tacggtcatc ttttctcagc  60
cattgc                                                             66

<210> SEQ ID NO 5
<211> LENGTH: 69
<212> TYPE: DNA
<213> ORGANISM: Artificial Sequence
<220> FEATURE:
```

-continued

<223> OTHER INFORMATION: an artificially synthesized primer sequence

<400> SEQUENCE: 5
atatgcggcc gcgatgaact ttcaccctaa gttttctta ctacggtcaa gcttctctgg    60
cccactggc                                                           69

<210> SEQ ID NO 6
<211> LENGTH: 72
<212> TYPE: DNA
<213> ORGANISM: Artificial Sequence
<220> FEATURE:
<223> OTHER INFORMATION: an artificially synthesized primer sequence

<400> SEQUENCE: 6
caacatcact actggttgtt ctcaccacat tggtctcgtg tcaggctagc gcagagaatt    60
tgtgggtaac ag                                                       72

<210> SEQ ID NO 7
<211> LENGTH: 35
<212> TYPE: DNA
<213> ORGANISM: Artificial Sequence
<220> FEATURE:
<223> OTHER INFORMATION: an artificially synthesized primer sequence

<400> SEQUENCE: 7
cacagtctct cttgagttct taatatacca gagcc                              35

<210> SEQ ID NO 8
<211> LENGTH: 35
<212> TYPE: DNA
<213> ORGANISM: Artificial Sequence
<220> FEATURE:
<223> OTHER INFORMATION: an artificially synthesized primer sequence

<400> SEQUENCE: 8
ggctctggta tattaagaac tcaagagaga ctgtg                              35

<210> SEQ ID NO 9
<211> LENGTH: 75
<212> TYPE: DNA
<213> ORGANISM: Artificial Sequence
<220> FEATURE:
<223> OTHER INFORMATION: an artificially synthesized primer sequence

<400> SEQUENCE: 9
taagcggccg ccaaggttca cttatgacag catatatcca gagatcacag tgcatctcaa    60
catcactact ggttg                                                    75

<210> SEQ ID NO 10
<211> LENGTH: 442
<212> TYPE: PRT
<213> ORGANISM: Human T-cell leukemia virus type 1

<400> SEQUENCE: 10

Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
                20                  25                  30

Val Ser Ser Tyr His Ser Lys Pro Cys Asn Pro Ala Gln Pro Val Cys
            35                  40                  45

Ser Trp Thr Leu Asp Leu Leu Ala Leu Ser Ala Asp Gln Ala Leu Gln
        50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
            115                 120                 125

Ser Ser Pro Tyr Trp Lys Phe Gln His Asp Val Asn Phe Thr Gln Glu
130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Thr Pro Leu Leu
                245                 250                 255

Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
        275                 280                 285

Cys His Asn Ser Leu Ile Leu Pro Pro Phe Ser Leu Ser Pro Val Pro
    290                 295                 300

Thr Leu Gly Ser Arg Ser Arg Arg Ala Val Pro Val Ala Val Trp Leu
305                 310                 315                 320

Val Ser Ala Leu Ala Met Gly Ala Gly Val Ala Gly Gly Ile Thr Gly
                325                 330                 335

Ser Met Ser Leu Ala Ser Gly Lys Ser Leu Leu His Glu Val Asp Lys
            340                 345                 350

Asp Ile Ser Gln Leu Thr Gln Ala Ile Val Lys Asn His Lys Asn Leu
        355                 360                 365

Leu Lys Ile Ala Gln Tyr Ala Ala Gln Asn Arg Arg Gly Leu Asp Leu
        370                 375                 380

Leu Phe Trp Glu Gln Gly Gly Leu Cys Lys Ala Leu Gln Glu Gln Cys
385                 390                 395                 400

Arg Phe Pro Asn Ile Thr Asn Ser His Val Pro Ile Leu Gln Glu Arg
            405                 410                 415

Pro Pro Leu Glu Asn Arg Val Leu Thr Gly Trp Gly Leu Asn Trp Asp
            420                 425                 430

Leu Gly Leu Ser Gln Trp Ala Arg Glu Ala
        435                 440

<210> SEQ ID NO 11
<211> LENGTH: 70
<212> TYPE: PRT
<213> ORGANISM: Sendai virus

<400> SEQUENCE: 11

Asn Ser Arg Glu Thr Val Ile Thr Ile Val Val Met Val Ile
1               5                   10                  15

Leu Val Val Ile Ile Val Ile Ile Val Leu Tyr Arg Leu Arg Arg
            20                  25                  30

Ser Met Leu Met Gly Asn Pro Asp Asp Arg Ile Pro Arg Asp Thr Tyr
        35                  40                  45

Thr Leu Glu Pro Lys Ile Arg His Met Tyr Thr Asn Gly Gly Phe Asp
    50                  55                  60

Ala Met Ala Glu Lys Arg
65                  70

<210> SEQ ID NO 12
<211> LENGTH: 1605
<212> TYPE: DNA
<213> ORGANISM: Artificial Sequence
<220> FEATURE:
<223> OTHER INFORMATION: a nucleotide sequence encoding gp63ectoF

<400> SEQUENCE: 12

```
atatgcggcc gcgacgccac catgggcaag ttcctggcca ccctgatcct gttcttccag      60
ttctgccccc tgatcttcgg cgactacagc cccagctgct gcaccctgac catcggcgtg     120
tccagctacc acagcaagcc ctgcaacccc gccagcccg tgtgcagctg acactggat      180
ctgctggccc tgagcgccga ccaggccctg cagcctcctt gccccaacct ggtgtcctac     240
agcagctacc acgccaccta cagcctgtac ctgttcccc actggaccaa gaagcccaac     300
cggaacggcg gaggctacta cagcgcctcc tacagcgacc cctgctccct gaagtgcccc     360
tacctgggct gccagagctg gacctgcccc tacacaggcg ccgtgtccag ccctactgg     420
aagttccagc acgacgtgaa cttcacccaa gaagtgtccc ggctgaacat caacctgcac     480
ttcagcaagt gcggcttccc cttctcccctg ctggtggacg ccctggcta cgacccatc     540
tggttcctga acaccgagcc cagccagctg ccccctactg ctcctcctct gctgcccac     600
tccaacctgg accatatcct ggaacccagc atcccctgga agtccaagct gctgacactg     660
gtgcagctga ccctgcagag caccaactac acctgtatcg tgtgcatcga ccgggccagc     720
ctgagcacct ggcacgtgct gtacagcccc aacgtgtccg tgcccagcag cagctccacc     780
cccctgctgt accctagtct ggccctgcct gcccccacc tgacactgcc cttcaactgg     840
acccactgct cgaccccca gatccaggcc atcgtgtcta gcccctgcca acagcctg      900
atcctgcccc ccttcagcct gtcccctgtg cccaccctgg gctccagatc tagaagggcc     960
gtgcccgtgg ccgtgtggct ggtgtctgct ctggctatgg agccggcgt ggccggtggc    1020
atcacaggca gcatgagcct ggcctccggc aagagcctgc tgcacgaggt ggacaaggac    1080
atcagccagc tgacccaggc cattgtgaag aaccacaaga acctgctgaa gatcgcccag    1140
tacgccgccc agaacagacg gggcctggac ctgctgtttt gggagcaggg cggcctgtgc    1200
aaagccctgc aagaacagtg ccggttcccc aacatcacca cagccacgt gcccatcctg    1260
caagaaagac ccccctgga aaccgggtg ctgaccggct ggggcctgaa ctgggatctg    1320
ggcctgagcc agtgggccag agaagctaac tcaagagaga ctgtgattac gatcatagta    1380
gttatggtcg taatattggt ggtcattata gtgatcatca tcgtgcttta tagactcaga    1440
aggtcaatgc taatgggtaa tccagatgac cgtataccga gggacacata cacattagag    1500
ccgaagatca gacatatgta cacaaacggt gggtttgatg caatggctga gaaaagatga    1560
```
ccgtagtaag aaaaacttag ggtgaaagtt catcgcggcc gctaa 1605

<210> SEQ ID NO 13
<211> LENGTH: 512
<212> TYPE: PRT
<213> ORGANISM: Artificial Sequence
<220> FEATURE:
<223> OTHER INFORMATION: amino acid sequence of gp63ectoF

<400> SEQUENCE: 13

```
Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln His Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Thr Pro Leu Leu
                245                 250                 255

Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
        275                 280                 285

Cys His Asn Ser Leu Ile Leu Pro Pro Phe Ser Leu Ser Pro Val Pro
    290                 295                 300

Thr Leu Gly Ser Arg Ser Arg Arg Ala Val Pro Val Ala Val Trp Leu
305                 310                 315                 320

Val Ser Ala Leu Ala Met Gly Ala Gly Val Ala Gly Gly Ile Thr Gly
                325                 330                 335

Ser Met Ser Leu Ala Ser Gly Lys Ser Leu Leu His Glu Val Asp Lys
            340                 345                 350

Asp Ile Ser Gln Leu Thr Gln Ala Ile Val Lys Asn His Lys Asn Leu
```

```
            355                 360                 365
Leu Lys Ile Ala Gln Tyr Ala Ala Gln Asn Arg Arg Gly Leu Asp Leu
    370                 375                 380
Leu Phe Trp Glu Gln Gly Gly Leu Cys Lys Ala Leu Gln Glu Gln Cys
385                 390                 395                 400
Arg Phe Pro Asn Ile Thr Asn Ser His Val Pro Ile Leu Gln Glu Arg
                405                 410                 415
Pro Pro Leu Glu Asn Arg Val Leu Thr Gly Trp Gly Leu Asn Trp Asp
            420                 425                 430
Leu Gly Leu Ser Gln Trp Ala Arg Glu Ala Asn Ser Arg Glu Thr Val
        435                 440                 445
Ile Thr Ile Ile Val Val Met Val Val Ile Leu Val Val Ile Ile Val
    450                 455                 460
Ile Ile Ile Val Leu Tyr Arg Leu Arg Arg Ser Met Leu Met Gly Asn
465                 470                 475                 480
Pro Asp Asp Arg Ile Pro Arg Asp Thr Tyr Thr Leu Glu Pro Lys Ile
                485                 490                 495
Arg His Met Tyr Thr Asn Gly Gly Phe Asp Ala Met Ala Glu Lys Arg
            500                 505                 510

<210> SEQ ID NO 14
<211> LENGTH: 651
<212> TYPE: PRT
<213> ORGANISM: Human immunodeficiency virus type 1

<400> SEQUENCE: 14

Ala Glu Asn Leu Trp Val Thr Val Tyr Gly Val Pro Val Trp Lys
1               5                   10                  15
Asp Ala Glu Thr Thr Leu Phe Cys Ala Ser Asp Ala Lys Ala Tyr Glu
                20                  25                  30
Thr Glu Lys His Asn Val Trp Ala Thr His Ala Cys Val Pro Thr Asp
            35                  40                  45
Pro Asn Pro Gln Glu Ile His Leu Glu Asn Val Thr Glu Glu Phe Asn
        50                  55                  60
Met Trp Lys Asn Asn Met Val Glu Gln Met His Thr Asp Ile Ile Ser
65                  70                  75                  80
Leu Trp Asp Gln Ser Leu Lys Pro Cys Val Lys Leu Thr Pro Leu Cys
                85                  90                  95
Val Thr Leu Gln Cys Thr Asn Val Thr Asn Asn Ile Thr Asp Asp Met
            100                 105                 110
Arg Gly Glu Leu Lys Asn Cys Ser Phe Asn Met Thr Thr Glu Leu Arg
        115                 120                 125
Asp Lys Lys Gln Lys Val Tyr Ser Leu Phe Tyr Arg Leu Asp Val Val
    130                 135                 140
Gln Ile Asn Glu Asn Gln Gly Asn Arg Ser Asn Asn Ser Asn Lys Glu
145                 150                 155                 160
Tyr Arg Leu Ile Asn Cys Asn Thr Ser Ala Ile Thr Gln Ala Cys Pro
                165                 170                 175
Lys Val Ser Phe Glu Pro Ile Pro Ile His Tyr Cys Ala Pro Ala Gly
            180                 185                 190
Phe Ala Ile Leu Lys Cys Lys Asp Lys Lys Phe Asn Gly Thr Gly Pro
        195                 200                 205
Cys Pro Ser Val Ser Thr Val Gln Cys Thr His Gly Ile Lys Pro Val
    210                 215                 220
```

```
Val Ser Thr Gln Leu Leu Asn Gly Ser Leu Ala Glu Glu Val
225                 230                 235                 240

Met Ile Arg Ser Glu Asn Ile Thr Asn Asn Ala Lys Asn Ile Leu Val
        245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Thr Val Ser Lys
        290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
            325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
        370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
            405                 410                 415

Ile Thr Gly Leu Ile Leu Thr Arg Asp Gly Gly Ser Thr Asn Ser Thr
        420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
        450                 455                 460

Ala Pro Thr Arg Ala Lys Arg Arg Val Val Gly Arg Glu Lys Arg Ala
465                 470                 475                 480

Val Gly Ile Gly Ala Val Phe Leu Gly Phe Leu Gly Ala Ala Gly Ser
            485                 490                 495

Thr Met Gly Ala Ala Ser Met Thr Leu Thr Val Gln Ala Arg Asn Leu
            500                 505                 510

Leu Ser Gly Ile Val Gln Gln Ser Asn Leu Leu Arg Ala Ile Glu
            515                 520                 525

Ala Gln Gln His Leu Leu Lys Leu Thr Val Trp Gly Ile Lys Gln Leu
530                 535                 540

Gln Ala Arg Val Leu Ala Val Glu Arg Tyr Leu Arg Asp Gln Gln Leu
545                 550                 555                 560

Leu Gly Ile Trp Gly Cys Ser Gly Lys Leu Ile Cys Thr Thr Asn Val
            565                 570                 575

Pro Trp Asn Ser Ser Trp Ser Asn Arg Asn Leu Ser Glu Ile Trp Asp
            580                 585                 590

Asn Met Thr Trp Leu Gln Trp Asp Lys Glu Ile Ser Asn Tyr Thr Gln
            595                 600                 605

Ile Ile Tyr Gly Leu Leu Glu Glu Ser Gln Asn Gln Gln Glu Lys Asn
            610                 615                 620

Glu Gln Asp Leu Leu Ala Leu Asp Lys Trp Ala Ser Leu Trp Asn Trp
625                 630                 635                 640

Phe Asp Ile Ser Asn Trp Leu Trp Tyr Ile Lys
```

<210> SEQ ID NO 15
<211> LENGTH: 26
<212> TYPE: PRT
<213> ORGANISM: Sendai virus

<400> SEQUENCE: 15

Met Thr Ala Tyr Ile Gln Arg Ser Gln Cys Ile Ser Thr Ser Leu Leu
1               5                   10                  15

Val Val Leu Thr Thr Leu Val Ser Cys Gln
            20                  25

<210> SEQ ID NO 16
<211> LENGTH: 2318
<212> TYPE: DNA
<213> ORGANISM: Artificial Sequence
<220> FEATURE:
<223> OTHER INFORMATION: a nucleotide sequence encoding sfEnvF

<400> SEQUENCE: 16

```
taagcggccg ccaaggttca cttatgacag catatatcca gagatcacag tgcatctcaa      60
catcactact ggttgttctc accacattgg tctcgtgtca ggctagcgca gagaatttgt     120
gggtaacagt ctactatgga gtccctgtat ggaaggatgc agagacaaca ttgttctgtg     180
ctagtgacgc aaaggcttac gagacggaga agcacaatgt gtgggcaact cacgcatgtg     240
tcccaaccga tccaaatcct caagagattc atctagagaa tgtgactgaa gaattcaata     300
tgtggaagaa taatatggta gagcaaatgc atacagatat cattagttta tgggaccagt     360
cacttaaacc ctgcgttaaa ttgacgcctc tatgtgtgac acttcaatgt actaatgtta     420
caaacaacat aacagatgat atgagaggag aactgaagaa ctgtagtttc aacatgacga     480
cagagttgcg tgacaagaaa cagaaagtgt attcactatt ctatcggttg gatgtagtac     540
agataaatga aatcaaggga acaggtccaa caactctaa caaagagtac agacttatta     600
attgcaatac cagtgctatc acgcaagcct gcccaaaggt ttcatttgaa ccaataccta     660
ttcattattg tgcacctgct ggattcgcca tcctcaaatg taaagacaag aagttcaatg     720
gaacaggacc ctgcccatca gtttcaaccg ttcagtgcac ccacggaatc aagcctgtag     780
ttagtactca attattgtta aatgggagct agctgaaga agaagttatg attagatcag     840
agaatattac caataatgcg aagaacatct tggttcaatt caatactcca gtccagatca     900
attgcacaag gcctaataat aataccagaa agagtataag aattgggcca ggacaggcat     960
tctatgcaac aggagatata atcggagaca ttcgacaagc gcactgcact gtttctaagg    1020
ccacttggaa tgaaacattg gtaaagttg taaagcaact tcggaagcat ttcggaaata    1080
acacaattat tagatttgcg aactcatctg gaggggatct ggaagtgaca acacactctt    1140
tcaattgcgg tggcgagttc ttctattgta atacaagtgg attatttaac tctacttgga    1200
tttcaaatac ctcagtccaa ggatctaatt caacagggtc taacgattct ataacattac    1260
cttgccgtat aaagcaaatt attaatatgt ggcaaagaat cgggcaagcg atgtatgctc    1320
cacctattca aggcgtgatt cgttgcgttt caaacataac agggttgatc ctgaccaggg    1380
atggaggctc taccaattcc accaccgaga ccttccgtcc cggtggcgga gatatgcggg    1440
ataactggag atcagagctc tataagtata aggttgtgaa gattgaacct cttggagttg    1500
cccctacaag agcaaagaga agggtggttg gccgagagaa gagagcagtt ggcatcggtg    1560
ctgtctttct cggattctt ggagcagctg gatccactat gggagcagca tcaatgacac    1620
```

-continued

```
taacagtgca ggctagaaat ttgcttagcg gaatcgttca gcagcagagc aatttactaa   1680
gagcaattga agcacagcaa catctcttaa agttgacggt gtggggcatt aaacaactac   1740
aagcgagagt gcttgccgtc gaaagatatt tgcgagacca acagctattg ggtatttggg   1800
gttgttctgg gaaattaatt tgcacaacaa atgttccatg gaactcctcc tggagtaata   1860
ggaatttaag tgagatatgg gacaacatga catggttgca gtgggacaag gaaatctcaa   1920
attatacaca gataatctat ggattattag aagagtctca gaatcagcaa gagaagaatg   1980
aacaggattt gcttgcattg ataagtgggc cttctctatg gaactggttc gatattagta   2040
attggctctg gtatattaag aactcaagag agactgtgat tacgatcata gtagttatgg   2100
tcgtaatatt ggtggtcatt atagtgatca tcatcgtgct ttatagactc agaaggtcaa   2160
tgctaatggg taatccagat gaccgtatac cgagggacac atacacatta gagccgaaga   2220
tcagacatat gtacacaaac ggtgggtttg atgcaatggc tgagaaaaga tgaccgtagt   2280
aagaaaaact tagggtgaaa gttcatcgcg ccgctaa                            2318
```

<210> SEQ ID NO 17
<211> LENGTH: 749
<212> TYPE: PRT
<213> ORGANISM: Artificial Sequence
<220> FEATURE:
<223> OTHER INFORMATION: amino acid sequence of sfEnvF

<400> SEQUENCE: 17

```
Met Thr Ala Tyr Ile Gln Arg Ser Gln Cys Ile Ser Thr Ser Leu Leu
1               5                   10                  15

Val Val Leu Thr Thr Leu Val Ser Cys Gln Ala Ser Ala Glu Asn Leu
            20                  25                  30

Trp Val Thr Val Tyr Tyr Gly Val Pro Val Trp Lys Asp Ala Glu Thr
        35                  40                  45

Thr Leu Phe Cys Ala Ser Asp Ala Lys Ala Tyr Glu Thr Glu Lys His
    50                  55                  60

Asn Val Trp Ala Thr His Ala Cys Val Pro Thr Asp Pro Asn Pro Gln
65                  70                  75                  80

Glu Ile His Leu Glu Asn Val Thr Glu Glu Phe Asn Met Trp Lys Asn
                85                  90                  95

Asn Met Val Glu Gln Met His Thr Asp Ile Ile Ser Leu Trp Asp Gln
            100                 105                 110

Ser Leu Lys Pro Cys Val Lys Leu Thr Pro Leu Cys Val Thr Leu Gln
        115                 120                 125

Cys Thr Asn Val Thr Asn Asn Ile Thr Asp Asp Met Arg Gly Glu Leu
    130                 135                 140

Lys Asn Cys Ser Phe Asn Met Thr Thr Glu Leu Arg Asp Lys Lys Gln
145                 150                 155                 160

Lys Val Tyr Ser Leu Phe Tyr Arg Leu Asp Val Val Gln Ile Asn Glu
                165                 170                 175

Asn Gln Gly Asn Arg Ser Asn Asn Ser Asn Lys Glu Tyr Arg Leu Ile
            180                 185                 190

Asn Cys Asn Thr Ser Ala Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Lys Asp Lys Lys Phe Asn Gly Thr Gly Pro Cys Pro Ser Val
225                 230                 235                 240
```

```
Ser Thr Val Gln Cys Thr His Gly Ile Lys Pro Val Ser Thr Gln
            245                 250                 255

Leu Leu Leu Asn Gly Ser Leu Ala Glu Glu Val Met Ile Arg Ser
            260                 265                 270

Glu Asn Ile Thr Asn Asn Ala Lys Asn Ile Leu Val Gln Phe Asn Thr
            275                 280                 285

Pro Val Gln Ile Asn Cys Thr Arg Pro Asn Asn Thr Arg Lys Ser
            290                 295                 300

Ile Arg Ile Gly Pro Gly Gln Ala Phe Tyr Ala Thr Gly Asp Ile Ile
305                 310                 315                 320

Gly Asp Ile Arg Gln Ala His Cys Thr Val Ser Lys Ala Thr Trp Asn
                    325                 330                 335

Glu Thr Leu Gly Lys Val Val Lys Gln Leu Arg Lys His Phe Gly Asn
                340                 345                 350

Asn Thr Ile Ile Arg Phe Ala Asn Ser Ser Gly Gly Asp Leu Glu Val
                355                 360                 365

Thr Thr His Ser Phe Asn Cys Gly Gly Glu Phe Phe Tyr Cys Asn Thr
370                 375                 380

Ser Gly Leu Phe Asn Ser Thr Trp Ile Ser Asn Thr Ser Val Gln Gly
385                 390                 395                 400

Ser Asn Ser Thr Gly Ser Asn Asp Ser Ile Thr Leu Pro Cys Arg Ile
                405                 410                 415

Lys Gln Ile Ile Asn Met Trp Gln Arg Ile Gly Gln Ala Met Tyr Ala
                420                 425                 430

Pro Pro Ile Gln Gly Val Ile Arg Cys Val Ser Asn Ile Thr Gly Leu
                435                 440                 445

Ile Leu Thr Arg Asp Gly Gly Ser Thr Asn Ser Thr Thr Glu Thr Phe
450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Arg
                485                 490                 495

Ala Lys Arg Arg Val Val Gly Arg Glu Lys Arg Ala Val Gly Ile Gly
                500                 505                 510

Ala Val Phe Leu Gly Phe Leu Gly Ala Ala Gly Ser Thr Met Gly Ala
                515                 520                 525

Ala Ser Met Thr Leu Thr Val Gln Ala Arg Asn Leu Leu Ser Gly Ile
                530                 535                 540

Val Gln Gln Gln Ser Asn Leu Leu Arg Ala Ile Glu Ala Gln Gln His
545                 550                 555                 560

Leu Leu Lys Leu Thr Val Trp Gly Ile Lys Gln Leu Gln Ala Arg Val
                565                 570                 575

Leu Ala Val Glu Arg Tyr Leu Arg Asp Gln Gln Leu Leu Gly Ile Trp
                580                 585                 590

Gly Cys Ser Gly Lys Leu Ile Cys Thr Thr Asn Val Pro Trp Asn Ser
                595                 600                 605

Ser Trp Ser Asn Arg Asn Leu Ser Glu Ile Trp Asp Asn Met Thr Trp
                610                 615                 620

Leu Gln Trp Asp Lys Glu Ile Ser Asn Tyr Thr Gln Ile Ile Tyr Gly
625                 630                 635                 640

Leu Leu Glu Glu Ser Gln Asn Gln Gln Glu Lys Asn Glu Gln Asp Leu
                645                 650                 655
```

-continued

```
Leu Ala Leu Asp Lys Trp Ala Ser Leu Trp Asn Trp Phe Asp Ile Ser
            660                 665                 670

Asn Trp Leu Trp Tyr Ile Lys Asn Ser Arg Glu Thr Val Ile Thr Ile
            675                 680                 685

Ile Val Val Met Val Val Ile Leu Val Val Ile Ile Val Ile Ile Ile
            690                 695                 700

Val Leu Tyr Arg Leu Arg Arg Ser Met Leu Met Gly Asn Pro Asp Asp
705                 710                 715                 720

Arg Ile Pro Arg Asp Thr Tyr Thr Leu Glu Pro Lys Ile Arg His Met
                725                 730                 735

Tyr Thr Asn Gly Gly Phe Asp Ala Met Ala Glu Lys Arg
            740                 745
```

<210> SEQ ID NO 18
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 18
ggctagcgca gagaatttgt gggtcacag                                    29

<210> SEQ ID NO 19
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 19
tattgaaaga gcagttcttt atttctcctc                                   30

<210> SEQ ID NO 20
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 20
gaggagaaat aaagaactgc tctttcaata                                   30

<210> SEQ ID NO 21
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 21
ctgtactatt atgttctttg tattgtctg                                    29

<210> SEQ ID NO 22
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 22
cagacaatac aaagaacata atagtacag                                    29

<210> SEQ ID NO 23
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 23
ctctcttgag ttctttatat accacagcc                                      29

<210> SEQ ID NO 24
<211> LENGTH: 41
<212> TYPE: DNA
<213> ORGANISM: Artificial Sequence
<220> FEATURE:
<223> OTHER INFORMATION: an artificially synthesized primer sequence

<400> SEQUENCE: 24
atatgcggcc gcgacgccac catgacagca tatatccaga g                        41

<210> SEQ ID NO 25
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 25
cccacaaatt ctctgcgcta gcctgacacg                                     30

<210> SEQ ID NO 26
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 26
tataaagaac tcaagagaga ctgtgattac                                     30

<210> SEQ ID NO 27
<211> LENGTH: 35
<212> TYPE: DNA
<213> ORGANISM: Artificial Sequence
<220> FEATURE:
<223> OTHER INFORMATION: an artificially synthesized primer sequence

<400> SEQUENCE: 27
ctgcggccgc gatgaacttt caccctaagt ttttc                               35

<210> SEQ ID NO 28
<211> LENGTH: 646
<212> TYPE: PRT
<213> ORGANISM: Simian-Human immunodeficiency virus

<400> SEQUENCE: 28

Asn Leu Trp Val Thr Val Tyr Gly Val Pro Val Trp Lys Glu Ala
1               5                   10                  15

Thr Thr Thr Leu Phe Cys Ala Ser Asp Ala Lys Ala Tyr Asp Thr Glu
                20                  25                  30

Val His Asn Val Trp Ala Thr His Ala Cys Val Pro Thr Asp Pro Asn
            35                  40                  45

Pro Gln Glu Val Val Leu Glu Asn Val Thr Glu Asn Phe Asn Met Trp
        50                  55                  60

-continued

```
Lys Asn Asn Met Val Glu Gln Met His Glu Asp Ile Ile Ser Leu Trp
 65                  70                  75                  80

Asp Gln Ser Leu Lys Pro Cys Val Lys Leu Thr Pro Leu Cys Val Thr
                 85                  90                  95

Leu Asn Cys Thr Asp Trp Gly Asn Val Thr Asn Ile Asn Ser Ser Ser
            100                 105                 110

Glu Glu Met Arg Gly Glu Ile Lys Asn Cys Ser Phe Asn Ile Thr Thr
        115                 120                 125

Ser Ile Arg Asp Lys Val Lys Glu Asp Tyr Ala Leu Phe Tyr Arg Leu
    130                 135                 140

Asp Val Pro Ile Asp Asn Asp Asn Thr Ser Tyr Arg Leu Ile Ser
145                 150                 155                 160

Cys Asn Thr Ser Thr Ile Thr Gln Ala Cys Pro Lys Val Ser Phe Glu
            165                 170                 175

Pro Ile Pro Ile His Tyr Cys Thr Pro Ala Gly Phe Ala Ile Leu Lys
        180                 185                 190

Cys Lys Asp Lys Lys Phe Asn Gly Thr Gly Pro Cys Lys Asn Val Ser
    195                 200                 205

Thr Val Gln Cys Thr His Gly Ile Arg Pro Val Val Ser Thr Gln Leu
    210                 215                 220

Leu Leu Asn Gly Ser Leu Ala Glu Glu Val Val Ile Arg Ser Ser
225                 230                 235                 240

Asn Phe Thr Asp Asn Thr Lys Asn Ile Ile Val Gln Leu Lys Glu Ser
                245                 250                 255

Val Glu Ile Asn Cys Thr Arg Pro Asn Asn Thr Arg Lys Ser Ile
        260                 265                 270

His Ile Gly Pro Gly Arg Ala Phe Tyr Thr Thr Gly Asp Ile Ile Gly
    275                 280                 285

Asp Ile Arg Gln Ala His Cys Asn Ile Ser Arg Thr Lys Trp Asn Asn
290                 295                 300

Thr Leu Asn Gln Ile Ala Thr Lys Leu Lys Glu Gln Phe Gly Asn Asn
305                 310                 315                 320

Lys Thr Ile Val Phe Asn Gln Ser Ser Gly Gly Asp Pro Glu Ile Val
                325                 330                 335

Met His Ser Phe Asn Cys Gly Gly Glu Phe Phe Tyr Cys Asn Ser Thr
            340                 345                 350

Gln Leu Phe Asn Ser Thr Trp Asn Phe Asn Gly Thr Trp Asn Leu Thr
        355                 360                 365

Gln Ser Asn Gly Thr Asp Thr Ile Thr Leu Pro Cys Arg Ile Lys Gln
    370                 375                 380

Ile Ile Asn Met Trp Gln Glu Val Gly Lys Ala Met Tyr Ala Pro Pro
385                 390                 395                 400

Ile Arg Gly Gln Ile Arg Cys Ser Ser Asn Ile Thr Gly Leu Ile Leu
                405                 410                 415

Thr Arg Asp Gly Gly Asn His Asn Asn Asp Thr Glu Thr Phe Arg Pro
            420                 425                 430

Gly Gly Gly Asp Met Arg Asp Asn Trp Arg Ser Glu Leu Tyr Lys Tyr
        435                 440                 445

Lys Val Val Lys Ile Glu Pro Leu Gly Val Ala Pro Thr Lys Ala Lys
    450                 455                 460

Arg Arg Val Val Gln Arg Glu Lys Arg Ala Val Gly Ala Ile Gly Ala
465                 470                 475                 480

Met Phe Leu Gly Phe Leu Gly Ala Ala Gly Ser Thr Met Gly Ala Ala
```

```
                485                 490                 495
Ser Ile Thr Leu Thr Val Gln Ala Arg Leu Leu Ser Gly Ile Val
            500                 505                 510

Gln Gln Gln Asn Asn Leu Leu Lys Ala Ile Glu Ala Gln Gln His Leu
        515                 520                 525

Leu Gln Leu Thr Val Trp Gly Ile Lys Gln Leu Gln Ala Arg Val Leu
    530                 535                 540

Ala Val Glu Arg Tyr Leu Arg Asp Gln Gln Leu Leu Gly Ile Trp Gly
545                 550                 555                 560

Cys Ser Gly Lys Leu Ile Cys Thr Thr Ala Val Pro Trp Asn Ala Ser
                565                 570                 575

Trp Ser Asn Lys Thr Leu Asp Met Ile Trp Asn Asn Met Thr Trp Met
            580                 585                 590

Glu Trp Glu Arg Glu Ile Asp Asn Tyr Thr Gly Leu Ile Tyr Thr Leu
        595                 600                 605

Ile Glu Glu Ser Gln Asn Gln Gln Glu Lys Asn Glu Gln Glu Leu Leu
    610                 615                 620

Glu Leu Asp Lys Trp Ala Ser Leu Trp Asn Trp Phe Asp Ile Thr Asn
625                 630                 635                 640

Trp Leu Trp Tyr Ile Lys
                645

<210> SEQ ID NO 29
<211> LENGTH: 746
<212> TYPE: PRT
<213> ORGANISM: Artificial Sequence
<220> FEATURE:
<223> OTHER INFORMATION: amino acid sequence of sfAD8EOEnvF

<400> SEQUENCE: 29

Met Thr Ala Tyr Ile Gln Arg Ser Gln Cys Ile Ser Thr Ser Leu Leu
1               5                   10                  15

Val Val Leu Thr Thr Leu Val Ser Cys Gln Ala Ser Ala Glu Asn Leu
            20                  25                  30

Trp Val Thr Val Tyr Tyr Gly Val Pro Val Trp Lys Glu Ala Thr Thr
        35                  40                  45

Thr Leu Phe Cys Ala Ser Asp Ala Lys Ala Tyr Asp Thr Glu Val His
    50                  55                  60

Asn Val Trp Ala Thr His Ala Cys Val Pro Thr Asp Pro Asn Pro Gln
65                  70                  75                  80

Glu Val Val Leu Glu Asn Val Thr Glu Asn Phe Asn Met Trp Lys Asn
                85                  90                  95

Asn Met Val Glu Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asp Trp Gly Asn Val Thr Asn Ile Asn Ser Ser Ser Glu Glu
    130                 135                 140

Met Arg Gly Glu Ile Lys Asn Cys Ser Phe Asn Ile Thr Thr Ser Ile
145                 150                 155                 160

Arg Asp Lys Val Lys Glu Asp Tyr Ala Leu Phe Tyr Arg Leu Asp Val
                165                 170                 175

Val Pro Ile Asp Asn Asp Asn Thr Ser Tyr Arg Leu Ile Ser Cys Asn
            180                 185                 190

Thr Ser Thr Ile Thr Gln Ala Cys Pro Lys Val Ser Phe Glu Pro Ile
```

```
            195                 200                 205
Pro Ile His Tyr Cys Thr Pro Ala Gly Phe Ala Ile Leu Lys Cys Lys
210                 215                 220

Asp Lys Lys Phe Asn Gly Thr Gly Pro Cys Lys Asn Val Ser Thr Val
225                 230                 235                 240

Gln Cys Thr His Gly Ile Arg Pro Val Val Ser Thr Gln Leu Leu Leu
                    245                 250                 255

Asn Gly Ser Leu Ala Glu Glu Val Val Ile Arg Ser Ser Asn Phe
            260                 265                 270

Thr Asp Asn Thr Lys Asn Ile Ile Val Gln Leu Lys Glu Ser Val Glu
                275                 280                 285

Ile Asn Cys Thr Arg Pro Asn Asn Asn Thr Arg Lys Ser Ile His Ile
290                 295                 300

Gly Pro Gly Arg Ala Phe Tyr Thr Thr Gly Asp Ile Ile Gly Asp Ile
305                 310                 315                 320

Arg Gln Ala His Cys Asn Ile Ser Arg Thr Lys Trp Asn Asn Thr Leu
                    325                 330                 335

Asn Gln Ile Ala Thr Lys Leu Lys Glu Gln Phe Gly Asn Asn Lys Thr
            340                 345                 350

Ile Val Phe Asn Gln Ser Ser Gly Gly Asp Pro Glu Ile Val Met His
                355                 360                 365

Ser Phe Asn Cys Gly Gly Glu Phe Phe Tyr Cys Asn Ser Thr Gln Leu
370                 375                 380

Phe Asn Ser Thr Trp Asn Phe Asn Gly Thr Trp Asn Leu Thr Gln Ser
385                 390                 395                 400

Asn Gly Thr Asp Thr Ile Thr Leu Pro Cys Arg Ile Lys Gln Ile Ile
                    405                 410                 415

Asn Met Trp Gln Glu Val Gly Lys Ala Met Tyr Ala Pro Pro Ile Arg
            420                 425                 430

Gly Gln Ile Arg Cys Ser Ser Asn Ile Thr Gly Leu Ile Leu Thr Arg
                435                 440                 445

Asp Gly Gly Asn His Asn Asn Asp Thr Glu Thr Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                    485                 490                 495

Val Val Gln Arg Glu Lys Arg Ala Val Gly Ala Ile Gly Ala Met Phe
            500                 505                 510

Leu Gly Phe Leu Gly Ala Ala Gly Ser Thr Met Gly Ala Ala Ser Ile
                515                 520                 525

Thr Leu Thr Val Gln Ala Arg Leu Leu Leu Ser Gly Ile Val Gln Gln
530                 535                 540

Gln Asn Asn Leu Leu Lys Ala Ile Glu Ala Gln Gln His Leu Leu Gln
545                 550                 555                 560

Leu Thr Val Trp Gly Ile Lys Gln Leu Gln Ala Arg Val Leu Ala Val
                    565                 570                 575

Glu Arg Tyr Leu Arg Asp Gln Gln Leu Leu Gly Ile Trp Gly Cys Ser
            580                 585                 590

Gly Lys Leu Ile Cys Thr Thr Ala Val Pro Trp Asn Ala Ser Trp Ser
                595                 600                 605

Asn Lys Thr Leu Asp Met Ile Trp Asn Asn Met Thr Trp Met Glu Trp
610                 615                 620
```

-continued

```
Glu Arg Glu Ile Asp Asn Tyr Thr Gly Leu Ile Tyr Thr Leu Ile Glu
625                 630                 635                 640

Glu Ser Gln Asn Gln Gln Glu Lys Asn Glu Gln Glu Leu Leu Glu Leu
                645                 650                 655

Asp Lys Trp Ala Ser Leu Trp Asn Trp Phe Asp Ile Thr Asn Trp Leu
            660                 665                 670

Trp Tyr Ile Lys Asn Ser Arg Glu Thr Val Ile Thr Ile Ile Val Val
        675                 680                 685

Met Val Val Ile Leu Val Val Ile Ile Val Ile Ile Ile Val Leu Tyr
    690                 695                 700

Arg Leu Arg Arg Ser Met Leu Met Gly Asn Pro Asp Asp Arg Ile Pro
705                 710                 715                 720

Arg Asp Thr Tyr Thr Leu Glu Pro Lys Ile Arg His Met Tyr Thr Asn
                725                 730                 735

Gly Gly Phe Asp Ala Met Ala Glu Lys Arg
            740                 745
```

INFECTIOUS DISEASE VACCINE USING NON-INFECTIOUS PARAMYXOVIRUS PARTICLE

TECHNICAL FIELD

The present invention relates to an infectious disease vaccine using a non-infectious paramyxovirus particle carrying an antigen protein on the envelope, a method for producing the vaccine, a protection method against infection by use of the vaccine, and the like.

BACKGROUND ART

It is an internationally important issue to suppress expansion of infectious diseases (WHO World Health Statistics 2016 (Non-Patent Document 1)). In particular, infectious diseases due to enveloped viruses (viruses covered with a lipid bilayer membrane derived from cell membrane) including acquired immunodeficiency syndrome (AIDS) induced by human immunodeficiency virus (HIV-1) as a causative virus and Adult T-cell leukemia/lymphoma (ATL) induced by T-cell leukemia virus 1 (HTLV-1) as a cause are viral infectious diseases against which countermeasures are desired most. Further, as countermeasures against infectious diseases by pathogen including these, widespread use of vaccines plays a crucial role, and development of an antibody-inducing vaccine has become a key strategy.

AIDS is a disease that is induced by infection of HIV-1 belonging to lentivirus of Retroviridae and is characterized by critical systemic immunodeficiency. AIDS has become one of the most serious medical issues which human beings are facing currently, because of a high incidence and mortality after infection and difficulty in prevention and treatment. HIV infects and destroys CD4 positive helper T cells and macrophages, which are cells controlling acquired immunity. Thus, a systemic immunodeficiency state is induced by a significant functional decline of acquired immunity, which leads to pathogenesis of various opportunistic infections and various and critical systemic symptoms such as opportunistic tumor and central nervous system damage. If a suitable treatment is not carried out, the survival period after pathogenesis is estimated to be from 6 to 19 months (UNAIDS Obligation HQ/05/422204, 2006 (Non-Patent Document 2)).

AIDS as an infectious disease was reported first in the United States in 1981, but it is estimated that an epidemic of AIDS started in Central African regions before 1981 (Sharp P M and Hahn B H, Cold Spring Harb Perspectives in Medicine 1(1): a006841, 2011 (Non-Patent Document 3)). Then, epidemic regions outspread to the entire world after the 1980s, and a fast and furious epidemic of HIV occurred in various regions such as Eastern Europe and China in the 1990s.

In the estimation of Joint United Nations Programme on HIV/AIDS (UNAIDS), the number of HIV-1 infected patients, the number of newly infected patients per year, and the number of fatalities per year in the world as of 2014 are estimated to be 37,000,000, 2,100,000, and 1,100,000, respectively, and those numbers continue to increase at this moment. This means that one person among about 200 persons of the estimated total population in the world ("The State of the World Population," published in 2011 (Non-Patent Document 4)) is infected with AIDS, and 5,700 persons a day, that is, one newly infected patient occurs per 15 seconds. In particular, 25,000,000 or more patients are concentrated in Africa. In some countries in Africa, the life expectancy fell from 60 to 40 due to the epidemic of AIDS, which causes serious social and economic problems that determine one country's existence or non-existence. In addition, it is estimated that there are 5,100,000 infected patients in Asia-Pacific regions centered in China and there are also 2,400,000 infected patients in Europe and the United States (UNAIDS Fact Sheet 2016 (Non-Patent Document 5)).

The AIDS treatment has made rapid progress in recent years, and in addition to a reverse transcriptase inhibitor (RTI) typified by azidothymidine (AZT), an excellent protease inhibitor (PI) has been developed. In recent years, an integrase inhibitor (INI) or the like has been in practical use. As a result, AIDS pathogenesis can be inhibited by virus replication control in an infected patient with an anti-HIV therapy (antiretroviral therapy, ART) obtained by a combination of those plural drugs each having a different action mechanism (Consolidated guidelines on the use of antiretroviral drugs for treating and preventing. HIV infection: recommendations for a public health approach June 2013, WHO (Non-Patent Document 6)). Owing to the introduction of the ART, the frequency of opportunistic infection and the number of fatalities due to AIDS in developed countries decreased by 40% since 1995.

However, it is known that the ART is nothing of the radical treatment, the virus is not expelled but remains in lymph nodes, central nervous system, and the like (latent reservoir), and once the medication is stopped, re-growth of the virus occurs immediately. For this reason, it is necessary for an infected patient to continue drug administration for his or her life in order to prevent pathogenesis of AIDS, but patient's adherence to drugs (adherence to drug administration schedule) is not easy in view of problems such as side effects and drug administration conditions. Furthermore, from a problem of occurrence of resistant AIDS virus, the decrease in the number of fatalities that went down by half every year in the United States has been peaked out (Campo J E et al., AIDS and Clinical Research S5:002. doi:10.4172/2155-6113.S5-002, 2012 (Non-Patent Document 7)). In addition, in recent years, an increase of non-AIDS diseases such as osteoporosis, cardiovascular disturbance, and cognitive disorder in HIV-1 infected patients under ART has become a new problem. Furthermore, it is pointed out that ART is much burdensome for patients in developing countries in terms of price of drugs.

In order to overcome the limitation of such a drug treatment, it is essential to develop an effective vaccine for treatment that suppresses remaining viruses in infected cells. Further, not only in developing countries in which AIDS becomes rampant but also in various countries such as Southeast Asia and China that face rapid expansion of AIDS infection, development of a preventive vaccine that becomes a powerful card of suppressing expansion of HIV-1 infection is expected. The antibody induction that leads to HIV-1 infection prevention is a key strategy for vaccine development.

Although the development of AIDS vaccines has been vigorously conducted shortly after HIV-1 was identified as pathogen in the 1980s, a vaccine including the protein of HIV-1 or a gene thereof has not shown sufficient effectiveness until now in clinical trials. Development of new effective vaccines using new concepts and methods has been strongly required.

On the other hand, infection caused by HTLV-1 of Retroviridae is infection that results in a serious pathological condition in some infected patients such as Adult T-cell Leukemia (ATL), HTLV-1-associated myelopathy (HAM), or HTLV-1 uveitis (HU). The clinical course of the infection caused by HTLV-1 is diverse, but particularly in the case of the acute form or lymphoma form of ALT, this case has an extremely poor prognosis, so that it is necessary to promptly carry out treatment. The survival period median of a patient diagnosed with the acute form is regarded to be shorter than one year (Tsukasaki K and Tobinai K, Clin Cancer Res. 20:5217-25, 2014 (Non-Patent Document 8)).

The positive rate of HTLV-I in Japan is estimated to 0.32% and the number of infected patients is estimated to 1,000,000 or more. In past days, infected patients (carriers) were unevenly distributed in Kyushu, particularly, Okinawa Prefecture, Kagoshima Prefecture, Miyazaki Prefecture, and Nagasaki Prefecture. For example, it is reported that, while the positive rate of HTLV-1 in Tokyo is 0.15%, the positive rate in Kagoshima Prefecture in which the positive rate is the highest in the whole of country is 1.95%. However, in recent years, an increase of the positive rate also in large city areas such as Kanto and Kansai has been confirmed, and there is a concern that HTLV-1 may be spread to the whole of country (Satake M et al. J Med Virol 84:327-35, 2012 (Non-Patent Document 9)). Other than Japan, infected patients are recognized in the Caribbean, Central Africa, South America, and the like, and it is reported that a large number of Adult T-cell Leukemia (ATL) patients are also present in those area. The number of new infected patients is estimated to 3,000 a year. In Japan, about 600 to 700 persons of HTLV-I carriers are in development of ATL. The pathogenesis risk rate through the life of one carrier is about 5%. The number of fatalities per year due to ATL in Japan is estimated to about 1,000, and a decrease tendency is not observed in recent years.

As the treatment of ATL, similarly acute leukemia, hematopoietic stem cell transplantation after remission-induction therapy has been reviewed. As the remission-induction therapy, CHOP therapy (chemotherapy in which three kinds of anticancer drugs (cyclophosphamide, doxorubicin, and vincristine) are combined with adrenocortical hormone (prednisolone) or LSG15 therapy in which a larger number of drugs are combined. Further, the same kind of bone-marrow transplantation as the hematopoietic stem cell transplantation is considered. The ATL exhibits drug resistance less from the first time. Further, cases that can achieve complete remission by the science-based therapy have increased in recent years. However, recrudescence occurs frequently and if recrudescence occurs, drug resistance is exhibited, so that a standard treatment has not been established yet (Goncalves D U et al., Clinical Microbiol Rev 23:577-589, 2010 (Non-Patent Document 10)).

As an infection route of HTLV-1, mainly, maternal-to-fetal transmission due to maternal milk and horizontal transmission via sexual relations or blood (Carneiro-Proietti A B F et al., Journal of the Pediatric Infectious Diseases Society 3: s24-s29, 2014 (Non-Patent Document 11)). The most important is maternal-to-fetal transmission, and it is considered that new infection of HTLV-1 occurs mainly by HTLV-1 infection lymphocyte in maternal milk contacting lymphocyte of a baby in baby's digestive canal. In a case where a mother that is a carrier continues maternal milk childcare, about 20% of babies are regarded to become carriers. In recent years, in order to prevent vertical transmission, switching to feeding by artificial nutrition is recommended and maternal-to-fetal transmission decreased to an extent, but HTLV-1 infection has not been completely prevented, and a possibility of infection routes other than the maternal milk is suggested. Thus, development of vaccines for suppressing infection expansion is expected.

In infection prevention of enveloped viruses including HIV-1 and HTLV-1, antibody induction in which an envelope (Env) protein that is a virus surface membrane protein is targeted becomes important. Env is essential for recognizing a virus receptor on a cell surface and penetrating the virus in cells, and the reason for this is considered that this function is inhibited by an antibody so that infection can be suppressed (neutralized) (Haynes B F et al., Cell Host Microbe 19:292-303, 2016 (Non-Patent Document 12)).

It is known that many different strains depending on endemic areas exist in HIV-1, and the env gene encoding the Env protein is rich in diversity, so that a neutralizing antibody having a wide cross-reactivity that can recognize various HIV-1 strains is considered to be necessary in protection against HIV-1 infection, and the vaccine development research for induction thereof has been underway (Stephenson K E et al., Current Opinion in Immunology 41:39-46, 2016 (Non-Patent Document 13)). However, in method of related arts using inactivated virus particle, purified Env protein gp120, and the like, it is found that induction of a neutralizing antibody having high cross-reactivity is difficult, and fundamental researches are under way aiming at developing a new method. At the current moment, as an antigen for induction of the neutralizing antibody, Env antigen having a trimer structure similar to those which exist on the surface of natural virus is most promising, but since 10 to 20 molecules of the Env trimer are carried on one HIV-1 particle, a system that can present the Env antigen having a trimer structure at higher density is demanded. Further, since maturation of Env-specific B cell is important in induction of a neutralizing antibody having wide cross-reactivity, it is considered necessary to stimulate plural times with various antigens, and thus it is also important to enable multicycle inoculation.

It is known that infection and propagation of HTLV-1 are caused by infected cells being brought into direct contact with other cells. At this time, an interaction between the Env protein and a target cell receptor is necessary, so that development of a vaccine to induce an antibody targeting HTLV-1 Env is a key strategy directed to suppress HTLV-1 infection expansion (Gross C and Thomas-Kress A K, Viruses 8:74-95, 2016 (Non-Patent Document 14)).

In order to construct a vaccine inducing such an antibody, optimization of a delivery system and an antigen that leads to efficient induction is required. Generally, safety and effectiveness of vaccines are in a trade-off relationship. Vaccines using gene DNA itself of pathogen or a protein have high safety but the effect thereof is limited. Meanwhile, vaccines using attenuated pathogen itself have a desired effect but have a safety problem as seen in the accident of polio live vaccine. In particular, regarding HIV or HTLV-1, the possibility of establishing an attenuated live vaccine not having pathogenicity is not suggested. Further, a method using related viruses that have common immunogenicity and have no pathogenicity in humans at all, as in the case where Jenner used bovine smallpox as a smallpox vaccine, is also not possible in the case of HIV or HTLV-1 since there is no suitable virus.

An inactivated virus particle is a typical antibody inducing vaccine candidate. Env forms a multimer (primarily, a trimer) and is expected to be more advantageous than a purified protein antigen in terms of the adjuvant effect by core antigen, genome, or the like in cells. However, even in the inactivated virus particle, there are problems such as loss of antigenicity due to an inactivation treatment and limitation on antigen density on the virus particle. Further, there is also a concern of infection risk or safety at the time of vaccine production in a case where the inactivation treatment is not sufficient.

Meanwhile, in recent years, a vaccine using a "viral vector" has received an attention as a vaccine technique having both safety and effectiveness. A virus that infects cells of humans and does not have pathogenicity in humans is used as a carrier of an antigen gene for immunity. This vaccine expresses an antigen protein from the carried antigen gene inside inoculated human cells. It is expected that this antigen protein is presented to the immune system in the body as if expressed from a pathogen virus itself and thus evokes immunity.

However, the vaccines using the "viral vector" have not exhibited the expected effect. In the largest third phase clinical trial so far that has been collaboratively conducted by Ministry of Public Health of Thailand, US military forces, and the like on over 16,000 subjects (infection prevention study), it was reported that the AIDS infection risk of the study subject groups was reduced by about 30% (Rerks-Ngarm S et al., New Englan Journal of Medicine 361:2209-2220, 2009 (Non-Patent Document 15)). This study used two kinds of existing vaccines that did not show effect when used alone in the clinical trials therebefore (ALVAC canarypox vaccine and AIDSVAX protein vaccine) in combination, and is meaningful in that effectiveness of AIDS vaccines was proven for the first time in the world. However, the preventive effect of 30% is not sufficient as prevention vaccines, and future improvement is required for practical realization since the effect of decreasing the amount of virus in the blood of infected subjects was not recognized. Furthermore, in a case where a "viral vector" vaccine uses a replicative viral vector in which the viral vector is amplified after administration, immunity with respect to the viral vector itself is evoked in the body, and there is a disadvantage in that repeated administration of the vaccine is inhibited.

Meanwhile, a new vaccine called VLP vaccine has been in practical use. The virus-like particle (VLP) refers to a particle released from cells when only the structural protein of the virus is synthesized in eukaryotic cells such as insects or yeasts or in bacteria such as *Mycobacterium tuberculosis*. The VLP has the same appearance and antigenicity as in the virus, but the particle is hollow and does not have viral genome, and thus it is considered that the VLP does not have pathogenicity and has high safety. As the VLP vaccine, human papillomavirus (HPV) vaccine for prevention of cervical cancer, type B hepatitis virus, or the like have been in practical use. VLP of HIV-1 has been also attempted, but most thereof did not reach sufficient induction of neutralizing antibody (Zhao et al., Vacines 4:2-21, 2016 (Non-Patent Document 16)).

CITATION LIST

Non-Patent Document

Non-Patent Document 1: WHO World Health Statistics 2016.
Non-Patent Document 2: Zwahlen M, Egger M (2006) Report on UNAIDS Obligation HQ/05/422204.
Non-Patent Document 3: Sharp P M and Hahn B H, Cold Spring Harb Perspectives in Medicine 1(1): a006841, 2011.
Non-Patent Document 4: The State of the World Population 2011, UNFPA.
Non-Patent Document 5: UNAIDS Fact Sheet 2016.
Non-Patent Document 6: Consolidated guidelines on the use of antiretroviral drugs for treating and preventing. HIV infection: recommendations for a public health approach June 2013, WHO.
Non-Patent Document 7: Campo J E et al., AIDS and Clinical Research 55:002. doi:10.4172/2155-6113.55-002, 2012.
Non-Patent Document 8: Tsukasaki K and Tobinai K, Clin Cancer Res. 20: 5217-25, 2014.
Non-Patent Document 9: Satake M et al. J Med Virol 84: 327-35, 2012.
Non-Patent Document 10: Goncalves D U et al., Clinical Microbiol Rev 23: 577-589, 2010.
Non-Patent Document 11: Carneiro-Proietti A B F et al., Journal of the Pediatric Infectious Diseases Society 3: s24-s29, 2014.
Non-Patent Document 12: Haynes B F et al., Cell Host Microbe 19: 292-303, 2016.
Non-Patent Document 13: Stephenson K E et al., Current Opinion in Immunology 41:39-46, 2016.
Non-Patent Document 14: Gross C and Thomas-Kress A K, Viruses 8: 74-95, 2016.
Non-Patent Document 15: Rerks-Ngarm S et al., New Englan Journal of Medicine 361: 2209-2220, 2009.
Non-Patent Document 16: Zhao et al., Vacines 4:2-21, 2016.

SUMMARY OF THE INVENTION

Problems to be Solved by the Invention

The object of the present invention is to provide a novel vaccine for immunity induction which overcomes the defects of existing vaccine techniques as described above, holding a multimer of surface antigen such as the envelope protein that is the immunity target antigen, at a high density on the surface while maintaining the higher structure thereof, and can be administered plural times. For this objective, a non-infectious particle of paramyxovirus is used as a vaccine and a method for producing the particle and a protection method for pathogen infection using the non-infectious particle vaccine are provided.

Means for Solving the Problems

In order to solve the problems, the present inventors have devised to use the non-infectious particle of paramyxovirus vector as a vaccine, and have been successful in providing a method for producing the particle and a method of inducing an antibody against pathogen using the non-infectious particle vaccine.

Paramyxovirus including Sendai virus is an enveloped virus having single strand antisense RNA as genome. The amplification and replication are carried out using RNA throughout, and do not undergo the DNA phase. Moreover, there is no interaction with chromosome in cells and all life cycle is limited to only in the cytoplasm, so that the paramyxovirus does not impair genes of infected cells. In particular, Sendai virus does not have pathogenicity against humans. Excellent safety and the ability to strongly express a gene introduced onto genome of such paramyxovirus, particularly, Sendai virus have already been exploited by the present inventors as a vector for gene therapy and a vector for iPS cell induction, and in recent years, have been widely used in medical and research fields.

The present inventors have been successful in deleting an envelope gene (F or HN gene, or both genes) from the genome in the course of development of this Sendai virus vector. Since the envelope protein is essential in cell infection of the paramyxovirus, in the case of typical vectors for gene therapy or vectors for iPS cell induction, the deleted envelope gene is expressed in a separate helper cell, so that an infectious particle having the envelope protein on the surface is prepared.

On the other hand, the paramyxovirus replicated and amplified without supplying the envelope protein does not have the envelope protein deleted from genome on the surface thereof, and accordingly, does not have the ability to infect cells. The present inventors have focused on this non-infectious particle, and have devised a system of expressing an envelope protein of HIV-1 or HTLV-1 on this non-infectious particle and delivering the envelope protein. Since only one original envelope protein of the paramyxovirus is expressed on the surface of envelope protein-deficient paramyxovirus, it was not possible to predict whether a virus particle has particle stability or genome holding function that the virus particle originally has. Further, since there is no infectious ability, a non-infectious paramyxovirus particle that cannot exhibit replication and amplification ability could not be predicted whether the non-infectious paramyxovirus particle exhibits immunity induction property like a typical infectious virus particle. However, the present inventors have envisioned that since the original envelope protein of the paramyxovirus is not expressed in the non-infectious particle, the immunity induction ability with respect to the particle itself is lowered, and in the case of repeated administration, the non-infectious particle is more advantageous than the infectious particle.

In order to efficiently express the envelope protein of HIV-1 or HTLV-1 on the particle surface of paramyxovirus that is a virus different from those viruses, a hybrid gene (hereinafter, also referred to as "fusion gene"; a protein expressed from the fusion gene is referred to as "hybrid protein" or "fusion protein") in which a part corresponding to the extracellular domain of the envelope gene of HIV-1 or HTLV-1 is bound to a transmembrane part-cytoplasmic part of the envelope gene of the Sendai virus was prepared (WO 2016/069518). A Sendai virus F gene-derived signal sequence was further bound to the N terminal of the cytoplasmic part so that movement to outside the cell is efficiently achieved.

When the non-infectious Sendai virus particle (F-deficient) expressing the envelope protein of HIV-1 or HTLV-1 prepared in this way and the infectious Sendai virus particle (F-deficient) prepared by supplying the F protein from the helper cell were compared by western blotting, surprisingly, it was found that the non-infectious Sendai virus particle (F-deficient) expresses the envelope protein of HIV-1/HTLV-1 much more on the surface. Instead of the original envelope protein of paramyxovirus being not expressed on the non-infectious particle, an extraneous envelope protein is easily incorporated, so that the non-infectious particle was considered to be more advantageous than the infectious particle in view of presentation of an antigen on the surface of the particle.

Further, when this non-infectious Sendai virus particle (F-deficient) was administered as a boost to a mouse primed with the infectious Sendai virus particle (F-deficient), a significant booster effect was confirmed and possibility of the non-infectious Sendai virus particle (F-deficient) as a vaccine was shown.

That is, the present invention relates to a technique that expresses an antigen protein of a pathogen on a non-infectious virus particle, a method for producing the non-infectious virus particle, use of the non-infectious virus particle as a vaccine against the pathogen, a composition used therefor, and the like, and more specifically relates to the inventions described in each of the claims. Incidentally, inventions consisting of any combination of two or more inventions described in claims that cite the same claim are also inventions intended therein. That is, the present invention relates to the following inventions.

[1] A paramyxovirus non-infectious particle, which expresses an antigen protein of a heterologous pathogen on the surface of the virus particle.
[2] The non-infectious particle of [1], in which at least one envelope protein of the paramyxovirus has been deleted from the surface of the virus particle.
[3] The non-infectious particle of [1] or [2], in which the F protein of the paramyxovirus has been deleted from the surface of the virus particle.
[4] The non-infectious particle of any one of [1] to [3], which comprises a paramyxovirus genome from which at least one envelope protein gene has been deleted.
[5] The non-infectious particle of [4], in which the deleted envelope protein gene is an F gene.
[6] The non-infectious particle of any one of [1] to [5], in which the paramyxovirus is Sendai virus.
[7] The non-infectious particle of any one of [1] to [6], in which the antigen protein of the heterologous pathogen comprises all or part of an envelope protein of a retrovirus.
[8] The non-infectious particle of any one of [1] to [7], in which the antigen protein of the heterologous pathogen comprises all or part of an envelope protein of HTLV-1 or HIV-1.
[9] A composition comprising the non-infectious particle of any one of [1] to [8].
[10] A vaccine formulation comprising the non-infectious particle of any one of [1] to [8].
[11] The vaccine formulation of [10], which is for use in booster inoculation.
[12] The vaccine formulation of [10], which is used in booster inoculation, in which the pathogen is different from a pathogen from which an antigen for primary inoculation is derived, and in which the formulation is for use in increasing the cross-reactivity of an antibody to be induced.
[13] A method for producing the non-infectious particle of any one of [1] to [8], which comprises introducing into a cell a paramyxovirus vector from which at least one envelope protein gene has been deleted and which carries an antigen protein gene of a heterologous pathogen, and collecting a generated paramyxovirus non-infectious particle.
[14] A paramyxovirus vector in which at least one envelope protein gene has been deleted from the genome and which carries an antigen protein gene of a heterologous pathogen, in which the vector expresses the antigen protein gene of the heterologous pathogen on the surface of the virus particle.
[15] The paramyxovirus vector of [14], in which the antigen protein gene of the heterologous pathogen is an envelope protein of HTLV-1 or HIV-1.
[16] The paramyxovirus vector of [14] or [15], in which the paramyxovirus vector is a Sendai virus vector.
[17] The paramyxovirus vector of any one of [14] to [16], in which the deleted envelope protein gene is an F gene.

Further, the present invention relates to paramyxovirus genomic RNA of the non-infectious virus particle of the present invention, antigenomic RNA of the genomic RNA (that is, RNA consisting of a complementary sequence of the genomic RNA), and DNA encoding at least any of these RNAs. Furthermore, the present invention provides a vector encoding at least any of these RNAs and a vector comprising the DNA. The vector is not particularly limited, and may be a desired vector such as a plasmid vector, a phage vector, a viral vector, or artificial chromosome, as long as it can hold nucleic acid. An expression vector having the ability of transcribing genomic RNA or antigenomic RNA is useful for producing the non-infectious virus particle and the viral vector of the present invention.

Incidentally, any matters of the inventions described herein and any combination thereof are intended herein. Further, in these inventions, inventions excluding any matters described herein, or any combinations thereof are also intended herein. Furthermore, certain specific embodiments described herein regarding the present invention not only disclose these embodiments, but also disclose inventions excluding these embodiments from generic inventions disclosed herein which include these embodiments.

Effects of the Invention

According to the present invention, the non-infectious virus particle in which an antigen protein of a pathogen is expressed on the surface in a three-dimensional structure similar to those existing in nature can be used as a vaccine against the pathogen. It is particularly useful in that, by using an Env gene-deficient vector, multimolecular antigen protein can be carried on the particle, and by administrating it as a vaccine, antibody induction can be carried out efficiently.

The infectious particle (SeV18+gp63ectoF/dF) and the non-infectious particle (SeV18+gp63ectoF/dF/NVP) of the F-deficient Sendai virus vector carrying HTLV-1 envelope protein were analyzed by a western blotting method. After electrophoresis of 15 μl of each analyte with acrylamide gel, gp63ectoF protein on the particle was detected using an anti-HTLV-1 gp46 antibody. The amount of the gp63ectoF protein on the non-infectious particle significantly increased as compared to the infectious particle.
M. Magic maker, 1. SeV18+gp63ecto/dF+, 2. SeV18+gp63ectoF/dF, 3. SeV18+gp63ectoF/dF/NVP.
*SeV18+gp63ecto/dF is an infectious particle produced by a vector carrying only gp63ecto that is not fused with Sendai virus F.

Figure 3:
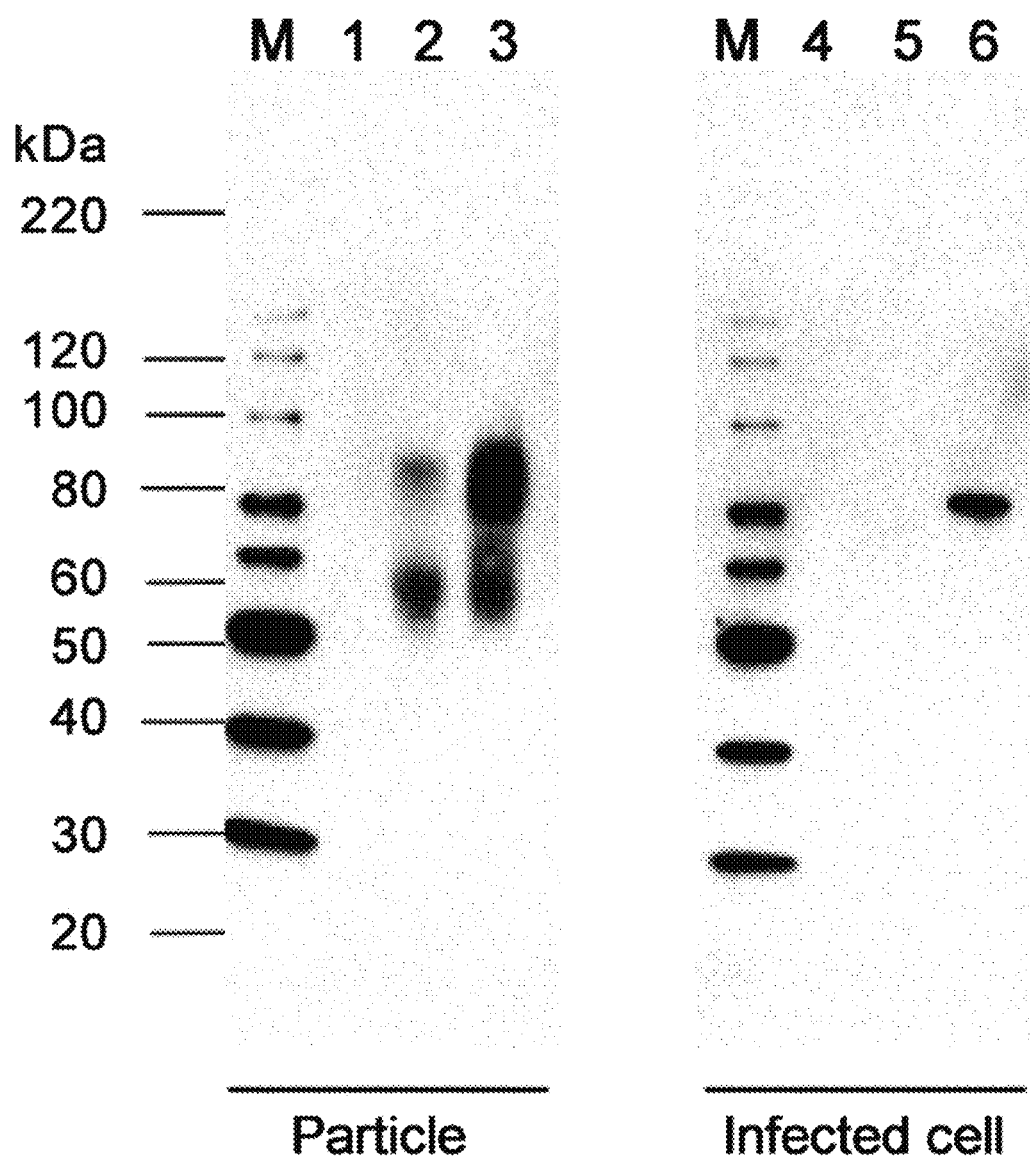

FIG. 3 shows analysis of an infectious particle and a non-infectious particle of F-deficient Sendai virus vector carrying HTLV-1 envelope protein by a western blotting method.

The infectious particle (SeV18+gp63ectoF/dF) and the non-infectious particle (SeV18+gp63ectoF/dF/NVP) of the F-deficient Sendai virus vector carrying HTLV-1 envelope protein were analyzed by a western blotting method. After electrophoresis of 1 μg of each analyte with acrylamide gel, gp63ectoF protein on the particle was detected using an anti-HTLV-1 gp46 antibody. The amount of the gp63ectoF protein on the non-infectious particle significantly increased as compared to the infectious particle. Left: the infectious particle or the non-infectious particle, Right: lysate of a cell (LLC/MK2 cell) into which Sendai virus vector expressing HTLV-1 envelope protein fused with SeV F protein (SeV18+gp63ectoF/dF) or not fused with SeV F protein (SeV18+gp63ecto/dF) is introduced.
Left: M. Magic maker, 1. SeV18+gp63ecto/dF, 2. SeV18+gp63ectoF/dF, 3. SeV18+gp63ectoF/dF/NVP.
Right: M. Magic maker, 4. MK2/control (non-infectious), 5. MK2/SeV18+gp63ecto/dF, 6. MK2/SeV18+gp63ectoF/dF.

Figure 4:
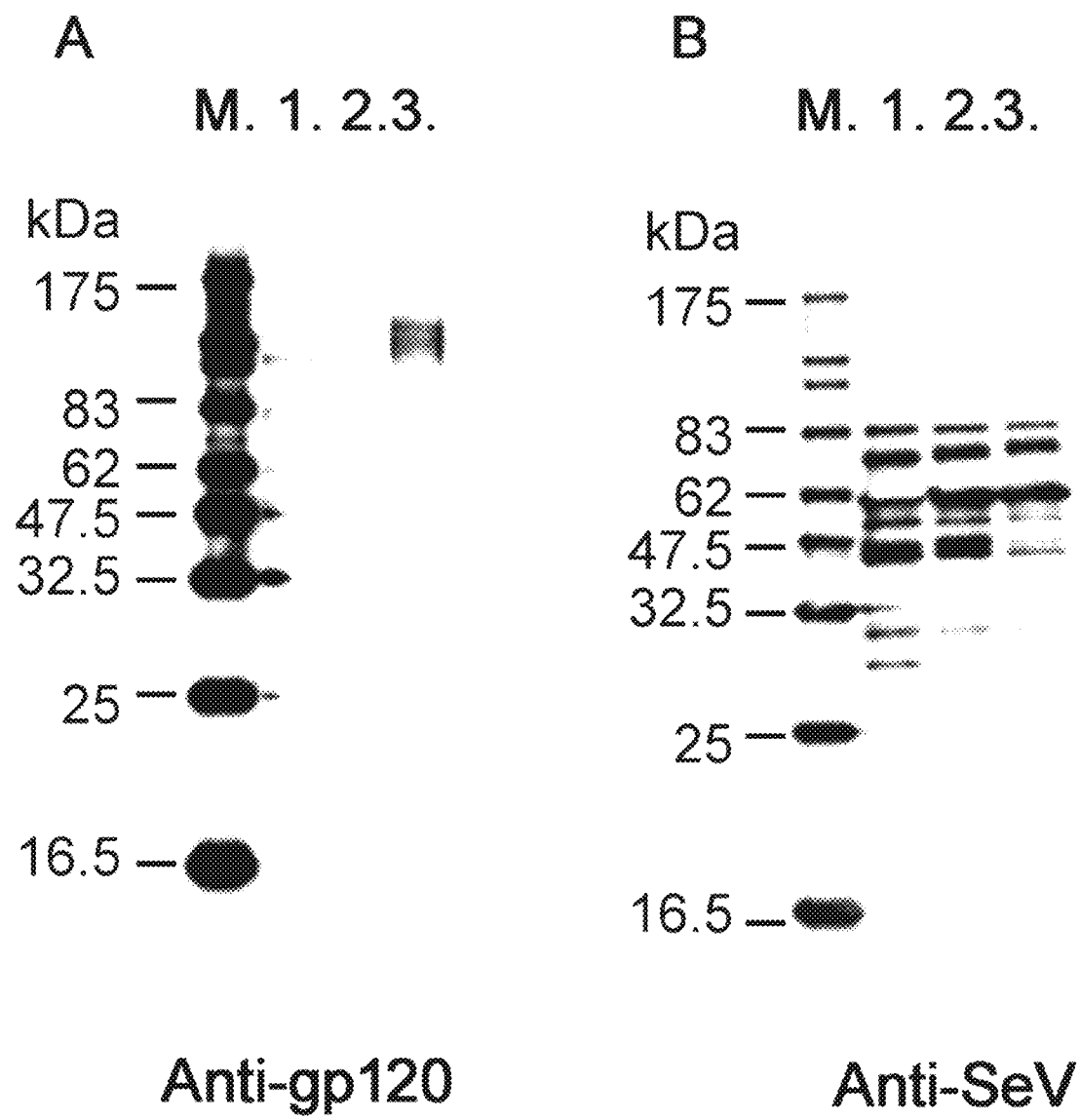

FIG. 4 shows analysis of an infectious particle and a non-infectious particle of F-deficient Sendai virus vector carrying HIV-1 envelope protein by a western blotting method.

The infectious particle (SeV18+sfEnvF/dF) and the non-infectious particle (SeV18+sfEnvF/dF/NVP) of F-deficient Sendai virus vector carrying HIV-1 envelope protein were analyzed by a western blotting method. After electrophoresis of each analyte with acrylamide gel, sfEnvF protein on the particle was detected using an anti-HIV-1 gp120 antibody (panel A). In order to confirm that the amount of Sendai virus in each applied analyte is constant, after electrophoresis with acrylamide gel, Sendai virus protein was detected using an anti-Sendai virus antibody (panel B). The amount of Sendai virus per lane was set to be constant by adjusting the total amount of protein in each applied analyte. The amount of the sfEnvF protein on the non-infectious particle significantly increased as compared to the infectious particle.
Panel A: detection of the sfEnvF protein by the anti-HIV-1 gp120 antibody
M. Magic maker, 1. SeV-sfEnvF (NP) with the total amount of protein of 1.0 μg, 2. SeV18+sfEnvF/dF with the total amount of protein of 1.35 μg, 3. SeV18+sfEnvF/dF/NVP with the total amount of protein of 1.5 μg.
Panel B: detection of the Sendai virus protein by the anti-Sendai virus antibody
M. Magic maker, 1. SeV-sfEnvF (NP) with the total amount of protein of 0.1 μg, 2. SeV18+sfEnvF/dF with the total amount of protein of 0.135 μg, 3. SeV18+sfEnvF/dF/NVP with the total amount of protein of 0.15 μg FIG. 5 shows a booster effect by a non-infectious particle expressing HTLV-1 envelope protein (ELISA method).

Results of immunity induction experiment with a mouse (BALB/c) using an infectious particle (SeV18+gp63ectoF/dF) and a non-infectious particle (SeV18+gp63ectoF/dF/NVP) of F-deficient Sendai virus vector carrying HTLV-1 envelope protein are shown. When average values of respective groups of OD450 measurement values obtained by subtracting the background of ELISA data targeting at HTLV-1 gp46 protein using blood plasma of an immune mouse were compared, the group in which inoculation of the infectious particle (SeV18+gp63ectoF/dF) was performed once and then boost inoculation of the non-infectious particle (SeV18+gp63ectoF/dF/NVP) was performed two times showed a value about 3.9 times that of the group in which inoculation of the infectious particle (SeV18+gp63ectoF/dF) was performed only once.

Figure 6:
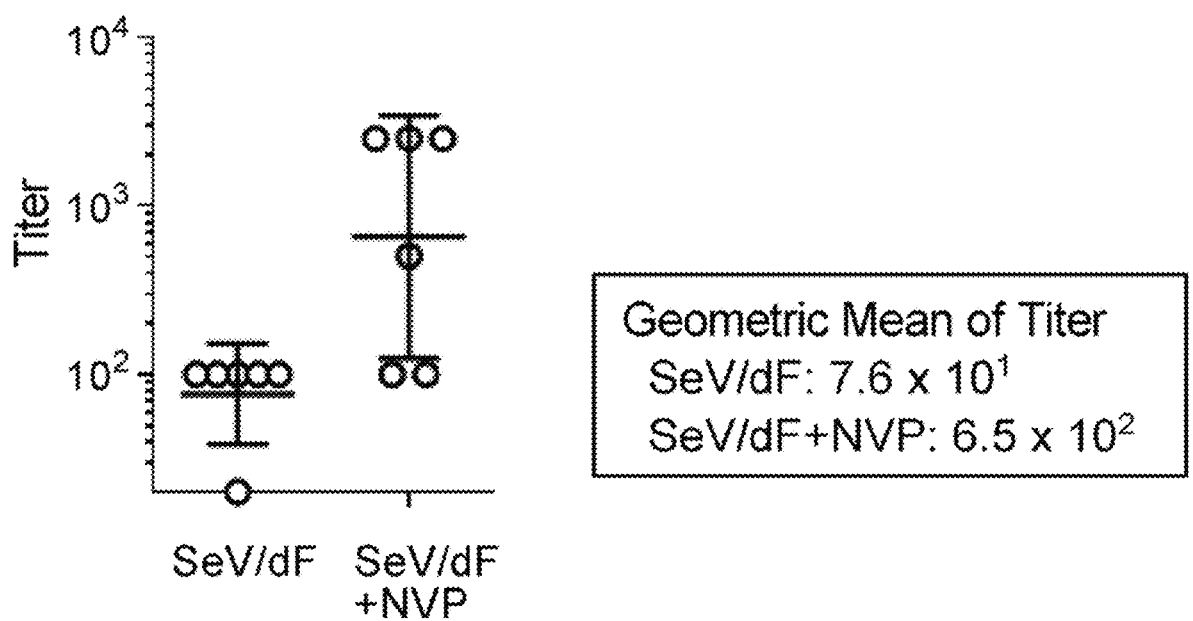

FIG. 6 shows a booster effect by a non-infectious particle expressing HTLV-1 envelope protein (western blotting method).

Figure 5:
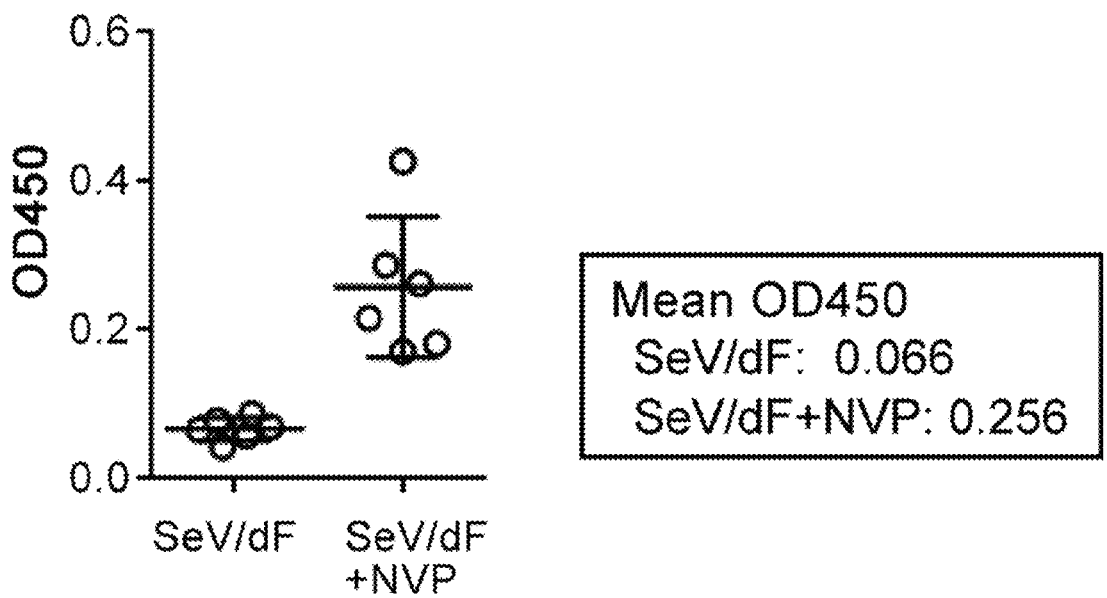

Results obtained by detecting an HTLV-1 gp46-binding antibody in the blood plasma of the immune mouse in an experiment performed in the same manner as in FIG. 5 by Western Blot are shown. The group in which inoculation of the infectious particle (SeV18+gp63ectoF/dF) was performed once and then boost inoculation of the non-infectious particle (SeV18+gp63ectoF/dF/NVP) was performed two times showed a value about 8.5 times that of the group in which inoculation of the infectious particle (SeV18+gp63ectoF/dF) was performed only once.

Figure 7:
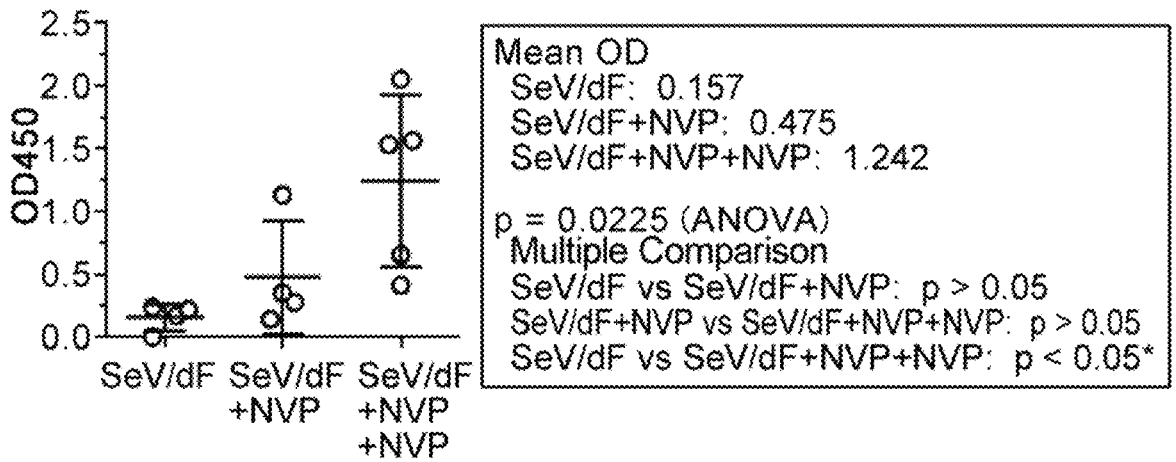

FIG. 7 shows a booster effect by a non-infectious particle expressing HIV-1 envelope protein.

Results of immunity induction experiment with a mouse (BALB/c) using an infectious particle (SeV18+sfEnvF/dF) and a non-infectious particle (SeV18+sfEnvF/dF/NVP) of F-deficient Sendai virus vector expressing sfEnv-F are shown. When average values of respective groups of measurement values obtained by subtracting the background of ELISA data targeting at HIV-1 gp120 protein using blood plasma of an immune mouse are compared, as compared to the group in which inoculation of the infectious particle (SeV18+sfEnvF/dF) is performed only two times, the group in which inoculation of the infectious particle (SeV18+gp63ectoF/dF) is performed two times and boost inoculation by the non-infectious particle (SeV18+sfEnvF/dF/NVP) is performed two times shows a value about 3.0 times, and the group in which inoculation of the infectious particle (SeV18+gp63ectoF/dF) is performed two times and boost inoculation by the non-infectious particle (SeV18+sfEnvF/dF/NVP) is performed four times shows a value about 8.0 times.

Figure 8:
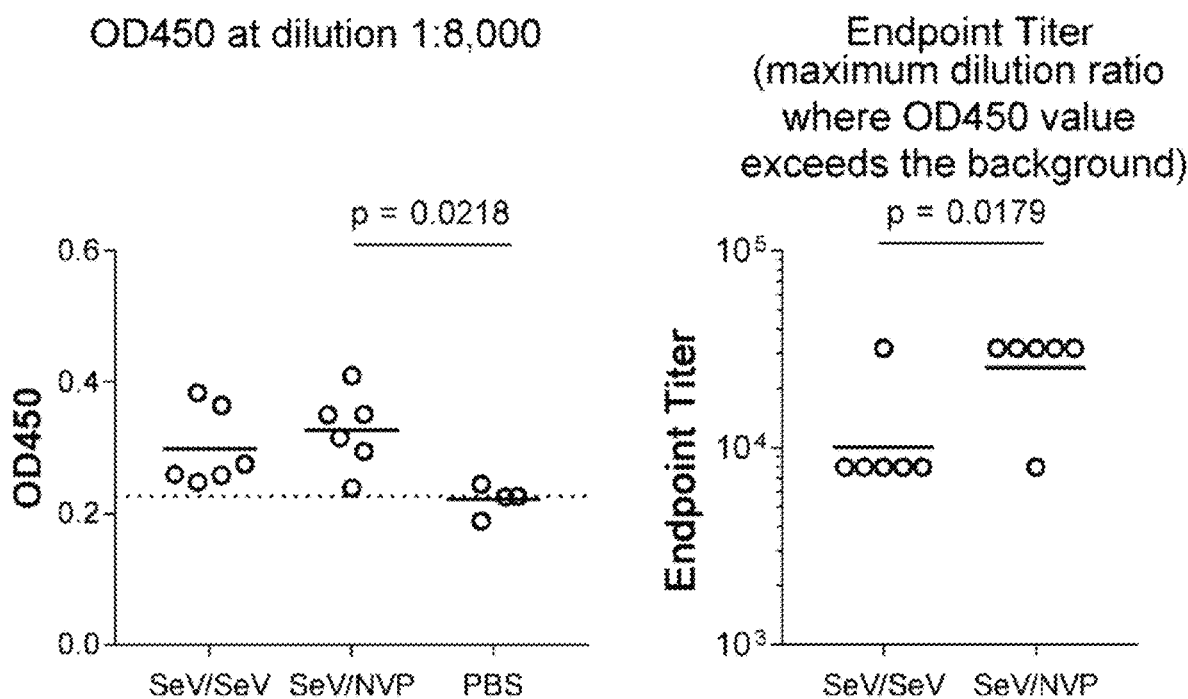

FIG. 8 shows an anti-HTLV antibody booster effect of a non-infectious particle expressing HTLV-1 envelope protein.

Results of immunity induction experiment with a mouse (BALB/c) using an infectious particle (SeV18+gp63ectoF/dF) and a non-infectious particle (SeV18+gp63ectoF/dF/NVP) of F gene-deficient Sendai virus vector expressing gp63ectoF are shown. In the first group (SeV/SeV group), inoculation of the infectious particle (SeV18+gp63ectoF/dF) was performed four times, and in the second group (SeV/NVP group), inoculation of the infectious particle (SeV18+gp63ectoF/dF) was performed once and inoculation of the non-infectious particle (SeV18+gp63ectoF/dF/NVP) was performed three times. Further, as a negative control, in the third group (PBS group), PBS inoculation was performed four times. In antibody titer measurement with respect to HTLV-1 gp46 protein by ELISA, in data using blood plasma diluted 8,000-fold, both the SeV/SeV group and the SeV/NVP group showed a high value, and particularly, the SeV/NVP group showed a significantly higher value than the control group. Further, in comparison on endpoint titer, the SeV/NVP group showed a significantly higher value than the SeV/SeV group.

Figure 9:
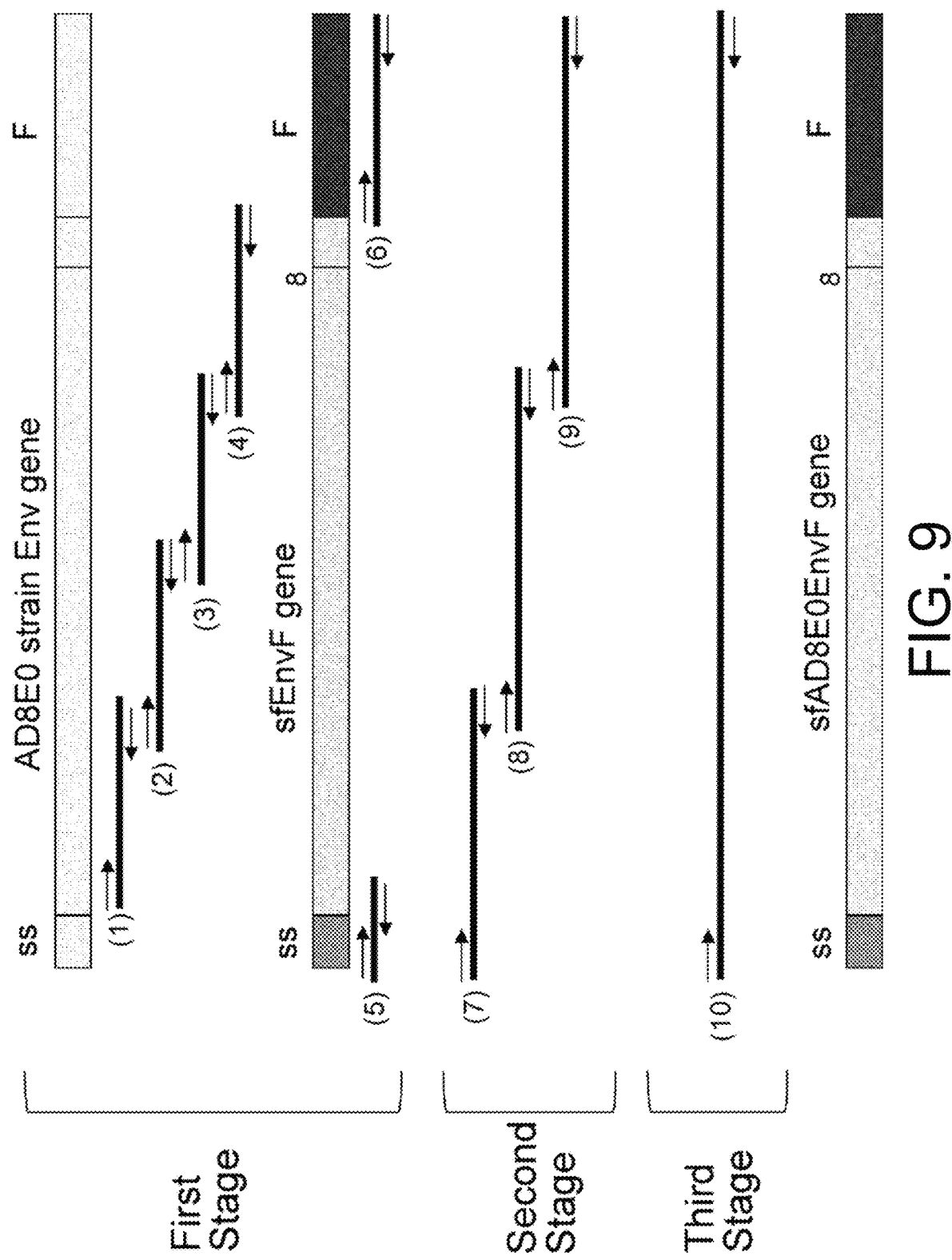

FIG. 9 is a diagram showing a three-stage PCR scheme for preparing nucleic acid encoding sfAD8EOEnvF fusion protein including ectodomain sfAD8EOEnv of AD8EO strain (HIV-1 subtype B)-derived Env.

Figure 10:
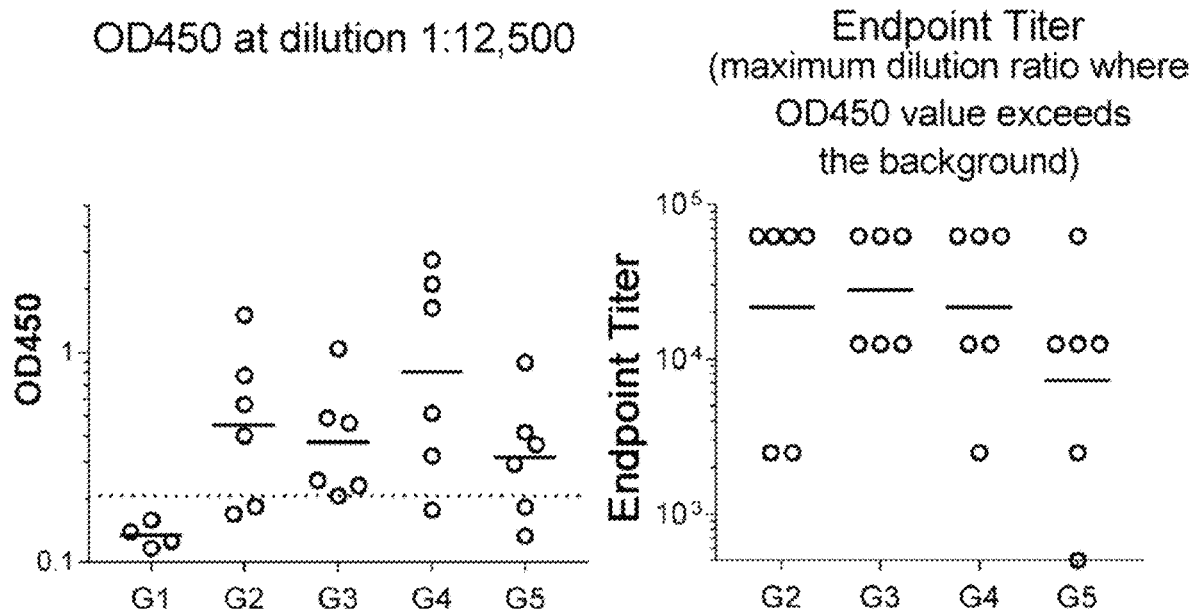

FIG. 10 shows an anti-HIV-1 antibody booster effect of a non-infectious particle expressing HIV-1 envelope protein.

Results of immunity induction experiment with a mouse (BALB/c) using an infectious particle (SeV18+sfEnvF/dF) and a non-infectious particle (SeV18+sfEnvF/dF/NVP) of F-deficient Sendai virus vector expressing sfEnv-F are shown. Regarding EnvF, BG505EnvF using a BG505 strain-derived ectodomain and AD8EOEnvF using an AD8EO strain-derived ectodomain were used. In the PBS group (G1), PBS inoculation was performed four times as a negative control. In the SeV/SeV-BG505 group (G2), inoculation of the infectious particle expressing BG505EnvF (SeV18+sfBG505EnvF/dF) was performed four times, and in the SeV/NVP-BG505 group (G3), inoculation of the infectious particle expressing BG505EnvF (SeV18+sfBG505EnvF/dF) was performed once and inoculation of the non-infectious particle expressing BG505EnvF (SeV18+sfBG505EnvF/dF/NVP) was performed three times. Further, for reviewing the cross-reactivity expansion effect of an antibody by using a different antigen in boost, inoculation of the infectious particle expressing BG505EnvF (SeV18+sfBG505EnvF/dF) was performed two times, and then, as the SeV/SeV-AD8EO group (G4), inoculation of the infectious particle expressing AD8EOEnvF (SeV18+sfAD8EOEnvF/dF) was performed two times, or as the SeV/NVP-AD8EO group (G5), inoculation of non-infectious particle expressing BG505EnvF (SeV18+sfBG505EnvF/dF/NVP) and the non-infectious particle expressing AD8EOEnvF (SeV18+sfAD8EOEnvF/dF/NVP) was performed once, respectively. In anti-BG505 gp120 antibody titer measurement by ELISA, in the average value of OD450 values and the endpoint titer, the SeV/NVP-BG505 group (G3) showed a value equal to or higher than a value of the SeV/SeV-BG505 group (G2), and the antibody boost ability by the non-infectious particle (NVP) expressing sfEnvF was shown to be equal to or higher than the infectious particle (SeV) expressing sfEnvF. Further, also in both the SeV/SeV-AD8EO group (G4) and the SeV/NVP-AD8EO group (G5), in the average value of OD450 values and the endpoint titer, the SeV/SeV-AD8EO group (G4) and the SeV/NVP-AD8EO group (G5) showed a value equal to or higher than a value of the SeV/NVP-BG505 group (G3) and the SeV/SeV-BG505 group (G2), and owing to boost by the infectious particle and the non-infectious particle expressing AD8EOEnvF could effectively induce an antibody reacting to BG505 gp120.

Figure 11:
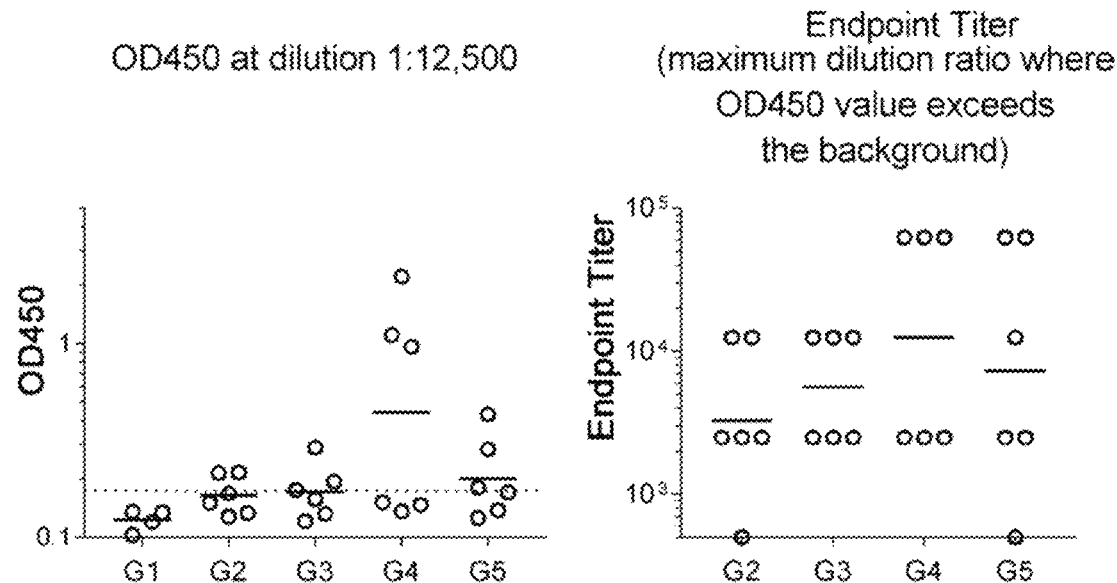
Figure 11:
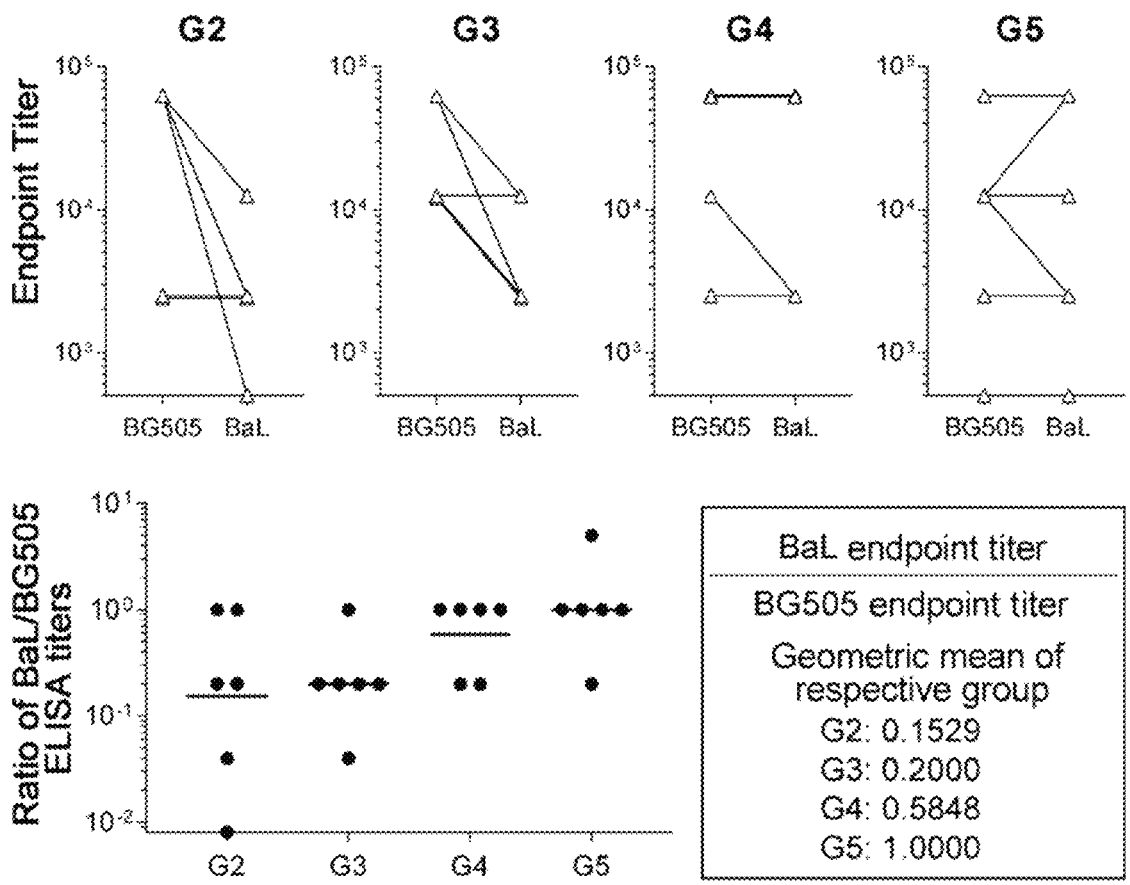

FIG. 11 shows an anti-HIV-1 antibody booster effect (2) of a non-infectious particle expressing HIV-1 envelope protein.

In order to examine the cross-reactivity expansion effect of an antibody by boost inoculation of the infectious particle or non-infectious particle expressing AD8EOEnvF using the blood samples collected in the mouse experiment shown in FIG. 10, similar anti-gp120 antibody ELISA was performed using BaL gp120 protein belonging to the same HIV-1 subtype B as AD8EO. As a result, in the endpoint titer, a high value was shown in the SeV/SeV-AD8EO group (G4), and also in the SeV/NVP-AD8EO group (G5), a value equal to the value of the SeV/SeV-AD8EO group (G4) was shown. Further, as a result of analysis of a ratio value of BG505 endpoint titer and BaL endpoint titer, the SeV/SeV-AD8EO group (G4) and SeV/NVP-AD8EO group (G5) showed a higher value than a value of the SeV/NVP-BG505 group (G3) and the SeV/SeV-BG505 group (G2), and particularly, a high value was shown in the SeV/NVP-AD8EO group (G5).

MODE FOR CARRYING OUT THE INVENTION

Hereinafter, embodiments of the present invention will be described in detail.

In the present invention, the "vaccine" refers to a composition for evoking immune reaction against an antigen, and for example, refers to a composition used for prevention or treatment of contagious diseases or infection. The vaccine contains the antigen or can express the antigen, and accordingly, can induce immune response against the antigen. The paramyxovirus non-infectious particle of the present invention may be formulated as a vaccine containing an antigen for the prevention or treatment of infection, propagation, and epidemic of pathogenic microorganisms. This vaccine can be used in a desired form.

The "antigen" is a molecule containing one or more epitopes (a part of an antigen identified by an antibody or an immune cell) and refers to a molecule that is capable of inducing antigen-specific immune response by stimulating the immune system of a host. The immune response may be humoral immune response and/or cellular immune response. Although about three to several amino acids may serve as one epitope, one epitope in a protein typically contains about 7 to 15 amino acids, for example, at least 8, 9, 10, 12, or 14 amino acids. Incidentally, in the present invention, the epitope also includes not only an epitope formed from a primary structure but also an epitope depending on a steric structure of protein. Further, an antigen is also referred to as an immunogen.

The "non-infectious virus particle" of the present invention refers to a virus particle having no infectiveness. Specifically, the non-infectious virus particle refers to a virus particle not having the ability to introduce the nucleic acid in the particle into the cell by contacting the cell surface, the ability which a typical virus particle has. The non-infectious virus particle may be a particle not practically having one or more viral proteins necessary for infection. The expression "not practically having" refers to $1/50$ or less, preferably $1/100$ or less, $1/200$ or less, $1/500$ or less, $1/1000$ or less, $1/2000$ or less, and preferably $1/5000$ or less of the protein level of a wild-type virus particle. Further, the virus particle refers to a particle formed by the action similar to the particle formation mechanism of the virus. The non-infectious virus particle of the present invention is a particle wrapped in envelope (cell membrane-derived biomembrane). For example, the non-infectious virus particle of the paramyxovirus comprises genomic RNA of the paramyxovirus. At least one envelope gene may be deleted in the viral genomic RNA. Further, the viral genomic RNA may form a complex (ribonucleoprotein; RNP) with paramyxovirus proteins. The RNP is, for example, a complex of the genomic RNA of paramyxovirus and N, P, and L proteins. The N, P, and L proteins may be encoded, for example, in the viral genome. The "non-infectious virus particle" of the present invention is, for example, a particle produced when the viral vector from which at least one envelope gene is deleted is replicated and amplified without supplying the deleted envelope protein.

In the present invention, "viral vector" is a vector that has a genomic nucleic acid derived from the virus and can express a transgene by incorporating the transgene into the nucleic acid to introduce into a cell. Since the paramyxovirus vector is a chromosomally non-integrating viral vector and the vector is expressed in the cytoplasm, there is no risk that the transgene will become integrated into the chromosome (nucleus-derived chromosome) of the host. Therefore, the vector is safe and can be removed from the infected cells. In the present invention, the paramyxovirus vector includes an infectious virus particle, as well as a complex of viral core, viral genome, and viral protein or a complex comprising the non-infectious virus particle and the like, which is a complex having the ability to express carried gene by introduction into a cell. For example, in the paramyxovirus, ribonucleoprotein (the viral core portion) consisting of paramyxovirus genome and paramyxovirus proteins (NP, P, and L proteins) bound thereto can express transgenes in cells when they are introduced into cells (WO 00/70055). Introduction into cells may be appropriately carried out using transfection reagents and the like. Such ribonucleoproteins (RNPs) are also included in the paramyxovirus vector in the present invention. In the present invention, the paramyxovirus vector is preferably a particle in which the RNP is wrapped in a cell membrane-derived biomembrane.

In the present invention, the "antigen protein of the heterologous pathogen" refers to a protein comprising an antigen derived from a pathogen of a different origin from the paramyxovirus from which the non-infectious particle of the present invention is derived. Such a pathogen may be a pathogenic paramyxovirus of a different origin from the paramyxovirus from which the non-infectious particle of the present invention or may be a different kind, that is, a living organism other than the paramyxovirus (a virus is also a living organism). Further, the pathogen refers to a living organism (including a virus) that may at least transiently impair the health condition of a host, and is preferably a microorganism and more preferably a virus, for example, a virus having an envelope (enveloped virus). The host is not particularly limited, but is preferably a mammal and more preferably a human.

In the present invention, the expression "a certain protein is expressed on the surface of the virus particle" indicates that the protein is expressed on the surface of the particle, and specifically, indicates that the protein is held on the surface of the particle. When the particle is formed from a cell, the protein is expressed in the cell to exist on the cell membrane, and the virus particle buds on the cell membrane, so that a virus particle in which the protein is expressed on the surface of the virus can be obtained. The virus particle may or may not have the ability to express the protein, but preferably has the ability to express the protein.

In the present invention, the expression "at least one envelope protein of the paramyxovirus has been deleted from the surface of the virus particle" indicates that at least one envelope protein which the wild-type virus particle of the paramyxovirus holds on the surface of the particle does not exist on the surface of the particle. Such a virus particle, as described above, can be produced by a virus in which at least one envelope gene has been deleted being expressed in a cell without supplying the deleted envelope protein. In the virus particle produced in this way, at least one envelope protein of the paramyxovirus has been deleted from the surface of the virus particle, and a viral genome in which a gene encoding the envelope protein is deleted is held in the particle. Examples of the envelope protein include F protein and/or HN protein.

The paramyxovirus in the present invention refers to a virus belonging to Paramyxoviridae or a derivative thereof. The Paramyxoviridae is one of Mononegavirale groups having non-segmented negative-strand RNA as the genome and includes Paramyxovirinae (the genera Respirovirus (also referred to as the genus Paramyxovirus), Rubulavirus, and Morbillivirus) and Pneumovirinae (including the genera Pneumovirus and Metapneumovirus). Specific examples of the viruses included in Paramyxoviridae viruses include Sendai virus, Newcastle disease virus, Mumps virus, Measles virus, Respiratory syncytial virus (RS virus), rinderpest virus, distemper virus, simian parainfluenza virus (SV5), and human parainfluenza viruses 1, 2, and 3. More specific examples include Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MeV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). As Rhabdoviridae, Vesicular stomatitis virus and Rabies virus belonging to the Rhabdoviridae family, and the like are included.

Incidentally, the genomic RNA of the paramyxovirus is a negative strand, and the amino acid sequence of protein is encoded by antigenome having a complementary sequence of the genomic RNA. In the present invention, for convenience sake, both the genome and the antigenome may be referred to as genome.

The viruses of the present invention are preferably viruses belonging to the Paramyxovirinae (including the genus Respirovirus, the genus Rubulavirus, and the genus Morbillivirus) or derivatives thereof, and more preferably viruses belonging to the genus Respirovirus (also referred to as the genus Paramyxovirus) or derivatives thereof. Derivatives include chemically modified viruses and viruses whose viral genes have been modified such that the gene transfer ability of the virus is not impaired. Examples of Respirovirus viruses to which the present invention can be applied include human parainfluenza virus 1 (HPIV-1), human parainfluenza virus 3 (HPIV-3), bovine parainfluenza virus 3 (BPIV-3), Sendai virus (also called mouse parainfluenza virus 1), measles virus, simian parainfluenza virus (SV5), and simian parainfluenza virus 10 (SPIV-10). The paramyxovirus in the present invention is most preferably Sendai virus.

The paramyxovirus typically contains a complex comprising RNA and protein (ribonucleoprotein; RNP) in the interior of the envelope. The RNA included in RNP is (−)-strand (negative-strand) single-stranded RNA that is a genome of the negative-strand RNA virus and this single-stranded RNA is bound to NP protein, P protein, and L protein to form RNP. The RNA included in this RNP is used as a template for transcribing and replicating the viral genome (Lamb, R. A., and D. Kolakofsky, 1996, Paramyxoviridae: The viruses and their replication. pp. 1177-1204. In Fields Virology, 3rd edn. Fields, B. N., D. M. Knipe, and P. M. Howley et al. (ed.), Raven Press, New York, N.Y.).

The "NP, P, M, F, HN, and L genes" of the paramyxovirus refer to genes encoding nucleocapsid, phospho, matrix, fusion, hemagglutinin-neuraminidase, and large proteins, respectively. The nucleocapsid (NP) protein is bound to the genomic RNA and is an essential protein in order for the genomic RNA to have template activity. In general, the NP gene is also described as "N gene" in some cases. The phospho (P) protein is a phosphorylated protein that is a small subunit of RNA polymerase. The matrix (M) protein exhibits the function of maintaining the virus particle structure from the interior side. The fusion (F) protein is a membrane fusion protein involved in the penetration into host cells, and the hemagglutinin-neuraminidase (HN) protein is a protein involved in binding with host cells. The large (L) protein is a large subunit of RNA polymerase. Each of the above-described genes has a transcriptional regulation unit, single mRNA is transcribed from each gene, and then the protein is transcribed. From the P gene, in addition to the P protein, non-structural protein (C) translated by using different ORF and protein (V) formed by RNA editing during reading P protein mRNA are translated. For example, respective genes in each virus belonging to Paramyxovirinae are typically described as follows in the order of being encoded from the front (3') of the genome.

the genus Respirovirus N P/C/V M F HN-L
the genus Rubulavirus N P/V M F HN (SH) L
the genus Morbillivirus N P/C/V M F H-L For examples of accession numbers in the database for the nucleotide sequences of Sendai virus genes, see M29343, M30202, M30203, M30204, M51331, M55565, M69046, and X17218 for the N gene, M30202, M30203, M30204, M55565, M69046, X00583, X17007, and X17008 for the P gene, D11446, K02742, M30202, M30203, M30204, M69046, U31956, X00584, and X53056 for the M gene, D00152, D11446, D17334, D17335, M30202, M30203, M30204, M69046, X00152, and X02131 for the F gene, D26475, M12397, M30202, M30203, M30204, M69046, X00586, X02808, and X56131 for the HN gene, D00053, M30202, M30203, M30204, M69040, X00587, and X58886 for the L gene. Examples of viral genes encoded by other viruses may include CDV, AF014953; DMV, X75961; HPIV-1, D01070; HPIV-2, M55320; HPIV-3, D10025; Mapuera, X85128; Mumps, D86172; MeV, K01711; NDV, AF064091; PDPR, X74443; PDV, X75717; RPV, X68311; SeV, X00087; SV5, M81442; and Tupaia, AF079780 for the N gene, CDV, X51869; DMV, 247758; HPIV-1, M74081; HPIV-3, X04721; HPIV-4a, M55975; HPIV-4b, M55976; Mumps, D86173; MeV, M89920; NDV, M20302; PDV, X75960; RPV, X68311; SeV, M30202; SV5, AF052755; and Tupaia, AF079780 for the P gene, CDV, AF014953; DMV, 247758; HPIV-1, M74081; HPIV-3, D00047; MeV, AB016162; RPV, X68311; SeV, AB005796; and Tupaia, AF079780 for the C gene, CDV, M12669; DMV Z30087; HPIV-1, 538067; HPIV-2, M62734; HPIV-3, D00130; HPIV-4a, D10241; HPIV-4b, D10242; Mumps, D86171; MeV, AB012948; NDV, AF089819; PDPR, 247977; PDV, X75717; RPV, M34018; SeV, U31956; and SV5, M32248 for the M gene, CDV, M21849; DMV, AJ224704; HPN-1, M22347; HPIV-2, M60182; HPIV-3, X05303, HPIV-4a, D49821; HPIV-4b, D49822; Mumps, D86169; MeV, AB003178; NDV, AF048763; PDPR, 237017; PDV, AJ224706; RPV, M21514; SeV, D17334; and SV5, AB021962 for the F gene, CDV, AF112189; DMV, AJ224705; HPIV-1, U709498; HPIV-2. D000865; HPIV-3, AB012132; HPIV-4A, M34033; HPIV-4B, AB006954; Mumps, X99040; MeV, K01711; NDV, AF204872; PDPR, X74443; PDV, 236979; RPV, AF132934; SeV, U06433; and SV-5, S76876 for the HN (H or G) gene, and CDV, AF014953; DMV, AJ608288; HPIV-1, AF117818; HPIV-2, X57559; HPIV-3, AB012132; Mumps, AB040874; MeV, K01711; NDV, AY049766; PDPR, AJ849636; PDV, Y09630; RPV,Z30698; and SV-5, D13868 for the L gene. However, multiple strains are known for each of the viruses, and genes consisting of a sequence other than those exemplified above may exist due to strain differences. Sendai virus vectors carrying viral genes derived from any of those genes are useful as viral vectors for producing the non-infectious particle of the present invention. For example, the Sendai virus vector, and the infectious and non-infectious particles of the present invention may contain a nucleotide sequence having 90% or more, preferably 95% or more, 96% or more, 97% or more, 98% or more, or 99% or more identity to the coding sequence of any of the above-described viral genes. In addition, the Sendai virus vector, and the infectious and non-infectious particles of the present invention may contain, for example, a nucleotide sequence encoding an amino acid sequence having 90% or more, preferably 95% or more, 96% or more, 97% or more, 98% or more, or 99% or more identity to an amino acid sequence encoded by the coding sequence of any of the above-described viral genes. Further, the Sendai virus vector, and the infectious and non-infectious particles of the present invention may contain, for example, a nucleotide sequence encoding an amino acid sequence with ten or less, preferably nine or less, eight or less, seven or less, six or less, five or less, four or less, three or less, two or less, or one amino acid substitutions, insertions, deletions, and/or additions in an amino acid sequence encoded by the coding sequence of any one of the above-described viral genes.

Incidentally, the sequences referenced by the database accession numbers such as the nucleotide sequences and amino acid sequences described herein refer to sequences on, for example, the filing date and priority date of this application, and can be identified as sequences at the time of either the filing date or priority date of the present application, and are preferably identified as sequences on the filing date of this application. The sequences at the respective time points can be identified by referring to the revision history of the database.

The paramyxovirus used in the present invention may be a derivative, and examples of the derivative include chemically modified viruses and viruses whose viral genes have been modified such that the gene transfer ability of the virus is not impaired.

Further, the paramyxovirus may be derived from natural strains, wild-type strains, mutant strains, laboratory-passaged strains, artificially constructed strains, and the like. An example is the Sendai virus Z strain (Medical Journal of Osaka University Vol. 6, No. 1, March 1955 p 1-15) although not limited thereto. That is, these viruses may be viruses having similar structures as viruses isolated from nature, or viruses artificially modified by genetic recombination, as long as the non-infectious virus particle can be produced. For example, they may have mutations or deletions in any of the genes of the wild-type virus. For example, viruses having a deletion or a mutation such as a stop codon mutation, which suppresses the expression thereof, in at least one gene encoding a viral envelope protein or a coat protein can be preferably used. Such viruses that do not express an envelope protein are, for example, viruses that can replicate the genome in infected cells but cannot form infectious virus particles. Such transmission-defective viruses are suitable for production of the non-infectious virus particle. For example, viruses that do not encode any of F or HN gene of envelope protein (spike protein) or F and HN genes in the genome can be used (WO 00/70055 and WO 00/70070; Li, H.-O. et al., J. Virol. 74(14) 6564-6569 (2000)). If proteins necessary for genome replication (for example, N, P, and L proteins) are encoded in the genomic RNA, the genome can be amplified in infected cells. To produce an envelope protein-defective infectious virus particle, for example, the defective gene product or a protein that can complement it is externally supplied in the virus-producing cell (WO 00/70055 and WO 00/70070; Li, H.-O. et al., J. Virol. 74(14) 6564-6569 (2000)). Meanwhile, when the defective viral protein is not complemented at all, the non-infectious virus particle can be collected (WO 00/70070).

Further, in production of the virus of the present invention, a virus carrying a mutant-type viral protein gene is also preferably used. For example, in the structural proteins (NP, M) or RNA polymerase (P, L) of the virus, many mutations including attenuation mutations and temperature-sensitive mutations are known. The paramyxoviruses having these mutant protein genes can be used favorably in accordance with the purpose in the present invention. In the present invention, viruses with lowered cytotoxicity may be desirably used. Cytotoxicity can be measured, for example, by quantifying the release of lactic acid dehydrogenase (LDH) from cells. Regarding the degree of lowering of cytotoxicity, for example, viruses showing a significant decrease of, for example, 20% or more, 25% or more, 30% or more, 35% or more, 40% or more, or 50% or more in the LDH release level compared to the wild-type in a culture solution of human-derived HeLa cell (ATCC CCL-2) or simian-derived CV-1 cell (ATCC CCL 70) infected at multiplicity of infection (MOI) 3 and cultured for three days can be used. Further, mutations that decrease cytotoxicity also include temperature-sensitive mutations. The temperature-sensitive mutations refer to mutations which significantly decrease the activity at the viral host's ordinary temperature (for example, 37° C. to 38° C.) when compared to that at a low temperature (30° C. to 36° C., for example, 30° C. to 32° C.). Such proteins with temperature-sensitive mutations are useful since the viruses can be produced under permissive temperatures (low temperatures). When infected at 37° C., the viruses having useful temperature-sensitive mutations in the present invention show a growth rate or gene expression level of at least ½ or less, preferably ⅓ or less, more preferably ⅕ or less, more preferably ¹⁄₁₀ or less, and more preferably ¹⁄₂₀ or less, for example, compared to when cultured cells are infected at 32° C.

The virus used in the present invention may encode an exogenous gene or a regulatory factor controlling the properties of the virus, in addition to the viral protein gene, in the genome. For example, a degron sequence or a target sequence of miRNA may be encoded in order to adjust the expression of the viral protein.

Further, the paramyxovirus used in the present invention may be wild type as long as it does not inhibit production of the non-infectious virus particle and expresses an expression product of the antigen gene on the particle. In the paramyxovirus suitably used in the present invention, at least one envelope gene is deleted or mutated. Such a virus includes viruses in which at least one envelope gene is deleted, at least one envelope gene is mutated, and at least one envelope gene is mutated and at least one envelope gene is deleted. The at least one envelope gene which is mutated or deleted is preferably a gene encoding an envelope constituent protein, and examples thereof include F gene and/or HN gene. For example, a virus in which F gene has been deleted or F gene encodes a loss-of-function mutant F protein can be suitably used. Further, a virus in which HN gene has been deleted or HN gene encodes a loss-of-function mutant HN protein may be used. Furthermore, for example, paramyxovirus in which F gene has been deleted and HN gene has been further deleted or HN gene is further mutated is suitably used in the present invention. Furthermore, for example, paramyxovirus in which F gene has been deleted and HN gene has been further deleted is also suitably used in the present invention. Such mutant-type viruses can be produced according to a known method. Further, the paramyxovirus of the present invention preferably has M gene.

The non-infectious virus particle of the present invention expresses an antigen molecule on the surface (that is, holds an antigen molecule on the surface). The antigen molecule is a molecule that evokes immune reaction with respect to the antigen in humans and animals when the non-infectious virus particle is administered, and examples thereof include a pathogen-derived structural protein or a viral protein essential in amplification of pathogens. Of pathogens, in order to inhibit infection of pathogenic virus, an envelope protein expressed on the surface of the virus particle is suitably used as the antigen. Examples of a virus holding envelope, other than various viruses of Paramyxoviridae mentioned above, include viruses belonging to Filoviridae such as Ebola virus classified into Mononegavirales, Rhabdoviridae such as rabies virus, Bunyaviridae, and Arenaviridae such as Lassa virus, and further include viruses belonging to Orthomyxoviridae having segmented negative strand RNA as genome, Flaviviridae having positive strand RNA as genome, Togaviridae, Retroviridae, Coronaviridae, Hepadnaviridae such as type B hepatitis virus having double strand DNA as genome, Herpesviridae, and Poxviridae such as smallpox virus. As the pathogen, particularly, T cell infectious viruses such as HIV and HTLV are exemplified. Both HIV-1 and HTLV-1 are enveloped viruses belonging to Retroviridae.

These enveloped viruses recognize target cells and infect the cells via the envelope protein on the surface of the particle thereof. Thus, a vaccine that induces an antibody that binds to the envelope protein on the surface of the particle and inhibits cell infection of the virus is considered to be effective for infection inhibition. That is, the paramyxovirus non-infectious particle of the present invention includes those in which all or part of an envelope protein of the pathogenic virus is expressed as the antigen protein on the surface of the particle. Herein, the length of part of the envelope protein is not limited as long as the envelope protein exhibits immunogenicity. As described above, an antigen protein containing one or more epitopes and being capable of inducing antigen-specific immune response by stimulating the immune system of a host can be appropriately used, and the antigen protein typically contains at least 7 to 15 amino acids, for example, 8, 9, 10, 12, or 14 amino acids. Such an antigen protein preferably contains part or all of ectodomain (extracellular domain) of the envelope protein. More preferably, the paramyxovirus non-infectious particle of the present invention comprises at least 20% or more, preferably 50% or more, 60% or more, 70% or more, 80% or more, or 90% or more of the entire amino acid sequence in the ectodomain of the envelope protein of the pathogenic virus or comprises the entire sequence. By expressing the envelope protein antigen of the target virus on the surface of the particle, it is possible to produce a vaccine effective for infection inhibition. The antigen protein may be a natural protein, a fraction thereof, a fusion protein including the fraction, or the like. The fusion protein is, for example, a fusion protein of the fraction and an envelope protein (part or all of the envelope protein may be employed) of another virus (for example, paramyxovirus).

However, the envelope protein of the virus may be difficult to express on the surface of a different virus particle in some cases. In order to solve this problem, the present inventors produced a gene in which the part presented outside a cell of the antigen envelope molecule is fused with the part inside a cell of the envelope molecule of paramyxovirus from which the non-infectious particle of the present invention is derived, and caused this gene to be carried in viral genome. It was confirmed that a fusion protein expressed from the fusion gene produced in this way is efficiently incorporated onto the non-infectious virus particle. As the antigen protein of the present invention, a fusion protein containing an antigen fragment of pathogen at the outer side of the virus particle and the cytoplasmic region fragment of the envelope protein of paramyxovirus at the inner side of the virus particle is suitably used.

For example, as the antigen protein of heterologous pathogen which is expressed on the particle surface of the paramyxovirus non-infectious particle of the present invention, a fusion protein containing an antigen of heterologous pathogen at the outer side of the membrane of the particle and the inside-particle part of the envelope protein of the paramyxovirus at the inner side of the membrane of the particle can be suitably used. In a case where the antigen protein is an antigen protein of pathogenic virus, as the antigen part, the ectodomain (extracellular domain when expressed in cells) of the envelope protein can be used. As the inside-particle part of the envelope protein of paramyxovirus, a cytoplasmic region when the envelope protein is expressed in cells can be used. The ectodomain and the cytoplasm region used in the fusion protein may not be a full length or may be a partial fragment, respectively. The transmembrane domain of the fusion protein may be derived from any one, and preferably, is a transmembrane domain of paramyxovirus protein, and the transmembrane domain of the same envelope protein as in the above-described cytoplasm region is more preferably used.

The envelope gene of retrovirus encodes an envelope protein precursor that is a type I transmembrane protein. This precursor undergoes modification such as glycosylation by Golgi apparatus, is then transferred onto the cell surface by the signal peptide at the amino terminal, processed by protease, and divided into two subunits that are the extracellular domain (SU) and the transmembrane domain (TM). The SU interacts with the extracellular domain of TM to form a complex on the cell membrane, and this complex forms a trimer to become an active envelope protein. It is considered that this trimer is incorporated into the virus particle when the virus particle buds by interaction with MA protein, which is a scaffold protein of retrovirus, via the cytoplasm part of TM.

In a case where the antigen protein of heterologous pathogen which is expressed on the particle surface of the non-infectious particle of the present invention is derived from the type I transmembrane protein like the envelope protein of retrovirus as described above, as the envelope protein of paramyxovirus to be fused, the type I transmembrane protein is preferably selected, and in a case where the antigen protein of the heterologous pathogen is derived from a type II transmembrane protein, as the envelope protein of paramyxovirus to be fused, the type II transmembrane protein is preferably selected. For example, in a case where the envelope protein of the retrovirus is selected as the antigen protein, the ectodomain thereof is preferably fused with the intracellular domain of F protein of paramyxovirus (including the transmembrane domain (TM)). Incidentally, in a case where a fusion protein is expressed using the envelope protein of retrovirus as the antigen, in order to easily form a trimer, at least C terminal of the ectodomain of the envelope protein of the retrovirus is preferably included, and more preferably, 50 amino acids or more, preferably 60 amino acids or more, 70 amino acids or more, 80 amino acids or more, 90 amino acids or more, 100 amino acids or more, 120 amino acids or more, 150 amino acids or more, 200 amino acids or more, or 250 amino acids or more of the ectodomain including the C terminal of the ectodomain is preferably included. Further, the N terminal of the TM region of the envelope protein of the retrovirus is more preferably included, and more preferably, 50 amino acids or more, preferably 60 amino acids or more, 70 amino acids or more, 80 amino acids or more, 90 amino acids or more, 100 amino acids or more, or 120 amino acids or more of the TM region side including the N terminal of the TM region is preferably included.

Further, preferably, the protein preferably includes a protease cleavage site that is present between the ectodomain and the TM of the envelope protein of the retrovirus and is preferably cleaved at the cleavage site.

The gene encoding the antigen protein can be inserted into a desired position of the paramyxovirus genome. In the case of paramyxovirus, since an increase in expression level can be expected as approaching the 3'-terminal of the genome, for example, a nucleotide sequence encoding the antigen protein can be inserted between the leader sequence at the 3'-terminal and the gene of the first paramyxovirus protein (typically N protein) at the 5'-side thereof. Alternatively, the insertion site may be a site between the gene of the first paramyxovirus protein (typically N protein) and the gene of the second paramyxovirus protein (typically P protein), a site between the gene of the second paramyxovirus protein and the gene of the third paramyxovirus protein (typically between P and M), or the like.

Figure 1:
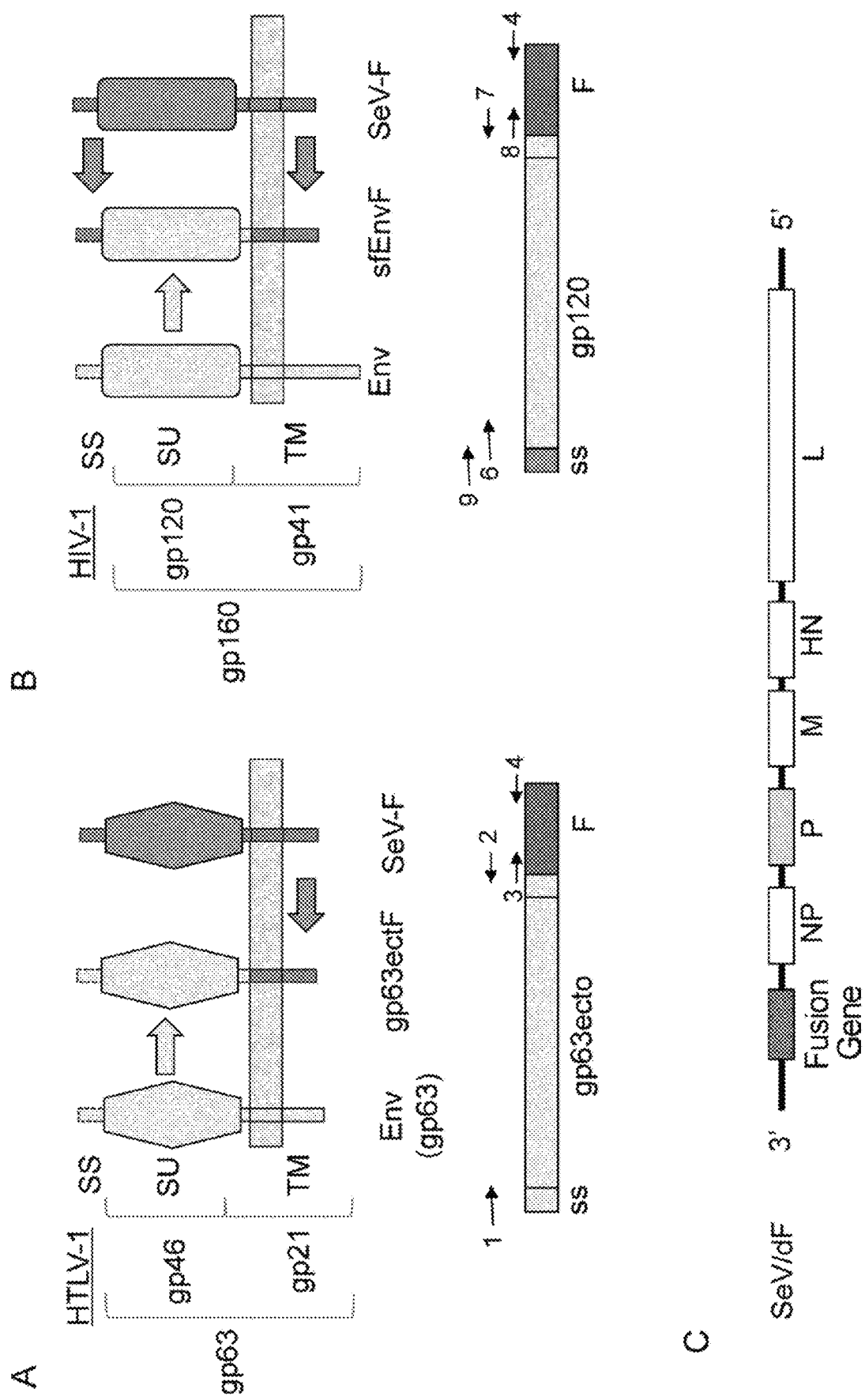
FIG. 1 is a concept diagram of the construction of an antigen carrying a non-infectious particle (HIV-1/HTLV-1 envelope). A: Construction of gp63ectoF fusion gene. B: Construction of sfEnvF fusion gene. The upper diagram is a schematic diagram illustrating a state in which fusion protein encoded by a fusion gene is expressed on a cell membrane. ss: signal peptide, SU: extracellular domain, TM: cellular transmembrane domain. The lower diagram is a schematic diagram of a fusion gene. Arrows represent positions of primers used in construction of the fusion gene and numbers represent sequence numbers. 1: Not1_gp63ecto_N, 2: gp63ectoF_C, 3: gp63ectoF_N, 4: sfEnvF_EIS_Not1_C, 6: sfEnv_N1, 7: EnvF_C, 8: EnvF_N, 9: sf_N2. C: a diagram showing a position of the fusion gene carried on the genome of SeV/dF vector.

The envelope gene of HTLV-1 consists of cording sequences of 1467 bases and encodes an envelope protein precursor (gp63) consisting of 488 amino acids in the case of the strain used in Examples of the present specification, which was isolated from the blood cell of an HTLV-1 infected patient (National Institute of Infectious Diseases). This precursor is processed by protease and then divided into the extracellular domain (gp43, SU, amino acids 1 to 322) and the transmembrane domain (gp21, TM, amino acid 323-488). In Examples of the present specification, a gene (called "gp63ectoF") in which nucleotide sequences corresponding to amino acids 1 to 442 of gp63 (called "gp63ecto") encompassing the protease cleavage site are fused with a gene of the transmembrane domain of Sendai virus F protein was prepared (FIG. 1A), and this gene was inserted into the insertion site (18+ position) at the upstream (3'-side) of the part corresponding to the N terminal of Sendai virus protein (typically N protein) encoded at the upstream-most (3'-side) of the F-deficient Sendai virus genome (FIG. 1C).

Preparation of the fusion gene gp63ectoF was carried out as follows. Specifically, first, a gene fragment encoding gp63ecto (SEQ ID NO: 10) was prepared by a PCR method using, as a template, a plasmid (pCXSN-gp63efoldo, National Institute of Infectious Diseases) carrying a proviral sequence of HTLV-1 amplified using the PCR method using blood cell DNA of an HTLV-1 infected patient. Separately, a gene fragment corresponding to the transmembrane domain and the subsequent domain (also including the cytoplasm region) of Sendai virus F protein (amino acids 496 to 565 of Accession No. AAB06281.1; SEQ ID NO: 11) was prepared by a PCR method using, as a template, a plasmid encoding the sequence of the Sendai virus. At this time, the downstream primer for gp63ecto gene amplification and the upstream primer for amplification of the cellular transmembrane domain of the Sendai virus F protein were designed so that they straddle the boundary portion of the target fusion gene and have portions complementary to each other. Next, two prepared gene fragments were mixed and the PCR was carried out again to thereby prepare a fusion gene gp63ectoF (SEQ ID NOs: 12 and 13) comprising gp63ecto and amino acids 496 to 565 of the Sendai virus F protein. At this time, the NotI recognition sequence for facilitating the insertion to the Sendai virus vector was introduced at the upstream and the downstream of the fragment comprising the fusion gene.

Examples of a preferred aspect of the fusion protein including the envelope antigen protein of HTLV-1 include a fusion protein which includes the extracellular domain of envelope protein (mature type) of HTLV-1 and the fragment of envelope protein of HTLV-1 comprising at least 50 amino acids or more (preferably 60 amino acids or more, 70 amino acids or more, 80 amino acids or more, 90 amino acids or more, 100 amino acids or more, or 120 amino acids or more) from the N-terminal of the TM region, and at the C-terminal side thereof, the transmembrane domain and the intracellular domain of paramyxovirus F protein. Incidentally, a signal sequence of the paramyxovirus envelope protein may be added to the N terminal of the fusion protein. Examples of the signal peptide include a signal peptide (SEQ ID NO: 15) of Sendai virus, but the signal peptide is not limited thereto. Further, a linker or a spacer (for example, a sequence consisting of one or more amino acids) may be appropriately inserted to each boundary portion of the fusion protein. Preferably, a fusion protein that is a protein comprising amino acid sequences at the 1st to 322nd positions, preferably the 1st to 442nd positions, of SEQ ID NO: 10 or a sequence in the region homologous thereto, and comprising an amino acid sequence of SEQ ID NO: 11 or a sequence in the region homologous to the sequence at the C-terminal side thereof, and for example, comprising an amino acid sequence described in SEQ ID NO: 13 is exemplified.

Herein, the homologous region refers to a corresponding region in the amino acid sequence of a virus of a different strain. The viruses are generally rich in diversity, and the amino acid sequence of the envelope protein varies depending on the isolated strain in some cases. The present invention includes a virus of a desired strain and the sequences described above are merely an example. Even in virus strains having different sequences, the present invention can be carried out using the sequence of the homologous region described above, and the like. The homologous region can be identified by preparing alignment of the amino acid sequences, for example, using a computer program or the like.

Preferred examples of the fusion protein include, without limitation, proteins that include an amino acid sequence having 60% or more, 70% or more, 80% or more, preferably 85% or more, 90% or more, 95% or more, 97% or more, 98% or more, or 99% or more identity to the amino acid sequence shown in SEQ ID NO: 13 and can be expressed on the cell membrane. The sequence identity can be determined using, for example, the BLASTP program (Altschul, S. F. et al., J. Mol. Biol. 215: 403-410, 1990). For example, a search can be carried out using default parameters in the Web page of BLAST at National Center for Biotchnology Information (NCBI) (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; Zhang J. & Madden T. L., Genome Res. 7:649-656, 1997). For example, alignment of two sequences can be produced, for example, by the Blast2sequences program which compares two sequences (Tatiana A et al., FEMS Microbiol Lett. 174:247-250, 1999) and the homology of the sequences can be determined. Gaps and mismatches are treated similarly, and for example, a value of homology with respect to the entire amino acid sequence of secreted matured protein is calculated.

In the case of HIV-1, the envelope protein precursor gp160 (Accession No. ABA61516.1) of BG505 strain (Wu et al. J. Virol. 80 (2), 835-844 (2006)) used in Examples of the present invention comprises 860 amino acids. This precursor is divided into the extracellular domain (gp120, SU, amino acids 1 to 508) and the transmembrane domain (gp41, TM, amino acids 509 to 860) after processing with protease. In Examples, a gene in which a gene of the transmembrane domain (amino acids 496 to 565 of Accession No. AAB06281.1, also including at least a cytoplasm region, SEQ ID NO: 12) of the Sendai virus F protein is fused with a nucleotide sequence corresponding to amino acids 30 to 680 (SEQ ID NO: 14) of gp160 excluding signal peptide (amino acids 1 to 29) was prepared. At this time, simultaneously, the signal peptide (amino acids 1 to 26 of Accession No. AAB06281.1, SEQ ID NO: 15) of Sendai virus was added to the N terminal through a linker consisting of two amino acid residues (AS) (FIG. 1B). The prepared fusion gene (called "sfEnvF," SEQ ID NO: 16) was inserted into the insertion site (18+position) at the N terminal of F-deficient Sendai virus vector genome (FIG. 1C).

Preparation of the sfEnvF fusion gene was carried out as follows. Specifically, first, a gene fragment corresponding to amino acids 30 to 680 of gp160 was prepared by a PCR method using, as a template, a plasmid encoding Env gene of HIV-1 BG505 strain, and separately, a gene fragment corresponding to the transmembrane domain of Sendai virus F protein was prepared by a PCR method using, as a template, a plasmid encoding the sequence of the Sendai virus. At this time, the downstream primer for gp160 gene amplification and the upstream primer for amplification of the transmembrane domain of the Sendai virus F protein were designed so that they straddle the boundary portion of the target fusion gene and have portions complementary to each other. Next, two prepared gene fragments were mixed and the PCR was carried out again to thereby prepare a fusion gene comprising amino acids 30 to 680 of gp160 and amino acids 496 to 565 of the Sendai virus F protein. At this time, by using a primer comprising the signal peptide of Sendai virus and the sequence corresponding to the linker as the upstream primer, the signal peptide of the Sendai virus was added to the fusion gene. Further, simultaneously, the NotI recognition sequence for facilitating the insertion to the Sendai virus vector was introduced at the upstream and the downstream of the fragment comprising the fusion gene.

Further, envelope protein precursor gp160 (Accession No. KM082921.1) of AD8EO strain (Shingai, M. et al., 2012, Proc Natl Acad Sci U.S.A. 109(48): 19769-19774) can also be used. This precursor is divided into the extracellular domain (gp120, SU, amino acids 1 to 504) and the transmembrane domain (gp41, TM, amino acids 505 to 850) after processing with protease. In Examples, a gene in which the gene of the transmembrane domain (amino acids 496 to 565 of Accession No. AAB06281.1, also including a part of the cytoplasm region, SEQ ID NO: 12) of the Sendai virus F protein is fused with the nucleotide sequence corresponding to amino acids 32 to 677 (SEQ ID NO: 28) of gp160, excluding signal peptide (amino acids 1 to 31), was prepared. At this time, simultaneously, the signal peptide (amino acids 1 to 26 of Accession No. AAB06281.1, SEQ ID NO: 15) of the Sendai virus was added to the N terminal through a linker consisting of two amino acid residues (AS). The prepared fusion gene (called "sfAD8EOEnvF," the amino acid sequence is SEQ ID NO: 29) was inserted into the insertion site (18+ position) at the N terminal of F-deficient Sendai virus vector genome.

A preferred aspect of the fusion protein including the envelope antigen protein of HIV-1 is similar to the case of HTLV-1 described above, and for example, a fusion protein, which includes the extracellular domain of envelope protein (mature type) plus a part of envelope protein fragment of HIV-1 comprising at least 50 amino acids or more (preferably 60 amino acids or more, 70 amino acids or more, 80 amino acids or more, 90 amino acids or more, 100 amino acids or more, 120 amino acids or more, 200 amino acids or more, 300 amino acids or more, 400 amino acids or more, 500 amino acids or more, or 600 amino acids or more) from the N-terminal of the TM domain, and at the C-terminal thereof, the transmembrane domain and the cytoplasmic domain of paramyxovirus F protein, is exemplified. Incidentally, the signal sequence of the paramyxovirus envelope protein may be added to the N terminal of the fusion protein. Examples of the signal peptide include a signal peptide (SEQ ID NO: 15) of Sendai virus, but the signal peptide is not limited thereto. Further, a linker or a spacer (for example, a sequence consisting of one or more amino acids) may be appropriately inserted to each boundary portion of the fusion protein. Preferably, a fusion protein that is a protein comprising the amino acid sequence at the 1st to 479th positions, preferably the 1st to 651st positions, of SEQ ID NO: 14 or a sequence in a region homologous to the sequence, and comprising the amino acid sequence of SEQ ID NO: 11 or a sequence in a region homologous to the sequence at the C-terminal thereof, and for example, comprising the amino acid sequence at the 29th to 749th positions of SEQ ID NO: 17, is exemplified. The sequence in the homologous region is as described above, and can be easily determined by a person skilled in the art.

For example, in the case of using the AD8EO strain of HIV-1 as an example, preferably, a fusion protein that is a protein comprising the amino acid sequence at the 1st to 473rd positions, preferably the 1st to 646th positions, of SEQ ID NO: 28 or a sequence in a region homologous to the sequence, and the amino acid sequence of SEQ ID NO: 29 or a sequence in a region homologous to the sequence at the C-terminal thereof, for example, the amino acid sequence at the 31st to 746th positions of SEQ ID NO: 29, is exemplified. The sequence in the homology region is as described above, and can be easily determined by a person skilled in the art.

The envelope protein of the HIV virus is rich in diversity, and the amino acid sequence and the size of the protein may vary depending on the isolated strain. However, the present invention includes a desired strain and is not limited to the sequence described above. Even with strains having different sequences, the present invention can be carried out using the sequence of the homologous region described above, and the like.

Preferred examples of the fusion protein regarding the envelope protein of HIV-1 include, without limitation, proteins comprising an amino acid sequence having 60% or more, 70% or more, 80% or more, preferably 85% or more, 90% or more, or 95% or more, 97% or more, 98% or more, or 99% or more identity to the amino acid sequence shown in SEQ ID NO: 17 or 29 that are proteins having the function of being expressed on the cell membrane. The sequence identity can be determined as described above, for example, using BLASTP program.

Insertion of fusion gene gp63ectoF, or sfEnvF or sfAD8EOEnvF into the F-deficient Sendai virus vector genome, and amplification and recovery of the viral vector were carried out using known methods (WO 97/16539; WO 97/16538; WO 00/70070; WO 01/18223; WO 2005/071092; Hasan, M K et al. J Gen Virol 78:2813-2820, 1997; Kato A et al. EMBO J 16: 578-587, 1997; Yu D et al. Genes Cells 2: 457-466, 1997; Kato A et al., Genes Cells 1; 569-579, 1996; Tokusumi T et al. Virus Res 86:33-38, 2002; Li H O et al., J Virol 74: 6564-6569, 2000). The viral vector and the virus particle of the present invention can also be obtained similarly thereto.

In a preferred embodiment, the amount of the pathogen antigen protein contained in the particle increases in the non-infectious particle of the present invention as compared to the infectious particle. That is, the present invention provides a particle that is the non-infectious particle of the present invention and in which the amount of the antigen protein contained in the particle increases as compared to the infectious particle. Herein, the pathogen antigen protein contained in the particle also includes a pathogen antigen protein expressed on the membrane surface of the particle. Further, in the non-infectious particle of the present invention, preferably, as compared to the infectious particle, the amount of the pathogen antigen protein on the surface of the particle increases. The infectious particle to be compared is a virus particle having the same genome as that of the non-infectious particle of the present invention, or a virus particle having genome, which carries an envelope protein gene imparting infectiveness to the genome, can be suitably used. For example, in the case of the non-infectious particle in which the envelope protein gene on the genome is deleted, a virus particle having the same genome sequence except that the envelope protein gene is not deleted can be used as a target to be compared. In the non-infectious particle of the present invention, the amount of the pathogen antigen protein is, for example, 1.2 times or more, preferably 1.5 times or more, 1.8 times or more, 2 times or more, 2.5 times or more, 3 times or more, 4 times or more, 5 times or more, 6 times or more, 7 times or more, or 8 times or more, as compared to the infectious particle. Regarding comparison of the amount of the pathogen antigen protein, for example, comparison may be carried out per particle, per unit weight of the particle, or per the amount of nucleic acid contained in the particle, and preferably, comparison is carried out with the amount of the pathogen antigen protein per one particle. The amount of the pathogen antigen protein can be measured by known methods such as ELISA and western blotting.

Further, the present invention relates to a paramyxovirus vector that is a paramyxovirus vector in which at least one envelope protein gene has been deleted from the genome and which carries an antigen protein gene of a heterologous pathogen. The viral vector is preferably a vector having a genome replicative capacity and a particle forming capacity in introduced cells and carries the N, P, and L genes on the genome. Furthermore, the viral vector preferably carries the M gene on the genome. The viral vector is useful for producing the non-infectious virus particle of the present invention, and the viral vector itself can be used as a vaccine. In this case, the viral vector preferably expresses the antigen protein gene of the heterologous pathogen on the surface of the virus particle. That is, the viral vector holds the antigen protein of the heterologous pathogen on the surface of the virus particle.

In particular, the present invention succeeded for the first time in providing a paramyxovirus vector expressing envelope antigen protein derived from HTLV on the surface of the virus particle. The paramyxovirus vector expressing the HTLV envelope antigen protein of the present invention includes a high-level HTLV envelope antigen protein in the particle, and can induce immune reaction efficiently either in the form of infectious virus particle or non-infectious virus particle. Therefore, the infectious viral vector and the non-infectious virus particle of the present invention that hold the HTLV envelope antigen protein on the surface of the virus particle are useful as a vaccine for prevention and/or treatment of infection of HTLV or diseases caused by infection.

The description of the aforementioned non-infectious virus particle is applicable as is to the envelope protein gene that is deleted from the genome, and the antigen protein of heterologous pathogen. For example, the F gene and/or the HN gene may be deleted, and preferably, at least the F gene is deleted. Further, the M gene may be held. The antigen protein of heterologous pathogen may be a natural protein, a fragment thereof, a fusion protein including the fragment, or the like. The antigen protein of heterologous pathogen is, as described above, preferably a membrane protein that includes an antigen of heterologous pathogen at the outer side of the membrane of the particle, and is a fusion protein including the inside-particle part of the envelope protein of paramyxovirus at the inner side of the membrane of the particle. For example, a fusion protein including the ectodomain of the envelope protein of a pathogenic virus, and the transmembrane domain and the cytoplasm region of the envelope protein of paramyxovirus is preferred. The ectodomain and the cytoplasmic region may not be a full length or may be a partial fragment (for example, including 30% or more, 40% or more, 50% or more, 60% or more, 70% or more, 80% or more, 90% or more, or 95% or more of the full length).

In order to produce an infectious particle from the paramyxovirus vector, the envelope protein deleted in the genome of the viral vector may be supplied in the cell introduced with the viral vector. The envelope protein may be transiently or constitutively expressed in a viral vector producing cell. In order to constitutively express the envelope protein, a gene encoding the envelope protein can be introduced to the chromosome of the cell. In order to transiently express the envelope protein, a gene encoding the envelope protein can be introduced using an expressing plasmid vector or another desired vector, or the envelope protein gene introduced to the chromosome of the cell can be expressed at a specific timing using a system such as Cre-loxP. Further, in order to produce a non-infectious particle, the viral vector is introduced into cells that are not expressing the envelope protein deleted in the genome of the viral vector.

Further, the present invention relates to a composition containing the paramyxovirus vector of the present invention. The composition is, for example, a composition containing the paramyxovirus vector of the present invention and a desired carrier. Further, the present invention relates to a composition containing the non-infectious particle of the present invention. The composition is, for example, a composition containing the non-infectious particle and a desired carrier. The carrier may be a desired pharmaceutically acceptable carrier, and examples thereof include desired solution that can suspend the paramyxovirus vector or the non-infectious particle of the present invention, such as sterilized water, saline, phosphate buffered saline (PBS), a buffer solution, and a culture solution. Furthermore, the present invention relates to a vaccine formulation containing the paramyxovirus vector or the non-infectious particle of the present invention. The vaccine formulation of the present invention can efficiently induce an immune response to the antigen protein of pathogen, and thus is particularly useful as a vaccine for prevention and treatment against the pathogen. The vaccine formulation of the present invention can be prepared, for example, as a composition containing the paramyxovirus vector or the non-infectious particle of the present invention. Furthermore, an adjuvant or adjuvants may be further contained.

The form of inoculation of the vaccine formulation of the present invention is not particularly limited, and for example, single-time inoculation or multiple-time inoculation can be used. In the multiple-time inoculation, the vaccine of the present invention may be inoculated in multiple times or may be used in combination with another type vaccine. For example, in the primary inoculation, inoculation is carried out using, as a vaccine formulation, a viral vector having the ability to produce an infectious virus particle in inoculated cells, and in the booster inoculation, a vaccine formulation containing the non-infectious particle of the present invention may be inoculated. Since the non-infectious particle does not produce an infectious particle, the non-infectious particle has high safety and is particularly suitable for performing the booster inoculation in multiple times (for example, 2 times or more, 3 times or more, 4 times or more, or 5 times or more).

Further, the vaccine formulation of the present invention is shown to be also useful for widening the cross-reactivity of antibodies produced in an individual subjected to vaccine inoculation. For example, in a case where booster inoculation is performed using the vaccine formulation of the present invention, a vaccine formulation containing an antigen different from the antigen included in the vaccine formulation used in the primary inoculation can be used. For example, even in the case of an antigen of the same pathogen, a protein different from the antigen used in the primary inoculation can be used as the antigen, or even in the case of the same protein, a part different from the antigen used in the primary inoculation can be used as the antigen or a protein of pathogen different from the pathogen to which the antigen used in the primary inoculation belongs can be used as the antigen. In particular, even in the case of the same species of pathogen, when a strain different from the pathogen from which the vaccine formulation used in the primary inoculation is derived is used in the booster inoculation of the present invention, cross-reactivity with respect to the pathogen can be significantly increased (see Example 10). Specifically, for example, in a case where the Env protein of an enveloped virus is used as the antigen, when the vaccine formulation of the present invention, which is produced using a non-infectious particle containing, as the antigen, the Env protein of a strain different from the virus strain from which the Env protein used in the primary inoculation is derived, is used in the booster inoculation, high immune reaction of cross-reactivity can be evoked.

In a case where administration to animals is performed using the paramyxovirus vector, the non-infectious particle, the vaccine containing the paramyxovirus vector or the non-infectious particle, the composition containing the paramyxovirus vector or the non-infectious particle, or the like of the present invention, the dosage thereof can be suitably determined depending on disease, body weight, age, gender, and symptoms of the patient, the purpose of administration, the form of administered composition, the administration method, and the like. The route of administration can be suitably selected, and examples thereof include transnasal administration, intraperitoneal administration, intramuscular administration, and local administration to a tumor site. However, the route of administration is not limited thereto. Further, the dosage may be suitably adjusted depending on the animal to be administered, the administration site, the number of doses, and the like. For example, 1 ng/kg to 1000 mg/kg, 5 ng/kg to 800 mg/kg, 10 ng/kg to 500 mg/kg, 0.1 mg/kg to 400 mg/kg, 0.2 mg/kg to 300 mg/kg, 0.5 mg/kg to 200 mg/kg, or 1 mg/kg to 100 mg/kg is exemplified, but the dosage is not limited thereto. Further, for example, administration with $1\times10^4$ to $1\times10^{15}$ CIU/kg, $1\times10^5$ to $1\times10^{14}$ CIU/kg, $1\times10^6$ to $1\times10^{13}$ CIU/kg, $1\times10^7$ to $1\times10^{12}$ CIU/kg, $1\times10^8$ to $5\times10^{11}$ CIU/kg, $1\times10^9$ to $5\times10^{11}$ CIU/kg, or $1\times10^{10}$ to $1\times10^{11}$ CIU/kg, and administration with $1\times10^6$ to $1\times10^{17}$ particles/kg, $1\times10^7$ to $1\times10^{16}$ particles/kg, $1\times10^8$ to $1\times10^{15}$ particles/kg, $1\times10^9$ to $1\times10^{14}$ particles/kg, $1\times10^{10}$ to $1\times10^{13}$ particles/kg, $1\times10^{11}$ to $5\times10^{12}$ particles/kg, or $5\times10^{11}$ to $5\times10^{12}$ particles/kg are exemplified, but the dosage is not limited thereto.

The administration targets of the composition comprising the vector of the present invention are preferably mammals (including human and nonhuman mammals). Specific examples include humans, non-human primates such as monkeys, rodents such as mice and rats, rabbits, goats, sheep, pigs, bovine, dogs, cats, and other mammals.

EXAMPLES

[Example 1] Construction of F-Deficient Sendai Virus Carrying HTLV-1 Envelope Protein (SeV18+gp63ectoF/ΔF, SeV18+gp63ecto/ΔF)

1) Construction of Plasmid for Production of F-Deficient Sendai Virus Carrying gp63ectoF Gene (pSeV18+gp63ectoF/ΔF)

Preparation of gp63ecto gene fragment was carried out by PCR that used, as a template, a plasmid carrying the proviral sequence of HTLV-1 amplified by a PCR method with hemocyte DNA of an HTLV-1 infected patient (pHTLV-1, National Institute of Infectious Diseases). The PCR was carried out under the following conditions: 94° C. for 2 minutes, 30 cycles of (98° C. for 10 seconds, 55° C. for 30 seconds, 68° C. for 1.5 minutes), 68° C. for 5 minutes and ∞ at 4° C., using KOD-Plus-Ver. 2 with primer Not1_gp63ecto_N (5'-ATATGCGGCCGCGACGCCAC-CATGGGCAAGTTCCTGGCCACCC-3' (SEQ ID NO: 1)) and primer gp63ectoF_C (5'-CGTAAT-CACAGTCTCTCTTGAGTTAGCTTCTCTGGCC-CACTGGC-3' (SEQ ID NO: 2)), and the amplified fragment (about 1.3 kbp) was purified using the QIAquick PCR purification kit.

Preparation of the F gene fragment was carried out by PCR using, as a template, the F gene on Sendai virus genome cDNA carried on pSeV18+ (WO 00/070070; Hasan, M. K. et al., 1997, J. General Virology 78: 2813-2820; incidentally, "pSeV18+" is also referred to as "pSeV18+b (+)"). The PCR was carried out under the following conditions: 94° C. for 2 minutes, 30 cycles of (98° C. for 10 seconds, 55° C. for 30 seconds, 68° C. for 1.5 minutes), 68° C. for 5 minutes, and ∞ at 4° C., using KOD-Plus-Ver. 2 with primer gp63ectoF_N (5'-GCCAGTGGGCCAGAGAAGCTAACTCAAGAGA-GACTGTGATTACG-3' (SEQ ID NO: 3)) and primer sfEnvF_EIS_Not1_C (5'-TTAGCGGCCGCGAT-GAACTTTCACCCTAAGTTTTTCTTACTACGGT-CATCTTTTCTCAGCCATT GC-3' (SEQ ID NO: 4)), and the amplified fragment (about 0.3 kbp) was purified using the QIAquick PCR purification kit.

Construction of the gp63ectoF gene fragment was carried out by PCR using a template obtained by mixing the aforementioned gp63ecto gene fragment and the F gene fragment prepared by the PCR. The PCR was carried out under the following conditions: 94° C. for 2 minutes, 30 cycles of (98° C. for 10 seconds, 55° C. for 30 seconds, 68° C. for 1.5 minutes), 68° C. for 2 minutes, and ∞ at 4° C., using KOD-Plus-Ver. 2 with primer Not1_gp63ecto_N and primer sfEnvF_EIS_Not1_C, and the amplified fragment (about 1.6 kbp) was purified using the QIAquick PCR purification kit. This fragment encodes the fusion protein in which the TM region and the cytoplasm region of the SeV F protein are fused at the C-terminal of the ectodomain of gp63 (including parts of SU and TM).

Then, the above-described gp63ectoF fragment subjected to the NotI treatment (having NotI sites at both ends) was ligated to the NotI-cleaved site of pSeV18+/ΔF plasmid (WO 00/070070) having an insertion site (NotI-cleavage site) of carried gene upstream of the NP gene of the F-deficient Sendai virus genome, and was subjected to cloning after being transformed into E. coli, and correct clones of nucleotide sequences were selected by sequencing, thereby obtaining pSeV18+gp63ectoF/ΔF plasmid. Incidentally, "ΔF" is also described as "dF."

2) Construction of Plasmid for Preparing F-Deficient Sendai Virus Carrying gp63ecto Gene (pSeV18+gp63ecto/ΔF)

Preparation of gp63ecto gene fragment encoding a protein in which the C terminal of the SeV F protein was not fused was carried out by PCR using, as a template, HTLV-1 provirus carried in the plasmid (pHTLV-1) (Seiki, M. et al. Proc. Natl. Acad. Sci. U.S.A. 80 (12), 3618-3622 (1983)). The PCR was carried out under the following conditions: 94° C. for 2 minutes, 30 cycles of (98° C. for 10 seconds, 55° C. for 30 seconds, 68° C. for 1.5 minutes), 68° C. for 5 minutes, and ∞ at 4° C., using KOD-Plus-Ver. 2 with primer NotI_gp63ecto_N (SEQ ID NO: 1) and primer gp63ecto EIS_NotI_C (5'-ATATGCGGCCGCGATGAACTTT-CACCCTAAGTTTTTCTTACTACGGT-CAAGCTTCTCTGGCCCA CTGGC-3' (SEQ ID NO: 5)), and the amplified gp63ecto fragment (about 1.3 kbp) was purified using the QIAquick PCR purification kit.

Then, the above-described gp63ecto fragment subjected to the NotI treatment (having NotI sites at both ends) was ligated to the NotI-cleaved site of pSeV18+/ΔF plasmid (WO 00/070070), and was subjected to cloning after being transformed into E. coli, and correct clones of nucleotide sequences were selected by sequencing, thereby obtaining pSeV18+gp63ectoΔF plasmid.

3) Preparation (Re-Construction) of F-Deficient Sendai Virus Carrying gp63ectoF Gene (SeV18+gp63ectoF/ΔF) and F-Deficient Sendai Virus Carrying gp63ecto Gene (SeV18+gp63ecto/ΔF)

One day before transfection, $5 \times 10^5$ 293 T/17 cells were seeded into each well of a 6-well plate, and cultured under a 5% $CO_2$ condition at 37° C. Using TransIT-LT1 (Mirus), the aforementioned 293T/17 cells were transfected with a mixture of pCAGGS-NP (0.5 μg), pCAGGS-P4C (−) (0.5 μg), pCAGGS-L (TDK) (2 μg), pCAGGS-17(0.5 μg), pCAGGS-F5R (0.5 μg) (see WO 2005/071085), and the plasmid for preparing SeV vector carrying gp63ectoF gene (pSeV18+gp63ectoF/ΔF) (5.0 μg) or the plasmid for preparing SeV vector carrying gp63ecto gene (pSeV18+gp63ectoF/ΔF) (5.0 μg) prepared above. The cells were cultured under a 5% $CO_2$ condition at 37° C. for two days. Then, the transfected 293T/17 cells were detached with trypsin-EDTA from the well, suspended in an MEM culture medium containing trypsin (2.5 μg/ml), penicillin, and streptomycin (hereinafter, referred to as Try/PS/MEM), and then seeded on a helper cell LLC-MK$_2$/F/Ad (Li, H.-O. et al., J. Virology 74. 6564-6569 (2000), WO 00/70070) expressing the F protein of the Sendai virus prepared in a separate well, and continuously cultured while the culture medium was exchanged every three to four days. By performing hemagglutination reaction using a part of the culture supernatant, the amount of the virus in the culture supernatant was monitored, and the culture supernatant was recovered after sufficient hemagglutination reaction was obtained. RNA was extracted from the recovered culture supernatant using the QIAamp Viral RNA Mini Kit, the carried gene (gp63ectoF or gp63ecto) region was amplified by RT-PCR using the RNA as a template, and the obtained RT-PCR product was subjected to sequencing to confirm it had the correct nucleotide sequence. The recovered culture supernatant containing the SeV18+gp63ectoF/ΔF virus or SeV18+gp63ecto/ΔF virus was snap frozen in liquid nitrogen and then stored at −80° C.

4) Amplification of F-Deficient Sendai Virus Carrying gp63ectoF Gene (SeV18+gp63ectoF/ΔF) and F-Deficient Sendai Virus Carrying gp63ecto Gene (SeV18+gp63ecto/ΔF)

The helper cell LLC-MK$_2$/F/Ad was cultured using 12 T225 flasks under a 5% $CO_2$ condition at 37° C. until the cell became semiconfluent, and infected at moi 5.0 for 1 hour using the culture supernatant containing the SeV18+gp63ectoF/ΔF virus or the SeV18+gp63ecto/ΔF virus prepared above. After infection, the culture supernatant was removed, and 30 mL of MEM culture medium containing recombinant trypsin (5.33 mrPU/ml TrypLE Select, GIBCO) and gentamicin (hereinafter, referred to as Try/GE/MEM) per flask was added and cultured under a 5% $CO_2$ condition at 32° C. A part of the culture supernatant was appropriately collected, the state of virus production was confirmed by hemagglutination assay, and the culture supernatant recovered after obtaining sufficient hemagglutination reaction was used as an infectious particle solution of the SeV18+gp63ectoF/ΔF virus and the SeV18+gp63ecto/ΔF virus.

[Example 2] Preparation of F-Deficient Sendai Virus Non-Infectious Particle Carrying HTLV-1 Envelope Protein (SeV18+gp63ectoF/ΔF NVP)

The LLC-MK2 cell was cultured using 12 T225 flasks under a 5% $CO_2$ condition at 37° C. until the cell became semiconfluent, and was infected at moi 5.0 for 1 hour using the culture supernatant containing the SeV18+gp63ectoF/ΔF virus or the SeV18+gp63ecto/ΔF virus prepared above. After infection, the culture supernatant was removed, and 30 mL of Try/GE/MEM culture medium per flask was added and cultured under a 5% $CO_2$ condition at 32° C. A part of the culture supernatant was appropriately collected, the state of virus production was confirmed by hemagglutination assay, and the culture supernatant recovered after obtaining sufficient hemagglutination reaction was used as a solution of non-infectious particles SeV18+gp63ectoF/ΔF/NVP and SeV18+gp63ecto/ΔF/NVP.

[Example 3] Construction of F-Deficient Sendai Virus Carrying HIV-1 Envelope Protein 1) Construction of Plasmid for Production of SeV Vector Carrying sfEnvF Gene (pSeV18+sfEnvF/TSΔF)

Preparation of sfEnv was carried out by PCR that uses, as a template, a plasmid carrying the Env gene of HIV-1 BG505 strain (WO 2016/069518). The PCR was carried out under the following conditions: 94° C. for 2 minutes, 30 cycles of (98° C. for 10 seconds, 55° C. for 30 seconds, 68° C. for 2 minutes), 68° C. for 5 minutes, and ∞ at 4° C., using KOD-Plus-Ver. 2 with primer sfEnv_N1 (5'-CAACATCAC-TACTGGTTGTTCTCACCACAT-TGGTCTCGTGTCAGGCTAGCGCAGAGAATTTGTG GGTAACAG-3' (SEQ ID NO: 6)) and primer Env F C (5'-CACAGTCTCTCTTGAGTTCT-TAATATACCAGAGCC-3' (SEQ ID NO: 7)), and the amplified fragment (about 2 kbp) was purified using the QIAquick PCR purification kit.

Preparation of F gene fragment was carried out using, as a template, the F gene on the Sendai virus genome cDNA carried by pSeV18+. The PCR was carried out under the following conditions: 94° C. for 2 minutes, 30 cycles of (98° C. for 10 seconds, 55° C. for 30 seconds, 68° C. for 2 minutes), 68° C. for 5 minutes, and ∞ at 4° C., using KOD-Plus-Ver. 2 with primer EnvF_N (5'-GGCTCTGGTATATTAAGAACTCAAGAGAGACTGTG-3' (SEQ ID NO: 8)) and primer sfEnvF_EIS_NotI_C (SEQ ID NO: 4)), and the amplified F gene fragment (about 0.3 kbp) was purified using the QIAquick PCR purification kit.

Next, construction of the sfEnvF gene fragment was carried out by PCR using a template obtained by mixing the aforementioned sfEnv gene fragment and the F gene fragment prepared by the PCR. The PCR was carried out under the following conditions: 94° C. for 2 minutes, 30 cycles of (98° C. for 10 seconds, 55° C. for 30 seconds, 68° C. for 2.5 minutes), 68° C. for 5 minutes, and ∞ at 4° C., using KOD-Plus-Ver. 2 with primer sf_N2 (5'-TAAGCGGCCGC-CAAGGTTCACTTATGACAGCATATATCCAGAGAT-CACAGTGCATCTCAACATC ACTACTGGTTG-3' (SEQ ID NO: 9)) and primer sfEnvF_EIS_NotI_C (SEQ ID NO: 4), and the amplified sfEnvF gene fragment (about 2.5 kbp) was purified using the QIAquick PCR purification kit. This fragment encodes the fusion protein in which the TM region and the cytoplasm region of the SeV F protein are fused at the C-terminal of the ectodomain of the HIV-1 envelope protein (including SU and a part of TM).

Then, the purified sfEnvF fragment (having NotI sites at both ends) was subjected to the NotI treatment and was ligated to the NotI-cleaved site of pSeV18+/ΔF plasmid described above, and was subjected to cloning after being transformed into E. coli, and correct clones of nucleotide sequences were selected by sequencing, thereby obtaining pSeV18+sfEnvF/ΔF plasmid.

2) Preparation (Re-Construction) of SeV Vector Carrying sfEnvF Gene (SeV18+sfEnvF/ΔF)

One day before transfection, 5×10⁵ 293 T/17 cells were seeded into each well of a 6-well plate, and cultured under a 5% CO$_2$ condition at 37° C. Using TransIT-LT1 (Mirus), the aforementioned 293T/17 cells were transfected with a mixture of pCAGGS-NP (0.5 µg), pCAGGS-P4C (–) (0.5 µg), pCAGGS-L (TDK) (2 µg), pCAGGS-T7 (0.5 µg), pCAGGS-F5R (0.5 µg) (see WO 2005/071085), and the plasmid for preparing SeV vector carrying sfEnvF gene (pSeV18+sfEnvF/ΔF) (5.0 µg) prepared above. The cells were cultured under a 5% CO$_2$ condition at 37° C. for two days. Then, the transfected 293T/17 cells were detached with trypsin-EDTA from the well, suspended in a Try/PS/MEM culture medium, and then seeded on a helper cell LLC-MK$_2$/F/Ad (Li, H.-O. et al., J. Virology 74. 6564-6569 (2000), WO 00/70070) prepared in a separate well, and continuously cultured while the culture medium was exchanged every three to four days. By performing hemagglutination reaction using a part of the culture supernatant, the amount of the virus in the culture supernatant was monitored, and the culture supernatant was recovered after sufficient hemagglutination reaction was obtained. RNA was extracted from the recovered culture supernatant using the QIAamp Viral RNA Mini Kit, the carried gene (sfEnvF or sfEnv) region was amplified by RT-PCR using the RNA as a template, and whether the obtained RT-PCR product was subjected to sequencing to confirm it had the correct nucleotide sequence. The recovered culture supernatant containing the SeV18+sfEnvF/ΔF virus was snap frozen in liquid nitrogen and then stored at –80° C.

3) Amplification of F-Deficient Sendai Virus Carrying sfEnvF Gene (SeV18+sfEnvF/ΔF)

The helper cell LLC-MK$_2$/F/Ad was cultured using 12 T225 flasks under a 5% CO$_2$ condition at 37° C. until the cell became semiconfluent, and infected at moi 5.0 for 1 hour using the culture supernatant containing the SeV18+sfEnvF/ΔF virus prepared above. After infection, the culture supernatant was removed, and 30 mL of Try/GE/MEM culture medium per flask was added and cultured under a 5% CO$_2$ condition at 32° C. A part of the culture supernatant was appropriately collected, the state of virus production was confirmed by hemagglutination assay, and the culture supernatant recovered after obtaining sufficient hemagglutination reaction was used as an infectious particle solution of SeV18+sfEnvF/ΔF virus.

[Example 4] Preparation of F-Deficient Sendai Virus Non-Infectious Particle Carrying HIV-1 Envelope Protein The LLC-MK2 cell was cultured using 12 T225 flasks under a 5% CO$_2$ condition at 37° C. until the cell became semiconfluent, and infected at moi 5.0 for 1 hour using the culture supernatant containing the SeV18+sfEnvF/ΔF virus prepared above. After infection, the culture supernatant was removed, and 30 mL of Try/GE/MEM culture medium per flask was added and cultured under a 5% CO$_2$ condition at 32° C. A part of the culture supernatant was appropriately collected, the state of vector production was confirmed by hemagglutination assay, and the culture supernatant recovered after obtaining sufficient hemagglutination reaction was used as a solution of non-infectious particle SeV18+sfEnvF/ΔF/NVP.

Figure 2:
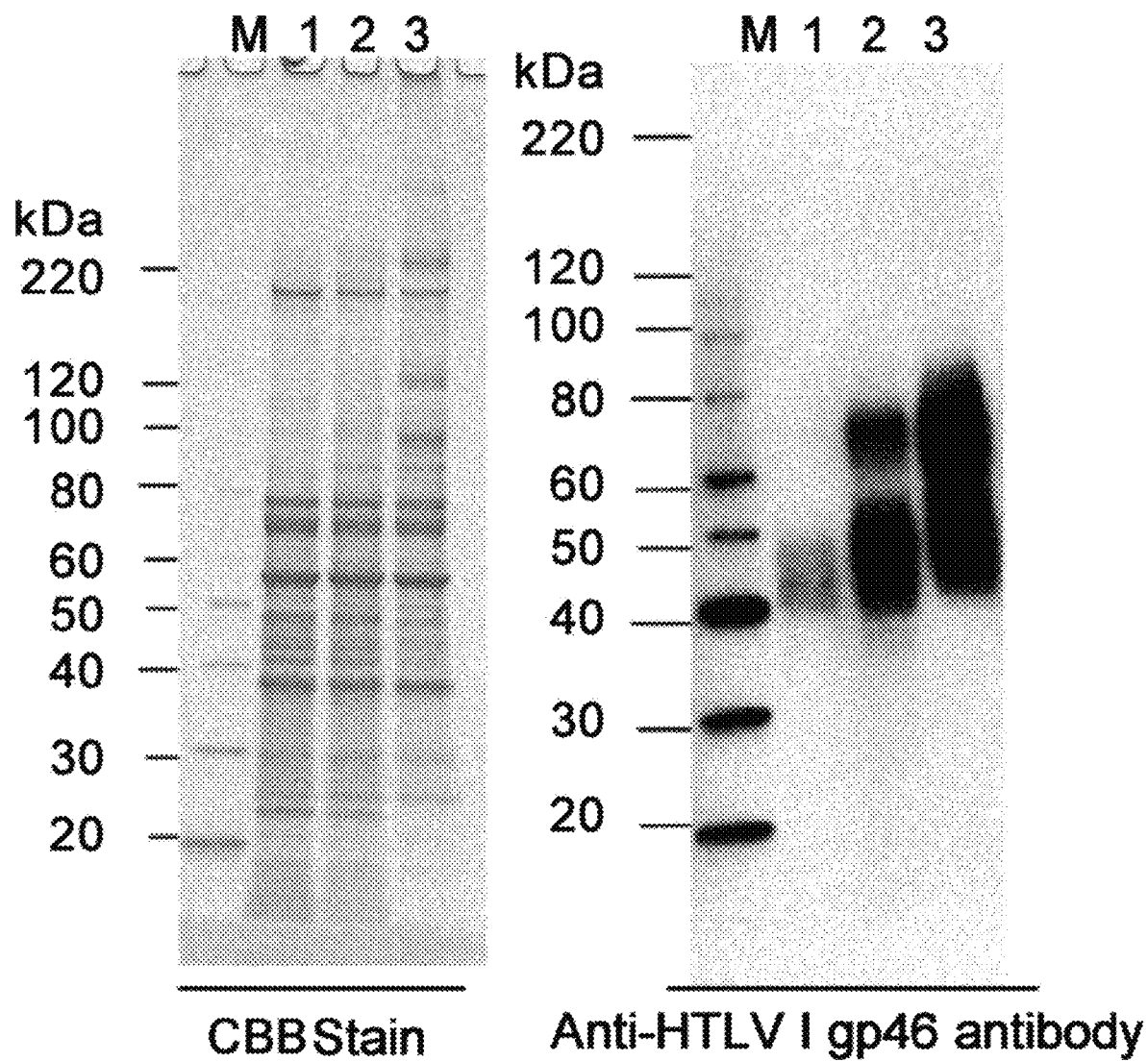
FIG. 2 shows analysis of an infectious particle and a non-infectious particle of F-deficient Sendai virus vector carrying HTLV-1 envelope protein by a western blotting method.

[Example 5] Analysis of Infectious Particle and Non-Infectious Particle of F-Deficient Sendai Virus Vector Carrying HTLV-1 Envelope Protein by the Western Blotting Method The infectious particle (SeV18+gp63ectoF/dF) and the non-infectious particle (SeV18+gp63ectoF/dF/NVP) of the F-deficient Sendai virus vector carrying HTLV-1 envelope protein were analyzed by the western blotting (WB) method. After electrophoresis (40 mA, 80 min) of 15 µl of each analyte (FIG. 2) or 1 µg as the total protein amount in acrylamide gel (5-20% wako), transfer to a nylon membrane was carried out using the electroblotting method (60 V, 2 hr). The membrane was blocked in 5% Skim Milk/0.05% Tween/TBST at 4° C. overnight, the primary antibody (anti-HTLV-1 gp46 antibody, Abcam ab9086) diluted with 0.05% Tween/TBST 2000-fold was reacted at room temperature for 1 hour, and after washing, the secondary antibody (HRP-labeled anti-mouse Ig antibody, BIOSOURCE Cat #:AMI4704) diluted with 0.05% Tween/TBST 2000-fold was reacted at room temperature for 1 hour. After washing in 0.05% Tween/TBST (5 min×3 times), detection was carried out using ECL prime (GE) (FIG. 2 and FIG. 3). The amount of the gp63ectoF protein on the non-infectious particle (SeV18+gp63ectoF/dF/NVP) significantly increased as compared to the infectious particle (SeV18+gp63ectoF/dF).

[Example 6] Analysis of Infectious Particle and Non-Infectious Particle of F-Deficient Sendai Virus Vector Carrying HIV-1 Envelope Protein by the Western Blotting Method The infectious particle (SeV18+sfEnvF/dF) and the non-infectious particle (SeV18+sfEnvF/ΔF/NVP) of the F-deficient Sendai virus vector carrying HIV-1 envelope protein were analyzed by the western blotting (WB) method. After electrophoresis (30 mA, 80 min) of each analyte in acrylamide gel (12.5% wako), transfer to a nylon membrane was carried out using the electroblotting method (60 V, 2 hr). The membrane was blocked in 5% Skim Milk/0.05% Tween/TBST at 4° C. overnight, the primary antibody (FIG. 4, panel A: anti-HIV-1 gp120 antibody (AALTO Cat #:D7324), FIG. 4, panel B: anti-Sendai virus antibody (ID Pharma)) diluted with 0.05% Tween/TBST 2000-fold was reacted at room temperature for 1 hour, and after washing, the secondary antibody diluted with 0.05% Tween/TBST (FIG. 4A: HRP-labeled anti-sheep Ig antibody (Invitrogen Cat #:618620) diluted 10,000-fold, FIG. 4B: HRP-labeled anti-rabbit Ig antibody (BIOSOURCE Cat #:ALI4404) diluted 1,000-fold) was reacted at room temperature for 1 hour. After washing in 0.05% Tween/TBST (5 min×3 times), detection was carried out using ECL prime (GE) (FIG. 4). The amount of the sfEnvF protein on the non-infectious particle (SeV18+sfEnvF/ΔF/NVP) significantly increased as compared to the infectious particle (SeV18+sfEnvF/dF).

[Example 7] Booster Effect by Non-Infectious Particle Expressing HTLV-1 Envelope Protein An immunity induction experiment was performed with mice (BALB/c) using the infectious particle (SeV18+gp63ectoF/dF) and the non-infectious particle (SeV18+gp63ectoF/dF/NVP) of F gene-deficient Sendai virus vector expressing gp63ectoF that is a fusion protein of the ectodomain of gp63 of HTLV-1 Env and the cytoplasmic domain of Sendai virus F protein. In the first group (n=6, Se group), inoculation of the infectious particle (SeV18+gp63ectoF/dF) was performed only once (week 0), in the second group (n=6, Se/VLP group), inoculation of the infectious particle (SeV18+gp63ectoF/dF) was performed once (week 0), and then inoculation of the non-infectious particle (SeV18+gp63ectoF/dF/NVP) was performed two times (weeks 4 & 5). In the inoculation of the infectious particle (SeV18+gp63ectoF/dF), $2.4 \times 10^7$ CIU (0.02 ml) was subjected to nasal inoculation, and in the inoculation of the non-infectious particle (SeV18+gp63ectoF/dF/NVP), $1.1 \times 10^{10}$ particles (0.1 ml) were subjected to intramuscular inoculation. Using blood collected at the time of euthanasia at the 8th week after the first inoculation (SeV18+gp63ectoF/dF), the anti-HTLV Env antibody titer was measured by the Western Blot (WB) and ELISA.

In the antibody titer measurement by ELISA, HTLV-1 gp46 protein (Abcam, 100 ng/0.05 ml/well) was solid-phased in each well of a 96-well plate (Corning Costar #3690), blocked with 3% BSA/PBS, mouse blood plasma was then added, and the absorbance (OD450) was measured with a plate reader after peroxidase-labeled anti-mouse IgG antibody reaction and chromogenic reaction using a TMB substrate. As a result, in data using the blood plasma diluted 1,000-fold (average value of each group of OD450 measurement value obtained by subtracting the background), the second group (0.256) showed a value 3.9 times of the first group (0.066) (FIG. 5).

In the antibody titer measurement by WB, the HTLV-1 Env gp46-binding antibody was detected using PrpBlot HTLV-1 kit (FUJIREBIO Inc. #204450) according to the protocol (using biotin-labeled anti-mouse IgG antibody). As a result, the detection limit dilution titer (geometric mean value of each group) by WB showed a 8.5 times higher value in the second group ($6.5 \times 10^2$) than in the first group ($7.6 \times 10^1$) (FIG. 6).

[Example 8] Booster Effect by Non-Infectious Particle Expressing HIV-1 Envelope Protein An immunity induction experiment was performed with mice (BALB/c) using the infectious particle (SeV18+sfEnvF/dF) and the non-infectious particle (SeV18+sfEnvF/dF/NVP) of F-deficient Sendai virus vector expressing sfEnv-F that is a fusion protein of the ectodomain of gp160 of HIV-1 (BG505) Env and the cytoplasmic domain of Sendai virus F protein. In the first group (n=4, Se group), inoculation of the infectious particle (SeV18+sfEnvF/dF) was performed only two times (weeks 0 & 1), and in the second group (n=4 [at first, n=5, but excluding one mouse due to a decrease in weight at week 1], Se/VLP group), inoculation of the infectious particle (SeV18+sfEnvF/dF) was performed two times (weeks 0 & 1) and then, inoculation of the non-infectious particle (SeV18+sfEnvF/dF/NVP) was performed two times (weeks 4 & 5). In the third group (n=5, Se/VLP/VLP group), inoculation of the infectious particle (SeV18+sfEnvF/dF) was performed two times (weeks 0 & 1) and then, inoculation of the non-infectious particle (SeV18+sfEnvF/dF/NVP) was performed four times (weeks 4, 5, 8 & 9). In the inoculation of the infectious particle (SeV18+sfEnvF/dF), $5.0 \times 10^7$ CIU (0.02 ml) was subjected to nasal inoculation, and in the inoculation of the non-infectious particle (SeV18+sfEnvF/dF/NVP), $2.0 \times 10^9$ particles (0.1 ml) were subjected to intramuscular inoculation. Using blood collected at the time of euthanasia at the 8th week (the first group and the second group) or the 12th week (the third group) after the first inoculation of the infectious particle (SeV18+sfEnvF/dF), the anti-HIV-1 Env gp120 antibody titer was measured by ELISA.

In the antibody titer measurement, HIV-1 BG505 gp120 protein (50 ng/0.05 ml/well) was solid-phased in each well of a 96-well plate (Corning Costar #3690), blocked with 3% BSA/PBS, mouse blood plasma was then added, and the absorbance (OD450) measured with a plate reader after peroxidase-labeled anti-mouse IgG antibody reaction and chromogenic reaction using a TMB substrate. As a result, in data using the blood plasma diluted 12,500-fold, average value of OD450 measurement value for each group after subtracting the background), the second group (0.475) showed a value 3.0 times the first group (0.157) and the third group (1.242) showed a value 8.0 times the first group (FIG. 7).

[Example 9] Anti-HTLV Antibody Booster Effect of Non-Infectious Particle Expressing HTLV-1 Envelope Protein An immunity induction experiment was performed with mice (BALB/c) using the infectious particle (SeV18+gp63ectoF/dF) and the non-infectious particle (SeV18+gp63ectoF/dF/NVP) of F gene-deficient Sendai virus vector expressing gp63ectoF that is a fusion protein of the ectodomain of gp63 of HTLV-1 Env and the cytoplasmic domain of Sendai virus F protein. In the first group (n=6, SeV/SeV group), inoculation of the infectious particle (SeV18+gp63ectoF/dF) was performed four times (week 0, 4, 8 & 9), and in the second group (n=6, SeV/NVP group), inoculation of the infectious particle (SeV18+gp63ectoF/dF) was performed once (week 0) and inoculation of the non-infectious particle (SeV18+gp63ectoF/dF/NVP) was performed three times (weeks 4, 8 & 9). Further, in the third group as a negative control (n=4, PBS group), PBS inoculation was performed four times (week 0, 4, 8 & 9). In the inoculation of the infectious particle (SeV18+gp63ectoF/dF), $5.0\times10^7$ CIU (0.05 ml) was subjected to intramuscular inoculation, and in the inoculation of the non-infectious particle (SeV18+gp63ectoF/dF/NVP), $5.0\times10^9$ particles (0.05 ml) was subjected to intramuscular inoculation. Using blood collected at the time of euthanasia at the 11th week after the first inoculation, the anti-HTLV Env antibody titer was measured by ELISA.

In the antibody titer measurement by ELISA, HTLV-1 gp46 protein (Abcam, 200 ng/0.05 ml/well) was solid-phased in each well of a 96-well plate (Corning Costar #3690), blocked with 3% BSA/PBS, mouse blood plasma was then added, and the absorbance (OD450) was measured with a plate reader after peroxidase-labeled anti-mouse IgG antibody reaction and chromogenic reaction using a TMB substrate. As a result, in data using the blood plasma diluted 8,000-fold (average value of OD450 measurement value), both the first and second groups showed a high value, and particularly, the second group (SeV/NVP group) showed a significantly higher value than the control group. Further, in comparison on endpoint titer (the maximum dilution ratio in which the OD450 value exceeds the background), the second group (SeV/NVP group) showed a significantly higher value than the first group (SeV/SeV group) (FIG. 8). From the above results, even in the inoculation of the non-infectious particle (NVP) expressing gp63ectoF that has high safety in terms of not having infectiveness, anti-HTLV-1 Env antibody booster ability was higher than that in the inoculation of the infectious particle (SeV) expressing gp63ectoF.

[Example 10] Construction of F-Deficient Sendai Virus Carrying HIV-1 AD8-EO Strain Envelope Protein 1) Construction of Plasmid for Production of SeV Vector Carrying Ectodomain sfAD8EOEnvF Gene of AD8EO Strain-Derived Env (pSeV18+sfAD8EOEnvF/TSΔF)

Preparation of ectodomain sfAD8EOEnv of AD8EO strain (HIV-1 subtype B)-derived Env was carried out by PCR that uses, as a template, a plasmid carrying the Env gene of HIV-1 AD8EO strain (Shingai, M. et al., 2012, Proc Natl Acad Sci U.S.A. 109(48): 19769-19774), sfEnvF of HIV-1 BG505 strain, or each PCR product, and the PCR was carried out in three stages shown in FIG. 9. As the first stage, the PCR was carried out under the following conditions: 94° C. for 2 minutes, 30 cycles of (98° C. for 10 seconds, 55° C. for 30 seconds, 68° C. for 2 minutes), 68° C. for 5 minutes, and ∞ at 4° C., using KOD-Plus-Ver. 2 with a combination (1) of primer Sf_AD8-EO_N (5'-ggctagcgcagagAAT-TTGTGGGTCACAG-3' (SEQ ID NO: 18)) and primer AD8-EO_A450_G_C (5'-TATTGAAAGAGCAGTTcTTT-ATTTCTCCTC-3' (SEQ ID NO: 19)), a combination (2) of primer AD8-EO_A450_G_N (5'-GAG-GAGAAATAAAgAACTGCTCTTTCAATA-3' (SEQ ID NO: 20)) and primer AD8-EO_A831G_C (5'-CTGTACT-ATTATGTTcTTTGTATTGTCTG-3' (SEQ ID NO: 21)), a combination (3) of primer AD8-EO_A831G_N (5'-CA-GACAATACAAAgAACATAATAGTACAG-3' (SEQ ID NO: 22)) and primer AD8-EO_A1506G_C (5'-CTGTACT-ATTATGTTcTTTGTATTGTCTG-3' (SEQ ID NO: 21)), and a combination (4) of primer AD8-EO_A1506G_N (5'-CA-GACAATACAAAgAACATAATAGTACAG-3' (SEQ ID NO: 22)) and primer F_C (5'-CTCTCTTGAGTTcTT-TATATACCACAGCC-3' (SEQ ID NO: 23)) using the AD8EO strain Env gene as a template, and with a combination (5) of primer Not1_Sf_N (5'-ATATgcggccgcgacgc-caccATGACAGCATATATCCAGAG-3' (SEQ ID NO: 24)) and primer Sf_AD8-EO_C (5'-CCCACAAAT-Tctctgcgctagcctgacacg-3' (SEQ ID NO: 25)), and a combination (6) of primer F_N (5'-TATAAAgAACTCAAGAGA-GACTGTGATTAC-3' (SEQ ID NO: 26)) and primer EIS-NotI-3R(5'-CTGCGGCCGCGATGAACTTTCACCCTAAGTTTTTC-3' (SEQ ID NO: 27)) using sfEnvF of the HIV-1 BG505 strain as a template, and the amplified fragments (respectively, (1) about 0.4 kbp, (2) about 0.4 kbp, (3) about 0.7 kbp, (4) about 0.54 kbp, (5) about 0.13 kbp, (6) about 0.26 kbp) were purified using the QIAquick PCR purification kit. As the second stage, the PCR was carried out under the following conditions: 94° C. for 2 minutes, 30 cycles of (98° C. for 10 seconds, 55° C. for 30 seconds, 68° C. for 2 minutes and 30 seconds), 68° C. for 5 minutes, and ∞ at 4° C., using KOD-Plus-Ver. 2 with a combination (7) of primer Not1_Sf_N (5'-ATATgcggccgcgacgccaccATGACAG-CATATATCCAGAG-3' (SEQ ID NO: 24)) and primer AD8-EO_A450_G_C (5'-TATTGAAAGAGCAGTTcTTTAT-TTCTCCTC-3' (SEQ ID NO: 19)) using (1) and (5) as a template, with a combination (8) of primer AD8-EO_A450_G_N (5'-GAG-GAGAAATAAAgAACTGCTCTTTCAATA-3' (SEQ ID NO: 20)) and primer AD8-EO_A1506G_C (5'-CTGTACT-ATTATGTTcTTTGTATTGTCTG-3' (SEQ ID NO: 21)) using (2) and (3) as a template, and with a combination (9) of primer AD8-EO_A1506G_N (5'-CAGACAATA-CAAAgAACATAATAGTACAG-3' (SEQ ID NO: 22)) and primer EIS-NotI-3R (5'-CTGCGGCCGCGATGAACTTT-CACCCTAAGTTTTTC-3' (SEQ ID NO: 27)) using (4) and (6) as a template, and the amplified fragments (respectively, (7) about 0.5 kbp, (8) about 1.1 kbp, (9) about 0.7 kbp) were purified using the QIAquick PCR purification kit. As the third stage, the PCR was carried out under the following conditions: 94° C. for 2 minutes, and 40 cycles of (98° C. for 10 seconds, 55° C. for 30 seconds, 68° C. for 2 minutes and 30 seconds), 68° C. for 5 minutes and □ at 4° C., using KOD-Plus-Ver. 2 with a combination (10) of primer Not1_Sf_N (5'-ATATgcggccgcgacgccaccATGACAG-CATATATCCAGAG-3' (SEQ ID NO: 24)) and primer EIS-NotI-3R (5'-CTGCGGCCGCGATGAACTTT-CACCCTAAGTTTTTC-3' (SEQ ID NO: 27)) using (7), (8), and (9) as a template, and the amplified fragment ((10) about 2.3 kbp) was purified using the QIAquick PCR purification kit to purify sfAD8EOEnvF gene fragment.

The sfAD8EOEnvF gene fragment encodes the fusion protein in which the TM region and the cytoplasm region of the SeV F protein are fused to the C-terminal of the ectodomain of the HIV-1 AD8-EO strain envelope protein (including SU and a part of TM).

Then, the purified sfAD8EOEnvF fragment (having NotI sites at both ends) was subjected to the NotI treatment and was ligated to the NotI-cleaved site of pSeV18+/ΔF plasmid described above, and was subjected to cloning after being transformed into *E. coli*, and correct clones of nucleotide sequences were selected by sequencing, thereby obtaining pSeV18+sfAD8EOEnvF/ΔF plasmid.

2) Preparation (Re-Construction) of SeV Vector Carrying sfAD8EOEnvF Gene (SeV18+sfAD8EOEnvF/ΔF)

One day before transfection, $5\times10^5$ 293 T/17 cells were seeded into each well of a 6-well plate, and cultured under a 5% $CO_2$ condition at 37° C. Using TransIT-LT1 (Mirus), the aforementioned 293T/17 cells were transfected with a mixture of pCAGGS-NP (0.5 μg), pCAGGS-P4C (−) (0.5 μg), pCAGGS-L (TDK) (2 μg), pCAGGS-T7 (0.5 μg), pCAGGS-F5R (0.5 μg) (see WO 2005/071085), and the plasmid for preparing SeV vector carrying sfEnvF gene prepared above (pSeV18+sfAD8EOEnvF/ΔF) (5.0 μg). The cells were cultured under a 5% $CO_2$ condition at 37° C. for two days. Then, the transfected 293T/17 cells were detached with trypsin-EDTA from the well, suspended in a Try/PS/MEM culture medium, and then seeded on a helper cell LLC-MK$_2$/F/Ad (Li, H.-O. et al., J. Virology 74. 6564-6569 (2000), WO 00/70070) prepared in a separate well, and continuously cultured while the culture medium was exchanged every three to four days. By performing hemagglutination reaction using a part of the culture supernatant, the amount of the virus in the culture supernatant was monitored, and the culture supernatant was recovered after sufficient hemagglutination reaction was obtained. RNA was extracted from the recovered culture supernatant using the QIAamp Viral RNA Mini Kit, the carried gene (sfAD8EOenvF) region was amplified by RT-PCR using the RNA as a template, and the obtained RT-PCR product was subjected to sequencing to confirm the correct nucleotide sequence. The recovered culture supernatant containing the SeV18+sfAD8EOEnvF/ΔF virus was snap frozen in liquid nitrogen and then stored at −80° C.

3) Amplification of F-Deficient Sendai Virus Carrying sfAD8EOEnvF Gene (SeV18+sfAD8EOEnvF/ΔF)

The helper cell LLC-MK$_2$/F/Ad was cultured using 12 T225 flasks under a 5% $CO_2$ condition at 37° C. until the cell became semiconfluent, and infected at moi 5.0 for 1 hour using the culture supernatant containing the SeV18+sfAD8EOEnvF/ΔF virus prepared above. After infection, the culture supernatant was removed, and 30 mL of Try/GE/MEM culture medium per flask was added and cultured under a 5% $CO_2$ condition at 32° C. A part of the culture supernatant was appropriately collected, the state of virus production was confirmed by hemagglutination assay, and the culture supernatant recovered after obtaining sufficient hemagglutination reaction was used as an infectious particle solution of SeV18+sfAD8EOEnvF/ΔF virus.

[Example 11] Preparation of F-Deficient Sendai Virus Non-Infectious Particle Carrying HIV-1 AD8-EO Strain Envelope Protein The LLC-MK2 cell was cultured using 12 T225 flasks under a 5% $CO_2$ condition at 37° C. until the cell became semiconfluent, and infected at moi 5.0 for 1 hour using the culture supernatant including the SeV18+sfAD8EOEnvF/ΔF virus prepared above. After infection, the culture supernatant was removed, and 30 mL of Try/GE/MEM culture medium per flask was added and cultured under a 5% $CO_2$ condition at 32° C. A part of the culture supernatant was appropriately collected, the state of vector production was confirmed by hemagglutination assay, and the culture supernatant recovered after obtaining sufficient hemagglutination reaction was used as a solution of non-infectious particle SeV18+sfAD8EOEnvF/ΔF/NVP.

[Example 12] Anti-HIV-1 Antibody Booster Effect of Non-Infectious Particle Expressing HIV-1 Envelope Protein An immunity induction experiment was performed with mice (BALB/c) using the infectious particle (SeV18+sfEnvF/dF) and the non-infectious particle (SeV18+sfEnvF/dF/NVP) of F-deficient Sendai virus vector expressing sfEnv-F that is a fusion protein of the ectodomain of gp160 of HIV-1 Env and the cytoplasmic domain of Sendai virus F protein. Regarding EnvF, one using BG505 strain (HIV-1 subtype A)-derived ectodomain and one using AD8EO strain (HIV-1 subtype B)-derived ectodomain were used. In the first group (n=4, PBS group), PBS inoculation as a negative control was performed four times (week 0, 4, 8 & 9). In the second group (n=6, SeV/SeV-BG505 group), inoculation of the infectious particle expressing BG505EnvF (SeV18+sfBG505EnvF/dF) was performed four times (week 0, 4, 8 & 9), and in the third group (n=6, SeV/NVP-BG505 group), inoculation of the infectious particle expressing BG505EnvF (SeV18+sfBG505EnvF/dF) was performed once (weeks 0), and then, inoculation of the non-infectious particle expressing BG505EnvF (SeV18+sfBG505EnvF/dF/NVP) was performed three times (weeks 4, 8 & 9). Further, for reviewing the cross-reactivity expansion effect on antibodies by using a different antigen in boost, in the fourth group, inoculation of the infectious particle expressing BG505EnvF (SeV18+sfBG505EnvF/dF) was performed two times (week 0 & 4), and then, inoculation of the infectious particle expressing AD8EOEnvF (SeV18+sfAD8EOEnvF/dF) was performed two times (week 8 & 9), and in the fifth group, inoculation of the infectious particle expressing BG505EnvF (SeV18+sfBG505EnvF/dF) was performed once (weeks 0) and inoculation of the non-infectious particle expressing BG505EnvF (SeV18+sfBG505EnvF/dF/NVP) was performed once (weeks 4), and then, inoculation of the non-infectious particle expressing AD8EOEnvF (SeV18+sfAD8EOEnvF/dF/NVP) was performed two times (weeks 8 & 9). In the inoculation of the infectious particle (SeV18+sfBG505EnvF/dF or SeV18+sfAD8EOEnvF/dF), $5.0 \times 10^7$ CIU (0.05 ml) was subjected to intramuscular inoculation, and in the inoculation of the non-infectious particle (SeV18+sfBG505EnvF/dF/NVP or SeV18+sfAD8EOEnvF/dF/NVP), $5.0 \times 10^9$ particles (0.05 ml) was subjected to intramuscular inoculation. Using blood collected at the time of euthanasia at the 11th week after the first inoculation, anti-HIV-1 Env (BG505 gp120 and BaL gp120) antibody titer was measured by ELISA.

In the antibody titer measurement, HIV-1 BG505 gp120 protein (50 ng/0.05 ml/well) was solid-phased in each well of a 96-well plate (Corning Costar #3690), blocked with 3% BSA/PBS, mouse blood plasma was then added, and the absorbance (OD450) was measured with a plate reader after peroxidase-labeled anti-mouse IgG antibody reaction and chromogenic reaction using a TMB substrate. As a result of anti-BG505 gp120 antibody ELISA, in the average value of OD450 values and the endpoint titer, the third group (SeV/NVP-BG505 group) showed a value equal to or higher than a value of the second group (SeV/SeV-BG505 group), and the antibody booster ability by the non-infectious particle (NVP) expressing sfEnvF was shown to be equal to or higher than the infectious particle (SeV) expressing sfEnvF (FIG. 10).

For reviewing the cross-reactivity expansion effect on antibodies by boost inoculation of the non-infectious particle expressing AD8EOEnvF, similar anti-gp120 antibody ELISA was performed using BaL gp120 protein belonging to the same HIV-1 subtype B as AD8EO. As a result, in the endpoint titer, a high value was shown in the fourth group (SeV/SeV-AD8EO group) boosted by the infectious particle expressing AD8EOEnvF, and also in the fifth group (SeV/NVP-AD8EO group) boosted by the non-infectious particle expressing AD8EOEnvF, a value equal to the value of the fourth group was shown. Further, as a result of analysis of the ratio value of BG505 endpoint titer and BaL endpoint titer, the fourth and fifth groups showed a higher value than the second and third group boosted by the particle expressing BG505EnvF, and particularly, a high value was shown in the fifth group (FIG. 11). From the above results, by the boost inoculation of the non-infectious particle expressing sfEnvF using an antigen derived from a different strain, an antibody having high cross-reactivity can be effectively induced.

While the present invention has been described in preferred embodiments, it is obvious to those skilled in the art that the preferred embodiments can be modified. Thus, the present invention intends that the present invention can be embodied by methods other than those described in detail in the present specification. That is, the present invention encompasses all modifications encompassed in the gist or the range that the invention is not modified in essence of the appended "CLAIMS."

The contents described in any publication cited herein, including patents and patent applications, are hereby incorporated in their entireties by reference, to the extent that they have been disclosed herein.

INDUSTRIAL APPLICABILITY

The non-infectious particle of the present invention holds the antigen protein at a high level while holding high safety as compared to the existing infectious particle. Such characteristics of the non-infectious particle of the present invention support the advantage as a vaccine against pathogen or the like including virus and are considered to be extremely useful in prevention or treatment of infection.

The invention claimed is:

1. A F gene-deleted Sendai virus non-infectious particle, which lacks F protein of the Sendai virus on the surface of the virus particle, and holds an antigen protein of a heterologous pathogen on the surface of the virus particle, wherein the antigen protein of the heterologous pathogen is a fusion protein containing an antigen fragment of the pathogen at the outer side of the virus particle and a cytoplasmic region fragment of the F protein at the inner side of the virus particle.

2. The non-infectious particle of claim 1, wherein the antigen protein of the heterologous pathogen comprises all or part of an envelope protein of a retrovirus.

3. The non-infectious particle of claim 1, wherein the antigen protein of the heterologous pathogen comprises all or part of an envelope protein of HTLV-1 or HIV-1.

4. A composition comprising the non-infectious particle of claim 1.

5. A vaccine formulation comprising the non-infectious particle of claim 1.

6. The vaccine formulation of claim 5, which is for use in booster inoculation.

7. The vaccine formulation of claim 5, which is used in booster inoculation, wherein the pathogen is different from a pathogen from which an antigen for primary inoculation is derived.

8. A method for producing the non-infectious particle of claim 1, which comprises introducing into a cell a Sendai vector from which at least F protein gene has been deleted and which carries an antigen protein gene of a heterologous pathogen, and collecting a generated paramyxovirus non-infectious particle.

9. The non-infectious particle of claim 1, wherein the antigen fragment of the pathogen is all or part of an ectodomain of an envelope protein of a pathogenic virus.

10. The non-infectious particle of claim 9, wherein the pathogenic virus is a retrovirus.

11. The non-infectious particle of claim 9, wherein the pathogenic virus is a T cell infectious retrovirus.

12. The non-infectious particle of claim 11, wherein the T cell infectious virus is HTLV-1.

13. The non-infectious particle of claim 11, wherein the T cell infectious virus is HIV-1.

* * * * *